United States Patent [19]

Van Grinsven et al.

[11] Patent Number: 5,773,700

[45] Date of Patent: Jun. 30, 1998

[54] CONSTRUCTS CONTAINING IMPATIENS NECROTIC SPOT TOSPOVIRUS RNA AND METHODS OF USE THEREOF

[75] Inventors: Martinus Quirinius Joseph Marie Van Grinsven; Petrus Theodorus De Haan; Johannes Jacobus Ludgerus Gielen, all of Enkhuizen; Dirk Peters; Robert Willem Goldbach, both of Wageningen, all of Netherlands

[73] Assignee: Andoz Ltd, Basel, Switzerland

[21] Appl. No.: 764,100

[22] Filed: Dec. 6, 1996

Related U.S. Application Data

[63] Continuation of Ser. No. 214,064, Mar. 15, 1994, abandoned, which is a continuation of Ser. No. 32,235, Mar. 17, 1993, abandoned.

[30] Foreign Application Priority Data

Mar. 19, 1992 [GB] United Kingdom .................. 9206016

[51] Int. Cl.$^6$ .............................. A01H 5/00; C12N 15/82; C12N 15/33
[52] U.S. Cl. ...................... 800/205; 435/172.3; 435/418; 435/419; 435/320.1; 536/23.72
[58] Field of Search ........................ 800/205; 435/172.3, 435/418, 419, 320.1; 536/23.72; 514/44; 935/62, 64, 67

[56] References Cited

FOREIGN PATENT DOCUMENTS 426195  5/1991  European Pat. Off. ........ C12N 15/40

OTHER PUBLICATIONS

Lewin (1987) Science 237: 1570.
Wilson, TMA (1993) Proc. Natl. Acad Sci USA 90:3134–3141.
Nejidat et al (1990) Physiologica Plantanium 80: 662–668.
Gielen et al (1991) Bio/Technology 9:1363–1366.
Gadani et al (1990) Arch Virol 115:1–21.
Abel et al., Science 232, 738–743 (1986).
Law et al., J. Gen. Virol. 71, 933–938 (1990).
Law et al., J. Gen. Virol. 72, 2597–2601 (1991).
Law et al., Virology 188, 732–741 (Received May 20, 1992).
DeHaan et al. "The nucleotide sequence of the S RNA of Impatiens necrotic spot virus . . . " Febs Letters, v. 306, No. 1, Jan. 1992, pp. 27–32.
Pang et al. "Resistance to heterologous isolates of tomato spotted wilt virus in transgenic . . . " Phytopathology, v. 82, No. 10, 1992, pp. 1223–1229.
DeAvila et al. "Classification of tospoviruses based on phylogeny of nucleo–protein gene sequences" J. Gen. Virol., vol. 74, No. 2, Feb. 1993, pp. 153–159.
Law et al. "The M RNA of impariens necrotic spot tospovirus bunyavirdae has an ambisense genomic organization" Virology, vol. 188, No. 2, 1992, pp. 732–741.
German et al. "Tospovirus diagnosis molecular biology phylogeny and vector relationships" Annual Review of Phytopathology, vol. 30, 1992, pp. 315–348.
Law et al. "Nucleotide sequence of the 3' non–coding region and N gene of the S RNA . . . " Chemical Abstracts, v. 117, 1992, Abstract No. 185748.
Law et al. "A tomato spotted wilt virus with a serologically distinct N protein" J. Gen. Virol. v. 71, 1990, pp. 933–938.
DeAvila et al. "Characterization of a distinct isolate of tomato spotted wilt virus (TSWV) . . . " Biological Abstracts, v. 93, 1992, Abstract No. 118495.
Law, M.D. et al. "A Tomato Spotted Wilt–Like Virus with a Serologically Distinct N Protein" J. of Gen. Virology (1990), 71:001–006.
Law, M.D. et al. "Nucleotide Sequence of the 3' Non–Coding Region and N Gene of the S RNA . . . " J. of Gen. Virology (1991) 72:2597–2601.
de Avila, A.C. et al. "Characterization of a Distinct Isolate of Tomatoe Spotted Wilt Virus (TSWV) . . . " J. Phytophatology 134, 133–151 (19912).

*Primary Examiner*—Elizabeth F. McElwain
*Attorney, Agent, or Firm*—Lynn Marcus-Wyner; Michael P. Morris

[57] ABSTRACT

Recombinant Impatiens Necrotic Spot Virus (INSV) DNA constructs comprising an INSV DNA coding for transcription into INSV RNA sequences or into RNA sequences related thereto, the use of such DNA constructs to transform plants having reduced susceptibility to INSV infection and probes for the isolation of INSV or diagnosis of plant INSV related diseases.

17 Claims, 14 Drawing Sheets

CONSTRUCTS CONTAINING IMPATIENS NECROTIC SPOT TOSPOVIRUS RNA AND METHODS OF USE THEREOF

This is a Continuation of application Ser. No. 08/214,064, filed Mar. 15, 1994 now abandoned, which is a Continuation of application Ser. No. 08/032,235, filed Mar. 17, 1993, now abandoned.

FIELD OF THE INVENTION

The present invention relates to plants having reduced susceptibility to infection from tospoviruses, genetic material capable of generating tolerance to tospoviruses, probes suitable for isolating and diagnosing, and processes for obtaining such plants and genetic material and probes.

BACKGROUND OF THE INVENTION

Viral infections in plants are frequently responsible for detrimental effects in growth, undesirable morphological changes, decreased yield and the like. Such infections often result in a higher susceptibility to infection in infected plants to other plant pathogens and plant pests. Transmission of plant viruses generally occurs via insect or fungal carriers or may occur through mechanical means.

Plant breeders continuously look to develop varieties of crop plant species tolerant to or resistant to specific virus strains. In the past, virus resistance conferring genes have been transferred from wild types related to commercial plants into commercial varieties through breeding. The transfer of an existing resistance in the wild from the wild type gene pool to a cultivar is a tedious process in which the resistance conferring gene(s) must first be identified in a source (donor) plant species and then combined into the gene pool of a commercial variety. Resistance or tolerance generated in this way is typically active only against one or at best a few strains of the virus in question. One disadvantage of breeding cultivars for resistance to a particular virus species is that there is often a lack of a gene source suitable for conferring disease resistance within the crop species.

Other approaches to limit the effect of virus induced disease on plants include the use of chemicals such as insecticides, fungicides and the like which act against virus carriers, and/or rely on the employment of preventative methods such as efficient phytosanitary working conditions. However, the use of chemicals to combat virus disease by killing the carrier is subject to increasingly tougher governmental regulations which present growers with a decreasing scala of permitted chemical plant-protectants.

In an alternative, a system referred to as "cross-protection" may be employed. Cross-protection is a phenomenon in which infection of a plant with one strain of a virus protects that plant against superinfection with a second related virus strain. The cross-protection method preferentially involves the use of avirulent virus strains to infect plants, which act to inhibit a secondary infection with a virulent strain of the same virus. However, the use of a natural cross-protection system can have several disadvantages. The method is very labour intensive because it requires inoculation of every plant crop, and carries the risk that an avirulent strain may mutate to a virulent strain, thus becoming a causal agent for crop disease in itself. A further possible hazard is that an avirulent virus strain in one plant species can act as a virulent strain in another plant species.

Several studies have indicated that the viral coat protein of the protecting virus plays an important role in cross-protection and that protection occurs when the resident virus and the challenging virus have the same or closely related coat protein structures.

Recent developments in gene manipulation and plant transformation techniques have given rise to new methods for generating virus resistance in plants. Genetically engineered cross-protection is a form of virus resistance which phenotypically resembles natural cross-protection, but is achieved through the expression of genetic information of a viral coat protein from the genome of a genetically manipulated plant. Generation of virus resistance via genetic engineering has been described in for instance, EP 223 452 and reported by Abel et al [(1986) Science 232:738–743]. It was shown that expression of the tobacco mosaic virus strain U1 (TMV-U1) coat protein gene from the genome of a transgenic plant resulted in a delay of symptom development after infection with any TMV strain. Similar results with respect to coat protein-mediated protection have also been obtained for alfalfa mosaic virus (AMV), potato virus X (PVX) and cucumber mosaic virus (CMV).

Although TMV, CMV, AMV and PVX belong to different virus groups, they share a common architecture: in all such viruses the viral RNA is a positive strand RNA encapsidated by a viral coat consisting of many individual but identical viral coat proteins.

However, tospoviruses are essentially different from the plant viruses mentioned above. The genus tospovirus belongs to the family Bunyaviridae. All tospoviruses are transmitted by thrips. The virus particles are spherical in shape (80–120 nm in diameter) and contain internal nucleocapsids surrounded by a lipid envelope studded with glycoprotein surface projections. The multipartite genome consists of linear single stranded RNA molecules of negative or ambisense polarity. The terminal nucleotides of these RNA molecules are characterised by a consensus sequence as follows: 5' AGAGCAAUX...................GAUUGCUCU 3', wherein X is C or U. Members of the tospovirus group include tomato spotted wilt virus (TSWV), Impatiens necrotic spot virus (INSV), and tomato chlorotic spot virus (TCSV), also known as tomato mottled spot virus (TMSV) or TSWV-like isolate BR-O3. A general description of a tospovirus, using TSWV as a representative of the genus tospoviruses can be found in our co-pending application EP 426 195 herein incorporated by reference.

The tospovirus particle contains at least 4 distinct structural proteins: an internal nucleocapsid protein N of 29 kd and two membrane glycoproteins: G1, approximately 78 kd, and G2 approximately 58 kd. In addition, minor amounts of a large protein, L, approximately 260 kd have been detected in virus particles. Tospoviral genomes consist of three linear single stranded RNA molecules of about 2900 nucleotides (nt) (S RNA), about 5000 nt, (M RNA) and about 8900 nt (L RNA), each tightly associated with nucleocapsid proteins and a few copies of the L protein to form circular nucleocapsids. A schematic structure outlining most properties of an INSV is given in FIG. 1. Based on the above and other properties, INSV (like TSWV) has been classified as a member of the tospovirus genus.

Circumstantial evidence has been presented which suggests that an M RNA encoded gene is directly or indirectly involved in the synthesis of the G1 membrane glycoprotein [Verkleij and Peters, (1983) J. Gen. Virol. 64:677–686].

As mentioned above, tospoviruses such as TSWV, INSV and the like are transmitted by certain species of thrips. These tospovirus carriers belong to the family Tripidae and include tobacco thrips (*Frankliniella fusca* (Hinds.)), western flower thrips (*F. occidentalis* (Pergande)), common blossom thrips (*F. Schultzei* (Trybom)), chilli thrips (*Scirtothrips dorsalis* (Hood)), *Thrips setosus* (Moulton), onion thrips (*T. tabaci* (Lindeman)), *F. intonsa* and melon thrips (*T. palmi* (Karny)). The tospovirus is acquired by thrips only during their larval stages. Larvae can transmit the virus before they pupate but adults more commonly transmit the virus. Adult thrips can remain infective throughout their lives.

Tospoviruses are widespread in temperate, subtropical and tropical climate zones throughout the world. The current distribution of tospoviruses covers all continents and makes them one of the most widely distributed of groups of plant viruses. At least 370 plant species representing 50 plant families, both monocotyledons and dicotyledons, are naturally infected by tospoviruses of the Bunyaviridae. Tospoviruses seriously affect the production of food and ornamental crops. Symptoms of tospovirus infection in plants include stunting, ringspots, dark purple-brown sunken spots, stem browning, flower breaking, necrotic and pigmental lesions and patterns, yellows and non-necrotic mottle, mosaic in greens or even total plant death. Most plant hosts display only a few of these symptoms, however, the wide range of symptoms produced by tospovirus infection has complicated diagnosis of the disease and has led to individual diseases being given several different names. A further complication is that tospovirus symptoms within the same plant species may vary depending on the age of the plant, time of infection during the life-cycle of the plant, nutritional levels, environmental conditions, such as temperature, and the like.

Although TSWV has been known for many years, is widely distributed, and is the causal agent of a disease which leads to significant loss in yield in crops and ornamentals, limited progress has been made in identifying sources of genes capable of conferring resistance to TSWV or other tospoviruses. A monogenic TSWV tolerance has been identified in *Lycopersicon peruvianum*, but this trait has not been transferred to cultivated tomatoes so far, nor has a resistance source been identified for other crop species. The use of natural cross-protection systems to decrease the invasive effects by tospovirus strains capable of causing damage is not well documented. Limited positive results have been reported for tomato and lettuce.

The introduction of genetic information capable of conferring resistance or tolerance to tospoviruses into plant gene pools by means of genetic manipulation provides the breeder and grower alike with a new method for combatting tospovirus induced disease. In particular, it has been found that genetic manipulation techniques may be employed to confer resistance to INSV related disease in plants.

SUMMARY OF THE INVENTION

According to the present invention there is provided a recombinant INSV DNA construct comprising a DNA sequence coding for transcription into a) an RNA sequence of an INSV or an RNA sequence homologous thereto;

b) an RNA sequence of an INSV or an RNA sequence homologous thereto capable of encoding for an INSV protein or a part thereof, in which one or more codons have been replaced by synonyms, or an RNA sequence homologous thereto; or c) an RNA sequence complementary to an RNA sequence according to a) or b), which INSV DNA is under expression control of a promoter capable of functioning in plants and includes a terminator capable of functioning in plants.

The DNA sequences defined under a), b) and c) above, for the purposes of the present invention will be referred to as "INSV Related DNA Sequences" hereinafter. An INSV Related DNA Sequence according to the invention may be modified as appropriate to create mutants or modified sequences homologous to such INSV Related DNA Sequences from which they are derived, using methods known to those skilled in the art such as site-directed mutagenesis and the like. Such mutants or modified coding sequences are embraced within the spirit and scope of the invention.

The term "RNA sequence of an INSV" may refer to a sequence of the S, M or L RNA strand, preferably an S or M RNA strand, more preferably to an S RNA strand of an INSV.

The term "RNA sequence homologous to an RNA sequence of an INSV" refers to an RNA sequence of an INSV wherein a number of nucleotides have been deleted and/or added but which is still capable of hybridization to a nucleotide sequence complementary to an RNA sequence of an INSV under appropriate hybridization conditions. For the purposes of the present invention appropriate hybridization conditions may include but are not limited to, for example, an incubation for about 16 hours at 42° C., in a buffer system comprising 5×standard saline citrate (SSC), 0.5% sodium dodecylsulphate (SDS), 5×Denhardt's solution, 50% formamide and 100 µg/ml carrier DNA (hereinafter the buffer system), followed by washing 3× in buffer comprising 1×SSC and 0.1% SDS at 65° C. for approximately an hour each time Preferably, hybridization conditions employed in the present invention may involve incubation in a buffer system for about 16 hours at 49° C. and washing 3× in a buffer comprising 0.1×SSC and 0.1% SDS at 55° C. for about an hour each time. More preferably, hybridization conditions may involve incubation in a buffer system for about 16 hours at 55° C. and washing 3× in a buffer comprising 0.1×SSC and 0.1% SDS at 65° C. for approximately an hour each time.

The length of the INSV Related DNA Sequence will i.a. depend on the particular strategy to be followed, as will become apparent from the description hereinafter. In general, the INSV Related DNA Sequence may comprise at least 20, and suitably 50 or more nucleotides.

The term "promoter" refers to the nucleotide sequence upstream from the transcriptional start site and which contains all the regulatory regions required for transcription, including the region coding for the leader sequence of mRNA (which leader sequence comprises the ribosomal binding site and initiates translation at the AUG start codon).

Examples of promoters suitable for use in DNA constructs of the present invention include viral, fungal, bacterial, animal and plant derived promoters capable of functioning in plant cells. The promoter may express the DNA constitutively or differentially. Suitable examples of promoters differentially regulating DNA expression are promoters inducible by disease carriers, such as thrips, e.g. so-called wound-inducible promoters. It will be appreciated that the promoter employed should give rise to the expression of an INSV Related DNA Sequence at a rate sufficient to produce the amount of RNA necessary to decrease INSV susceptibility in a transformed plant. The required amount of RNA to be transcribed may vary with the type of plant. Particularly preferred promoters include the cauliflower mosaic virus 35S (CaMV 35S) promoter, derivatives thereof, and a promoter inducible after wounding by a disease carrier such as thrips, e.g. a wound inducible promoter. Examples of further suitable promoters include nopaline synthase, octopine synthase and the like.

The term "terminator" refers to a DNA sequence at the end of a transcriptional unit which signals termination of transcription. Terminators are DNA 3'-non-translated sequences that contain a polyadenylation signal, that causes the addition of polyadenylate sequences to the 3'-end of a primary transcript. Terminators active in plant cells are known and described in the literature. They may be isolated from bacteria, fungi, viruses, animals and/or plants. Examples of terminators particularly suitable for use in the DNA constructs of the invention include the nopaline synthase terminator of A. tumefaciens, the 35S terminator of CaMV and the zein terminator from Zea mays.

In accordance with the present invention, an RNA sequence is complementary to another RNA sequence if it is able to form a hydrogen-bonded complex therewith, according to rules of base pairing under appropriate hybridization conditions (as described hereinabove).

The present invention also provides a vector capable of introducing the DNA construct of the invention into plants and methods of producing such vectors.

The term "vector" as employed herein refers to a vehicle with which DNA constructs of INSV or fragments thereof may be incorporated into the cells of a host organism.

The term "plants" refers to differentiated plants as well as undifferentiated plant material such as protoplasts, plant cells, including cybrids and hybrids, seeds, plantlets and the like which under appropriate conditions can develop into mature plants, progeny thereof and parts thereof such as cuttings, fruits of such plants and the like.

The invention further provides plants comprising in their genome a DNA construct of the invention, and methods of producing such plants. Such methods include plant breeding, plantlets derived from protoplast fusion and the like.

The plants according to the invention have reduced susceptibility to diseases induced by INSV or diseases related to INSV infection and suffer from substantially fewer or none of the disadvantages and limitations of plants obtained by classical methods as mentioned hereinabove.

Many types of plants are susceptible to INSV infection however only in some types is INSV infection known to give rise to a disease state directly attributable to the virus. Such types of plants include the ornamental or flowering plants. Examples of such plants include but are not limited to Ageratum, Amaranthus, Anthirrhinum, Aquilegia, Begonia, Chrysanthemum, Cineraria, clover, Cosmos, cowpea, Cyclamen, Dahlia, Datura, Delphinium, Gerbera, Gladiolus, Gloxinia, Hippeastrum, Impatiens, Mesembryanthemum, petunia, Primula, Saint Paulia, Salpiglossis, Tagetes, Verbena, Viola, Vinca, Zinnia, Pelargonium and the like.

Other types of plants may be susceptible to INSV infection but these plants may not present disease symptoms directly associated with INSV infection, however such plants may present symptoms of a disease as a result of a secondary infection by a different organism made possible as a result of an initial infection by INSV. Such plants may therefore be viewed as being the subject of an INSV infection related disease and may include plants selected from a wider group of plant types. Further examples of this group of plant types may include vegetable and other crops. Such crop types include alfalfa, aubergine, beet, broad bean, broccoli, brussels sprouts, cabbage, cauliflower, celery, chicory, cow pea, cucumber, endive, gourd, groundnut, lettuce, melon, onion, papaya, pea, peanut, pepper, pineapple, potato, safflower, snap bean, soybean, spinach, squash, sugarbeet, sunflower, tobacco, tomato, water melon and the like.

The invention relates in particular to ornamental plants and preferably to those listed ornamental plants comprising in their plant genome a DNA construct of the invention.

The particular features of tospoviruses including those of INSV are illustrated hereinafter.

The S, M and L RNA are single stranded RNA molecules. The S RNA of INSV is about 3000 nucleotides long(SEQ. ID No.1; SEQ ID No. 2) and comprises two genes, one (SEQ ID No.3) encoding a non-structural protein (NSs) in viral sense, the other one (SEQ ID No.11) encoding the nucleocapsid protein (N) in viral complementary sense. The intergenic region between the NSs- and N-gene can be folded into a secondary structure (Seq ID No. 7 and SEQ ID No.8). The 5'- and 3'-terminal sequences of the S RNA are capable of hybridizing to each other such that the first nucleotide is opposite (and complementary) to the last nucleotide of said S RNA strand. For the purposes of the description the double-stranded structure obtained by hybridizing both RNA termini will be referred to as a "pan-handle" (SEQ ID No.5 and SEQ ID NO. 6) hereinafter.

The M RNA strand of INSV comprises about 5000 nucleotides (SEQ ID No. 14). It contains at least two open reading frames, one encoding a non-structural protein (NSm) in viral sense (SEQ ID No.15), and another open reading frame (SEQ ID No.21) in viral complementary sense. This open reading frame is translated on polysomes located on the endoplasmic reticulum where the nascent polypeptide chain is cleaved co-translationally to form the spike proteins G1 and G2 respectively. As with S RNA, the termini of the M RNA strand are complementary to each other and may likewise hybridize to form a "pan-handle" (SEQ ID No.18 and SEQ ID No.19).

The L RNA strand of INSV comprises about 8900 nucleotides. It contains complementary 3' and 5' ends for a length of from about 50 to about 80 nucleotides. The RNA has a negative polarity, with one open reading frame (ORF) located as the viral complementary strand. This ORF corresponds to a primary translation product of about 2875 amino acids in length with an anticipated Mw of between about 300,000 to about 350,000. Comparison with the polymerase proteins of other negative strand viruses indicates that this protein probably represents a viral polymerase. In some mutant strains, shortened L RNA molecules have been found in addition to the wild type, full length L RNA. These shortened L RNAs however are observed to possess the characteristic terminal nucleotide sequences and thus are capable of forming "pan handle" structures. They are also encapsidated with nucleocapsid protein and are included in virus particles. Their presence suppresses symptom development resulting in less severe detrimental effect. Thus, these shortened L RNA molecules can be regarded as defective interfering (DI) RNAs. A defective interfering RNA is one which is capable of interfering in replication by competing with other genomic RNAs for polymerases and therefore is capable of being replicated, and by so doing inhibits the replication and/or expression of other genomic RNA's with which it is competing. Thus, a DI RNA may comprise any RNA sequence which is capable of being replicated and may be an L, S, or M RNA within the context of the present invention. Such DI RNA sequences may comprise RNA sequences which have had nucleotides either deleted from or added thereto provided that they are capable of competing for polymerases and of replicating.

A preferred embodiment of the invention relates to DNA constructs of the invention coding for transcription into INSV RNA sequences of a "pan-handle" (SEQ ID No.5, SEQ ID No.6; SEQ ID No.18, SEQ ID No.19), or into INSV RNA sequences homologous thereto.

Another preferred embodiment of the invention relates to DNA constructs of the invention coding for transcription into INSV-RNA sequences of an open reading frame in viral complementary sense i.e. having negative polarity, or into corresponding RNA sequences in which one or more codons have been replaced by their synonyms, or into RNA sequences homologous thereto.

A further preferred embodiment of the invention relates to DNA constructs of the invention coding for transcription into INSV-RNA sequences of a hairpin (SEQ ID No.7, SEQ ID No.8; SEQ ID No.13, SEQ ID No.16) or into RNA sequences homologous thereto.

Preferably, the INSV-RNA sequence referred to hereinabove has at least 20 nucleotides. Preferably, the INSV-RNA sequence has at least 50 nucleotides.

Examples of DNA constructs suitable for use according to the invention include INSV-Related DNA Sequences coding for transcription into (reference is made to the sequence listing);

i) the viral S RNA nucleotide sequence from 1 to 3017 (SEQ. ID No.1)
ii) the viral S RNA nucleotide sequence from position 25 to 3017 (SEQ. ID No.2);
iii) the viral S RNA nucleotide sequence from 87 to 1436 (SEQ. ID No.3);
iv) the viral S RNA nucleotide sequence from 2080 to 2868 (SEQ. ID No.4);
v) the viral S RNA "pan-handle" structure comprising:
  a) a first nucleotide sequence of from about 30 to about 36 nucleotides in length from the 5' end of the viral S RNA and
  b) a second nucleotide sequence of from about 30 to about 36 nucleotides in length from the 3' end of the viral S RNA
vi) the viral S RNA nucleotide sequence from 1437 to 2079; (SEQ ID No. 7)
vii) the viral S RNA nucleotide sequence from 1440 to 2041; (SEQ ID No.8)
viii) the viral complementary S RNA nucleotide sequence from 1 to about 3017; (SEQ ID No.9)
ix) the viral complementary S RNA nucleotide sequence from 1 to 2993; (SEQ ID No.10)
x) the viral complementary S RNA nucleotide sequence from 150 to 938; (SEQ ID No.11)
xi) the S RNA nucleotide sequence from 1581 to 2930 of the viral complementary S RNA strand; (SEQ ID No.12);
xii) the viral complementary S RNA secondary structure having a nucleotide sequence of 642 nucleotides from 939 to 1580; (SEQ ID No.13)
xiii) S RNA nucleotide sequence from 87 to 1436 in which one or more codons have been replaced by their synonyms;
xiv) S RNA nucleotide sequence from 2080 to 2868 in which one or more codons have been replaced by their synonyms;
xv) the M RNA nucleotide sequence from 1 to 4970 (SEQ ID No.14);
xvi) the M RNA sequence from 86 to 997 (SEQ ID No.15);
xvii) the M RNA sequence of the intergenic region from 998 to 1470 (SEQ ID No.16);
xviii) the M RNA sequence from 1471 to 4884; (SEQ ID No. 17)
xix) the M RNA "pan-handle" structure comprising: a) a first nucleotide sequence of from about 30 to about 36 nucleotides in length from the 5' end of the viral M RNA and
  b) a second nucleotide sequence of from about 30 to about 36 nucleotides in length from the 3' end of the viral M RNA
xx) the complementary viral M RNA sequence from 1 to 4970; (SEQ ID No.20)
xxi) the complementary viral M RNA sequence from position 87 to position 3500 of the complementary viral M RNA sequence; (SEQ ID No.21)
xxii) the complementary viral M RNA sequence from position 3974 to 4885 (SEQ ID No.22)
xxiii) RNA sequences homologous to the nucleotide sequences defined under i) to xii) and xv) to xxii) hereinabove.
xxiv) fragments of sequences defined under i) to xxii) hereinabove.

Preferred INSV-Related DNA Sequences code for transcription into the RNA sequences according to sequences iv) to xii) and xv) to xxii) as defined above, or into RNA sequences homologous thereto, or into fragments thereof comprising at least 15 nucleotides, more preferably at least 20 nucleotides, and most preferably at least 50 nucleotides.

According to another preferred embodiment of the invention the DNA constructs of the invention comprise INSV Related DNA Sequences coding for transcription into a combination of the 5' and 3' terminal sequences (ie "panhandles") of viral S, M or L RNA respectively, more preferably of S or M RNA, and most preferably of S RNA. Examples of S RNA and M RNA terminal sequences include
i) a first nucleotide sequence 36 nucleotides in length from the 5' end of the viral S RNA:

5' AGAGCAATNN NNNNNNNNNN NNNNGAACAAC CCAAGC 3'

(SEQ ID No.5 i.e. nucleotides from position 1 to 36 of SEQ ID No.1, where N stands for A,T,G, or C)
and
a second nucleotide sequence 36 nucleotides in length from the 3' end of the viral S RNA:

5' GATTATATG ATGTTATATT CGTGACACAA TTGCTCT 3'

(SEQ ID No.6 ie nucleotides from position 2981 to 3017 of SEQ ID No.1)
ii) a first nucleotide sequence of 36 nucleotides in length from the 5' end of the viral M RNA:

5' AGAGCAATCA GTGCATCAAA ATTATATCTA GCCGAA 3'

(SEQ ID No.18 ie nucleotides from position 1 to 36 of SEQ ID No.13)
and
b) a second nucleotide sequence 36 nucleotides in length from the 3' end of the viral M RNA

5' TGTTGTATGT AGAGATTTTG TTTGCACTGA TTGCTC T 3'

(SEQ ID No.19 ie nucleotides from position 4941 to 4970 of SEQ ID No. 13)

In the case of the terminus at the 5' end of the S RNA it is not known whether or not there are sixteen or seventeen nucleotides in the unknown region demarked by a series of "N" s, however the exact number of nucleotides in this region is not considered to be critical to the formation of "pan-handle" structures so long as the 5' end of the S RNA is capable of complementing the 3' end of the S RNA thus enabling the formation of a "pan-handle" structure.

The invention further provides probes suitable for use as diagnostic tools for the diagnosis of disease in plants suspected of being infected with INSV tospoviruses. Such probes comprise a labeled oligonucleotide (RNA or DNA) sequence complementary to an RNA sequence of an INSV tospovirus. The desired length of the sequence and appropriate method for diagnostic use of probes are known by those skilled in the art. A suitable probe may comprise a nucleotide sequence of at least 12 to about 800 nucleotides, preferably at least 15, more preferably more than 30 nucleotides, and most preferably from about 400 to 600 nucleotides complementary to an RNA sequence of an INSV tospovirus.

Probes according to the invention are helpful in identifying INSV tospovirus RNA or parts thereof in infected plant material i.a. for diagnostic purposes prior to full presentation of disease symptoms in plants.

The invention accordingly also provides a diagnostic method of determining INSV tospovirus infection in plants which comprises detecting INSV tospovirus replicative forms employing the probes of the invention in dot-blot type assays.

Probes according to the invention are useful in the construction of and use of chimeric genes comprising a DNA sequence corresponding to an RNA sequence of an INSV tospovirus.

The DNA constructs of the invention may be obtained by insertion of an INSV Related DNA Sequence in an appropriate expression vector, such that the sequence is brought under expression control of a promoter capable of functioning in plants and its transcription is terminated by a terminator capable of functioning in plants.

The term "appropriate expression vector" as used herein refers to a vector containing a promoter region and a terminator region which are capable of functioning in plant cells.

The insertion of an INSV Related DNA Sequence into an appropriate expression vector may be carried out in a manner known per se. Suitable procedures are illustrated in the examples hereinafter.

Likewise the construction of an appropriate expression vector may be carried out in a manner known per se.

Plants according to the invention may be obtained by
a) inserting into the genome of a plant cell a DNA construct as hereinbefore defined;
b) obtaining transformed cells; and
c) regenerating from the transformed cells genetically transformed plants.

DNA vectors of the present invention may be inserted into the plant genome of plants susceptible to INSV infection. Such plant transformation may be carried out employing techniques known per se for the transformation of plants, such as plant transformation techniques involving Ti plasmids derived from *Agrobacterium tumefaciens, A. rhizogenes* or modifications thereof, naked DNA transformation or electroporation of isolated plant cells or organized plant structures, the use of micro-projectiles to deliver DNA, the use of laser systems, liposomes, or viruses or pollen as transformation vectors and the like.

Plants of the invention may be monitored for expression of an INSV-Related DNA Sequence by methods known in the art, including Northern analysis, Southern analysis, PCR techniques and/or immunological techniques and the like. The plants of the invention show decreased susceptibility to INSV infection as demonstrated by tests whereby the plants are exposed to INSV preferentially at a concentration in the range at which the rate of disease symptoms correlates linearly with INSV concentration in the inoculum.

Methods suitable for INSV inoculation are known in the art and include mechanical inoculation, and in particular, the use of appropriate vectors.

Plants of the invention may also be obtained by the crossing of a plant obtained according to the methods of the invention with another plant to produce plants having in their plant genome a DNA construct of the invention.

BRIEF DESCRIPTION OF THE DRAWINGS

The invention is illustrated by the following non-limiting examples and accompanying figures.

FIG. 7: Schematic review of the construction of a suitable plasmid comprising the INSV NSm protein-coding sequence.

FIG. 8: Schematic review of the construction of a suitable plasmid comprising the INSV G1/G2 glycoprotein precursor-coding sequence.

Figure 1:
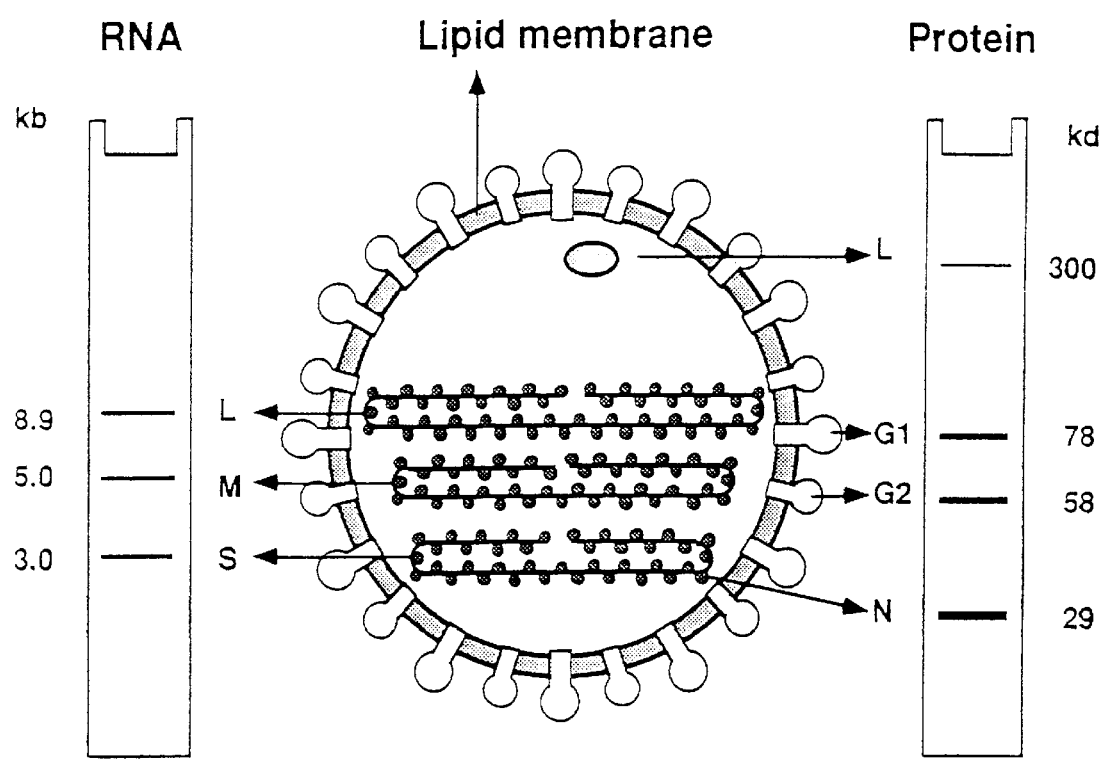
FIG. 1: Schematic representation of an INSV particle.

Suitable examples of preferred INSV Related DNA Sequences coding for transcription into a sequence of the secondary structure of the intergenic region of S RNA or of RNA sequences homologous thereto are sequences coding for the 1437 to 2079 nucleotide sequence of S RNA or for a sequence homologous to such sequences.

Other advantageous features of the present invention will be apparent from the following examples.

MATERIAL AND METHODS

All INSV RNA-derived sequences presented here are depicted as DNA sequences for the sole purpose of uniformity. It will be appreciated that this is done for convenience.

Cultivars of *Nicotiana tabacum* and *Petunia hybrida*, used in plant transformation studies, are grown under standard greenhouse conditions. Axenic explant material is grown on standard MS media [Murashige and Skoog, (1962) Physiol Plant 15:473–497] containing appropriate phytohormones and sucrose concentrations.

*E. coli* bacteria are grown on rotary shakers at 37° C. in standard LB-medium. *Agrobacterium tumefaciens* strains are grown at 28° C. in MinA medium supplemented with 0.1% glucose [Ausubel et al., (1987) Current Protocols in Molecular Biology, Green Publishing Associates and Wiley Intersciences, New York, Chichester, Brisbane, Toronto, and Singapore].

In all cloning procedures the *E. coli* strain JM83, (F$^-$, Δ(lac-pro), ara, rpsL, Ø80, dlacZM15) is used as a recipient for recombinant plasmids.

Binary vectors are conjugated to *Agrobacterium tumefaciens* strain LBA 4404, a strain containing the Ti-plasmid vir region, [Hoekema et al., (1983) Nature 303:179–180] in standard triparental matings using the *E. coli* HB101, containing the plasmid pRK2013 as a helper strain. [Figurski and Helinski, (1979) Proc. Natl. Acad. Sci.USA 76:1648–1652] Appropriate *Agrobacterium tumefaciens* recipients are selected on media containing rifampicin (50 µg/ml) and kanamycine (50 µg/ml).

Cloning of fragments in the vectors pUC19 [Yanish-Perron et al. (1985) Gene 33:103–119], pBluescript (Stratagene), pBIN19 [Bevan et al., (1984) Nucl Acids Res. 12:8711–8721] or derivatives, restriction enzyme analysis of DNA, transformation to *E. coli* recipient strains, isolation of plasmid DNA on small as well as large scale, nick-translation, in vitro transcription, DNA sequencing, Southern blotting and DNA gel electrophoresis are performed according to standard procedures [Maniatis et al., (1982) Molecular Cloning, a Laboratory Manual. Cold Spring Harbor Laboratory, New York; Ausubel et al. supra, (1987)].

DNA amplification using the polymerase chain reaction (PCR) were performed as recommended by the supplier of the Taq polymerase (Perkin Elmer Cetus).

Amplifications of RNA by reverse transcription of the target RNA followed by standard DNA amplification were performed using the Gene Amp RNA PCR Kit as recommended by the supplier (Perkin Elmer Cetus).

DESCRIPTION OF THE PREFERRED EMBODIMENTS

EXAMPLES

Example 1
Isolation of INSV particles and genetic material therein

INSV isolate NL-07, an isolate from Impatiens, is maintained on Impatiens by grafting. Virus is purified from systemically infected *Nicotiana rustica* leaves, after mechanical inoculation essentially as described by Tas et al. [(1977) J. Gen. Virol. 36:81–91]. All material used in the isolation procedure should be maintained at a temperature of 4° C. Twelve days after inoculation 100 grams of infected leaves are harvested and ground for 5–10 seconds at a low speed setting in 5 volumes extraction buffer (0.1M $NaH_2PO_4$, 0.01M $Na_2SO_3$, pH 7) in a Waring blender. The suspension is filtered through cheesecloth and the filtrate is centrifuged for 10 minutes at 16,000×g. The resulting pellet is resuspended in three volumes resuspension buffer (0.01M $NaH_2PO_4$, 0.01M $Na_2SO_3$, pH 7). The pellet is dissolved by stirring carefully at 4° C. After centrifuging for 10 minutes at 12,500×g the pellet is discarded and the supernatant centrifuged again for 20 minutes at 50,000×g. The pellet is resuspended in 0.2 volume of resuspension buffer (0.01M $NaH_2PO_4$, 0.01M $Na_2SO_3$, pH 7) and kept on ice for 30 minutes. Anti-serum raised in rabbits against material from non-infected *Nicotiana rustica* is added to the solution and carefully stirred for 1 hour. Non-viral complexes are pelleted after 10 minutes centrifuging at 16,000×g. The cleared supernatant is loaded on a linear 5%–40% sucrose gradient in resuspension buffer(0.01M $NaH_2PO_4$, 0.01M $Na_2SO_3$, pH 7), and spun for 45 minutes at 95,000×g. The opalescent band containing INSV particles is carefully collected with a syringe and diluted 4 times with resuspension buffer. Washed viruses are pelleted by centrifugation for 1.5 hours at 21,000×g and resuspended in one volume of resuspension buffer. Generally, 100 grams of leaf material yields approximately 0,5 mg of INSV viruses. INSV RNA is recovered preferentially from purified virus preparations by SDS-phenol extractions followed by ethanol precipitation. From 1 mg INSV, 1–5 µg of RNA is extracted. The isolated RNA molecules are analysed for intactness by electrophoresis on an agarose gel. Three distinct RNA molecules are identified with apparent sizes of about 3000 nucleotides (S RNA), about 4900 nucleotides (M RNA) and about 8900 nucleotides (L RNA) respectively.

Example 2

Sequence determination of the 3'-termini of the INSV viral RNAs

In order to perform direct RNA sequencing, INSV RNA is extracted from purified nucleocapsids essentially according to Verkleij et al. (1983) supra. Twelve days after inoculation 100 grams of infected leaves are harvested and ground for 5–10 seconds at a low speed setting in four volumes of TAS-E buffer (0.01M EDTA, 0.01M $Na_2SO_3$, 0.1% cysteine, 0.1M TRIS pH 8.0) in a Waring blender. The suspension is filtered through cheesecloth and centrifuged for 10 minutes at 1,100×g. Nucleocapsids are recovered from the supernatant after 30 minutes of centrifuging at 66,000×g. The pellet is carefully resuspended in one volume of TAS-R buffer (1% Nonidet NP-40, 0.01M EDTA, 0.01M $Na_2SO_3$, 0.1% cysteine, 0.01M glycine, 0.01M TRIS, pH 7.9). The pellet is dissolved by stirring carefully for 30 minutes at 4° C. The supernatant is cleared by centrifuging for 10 minutes at 16,000×g. Crude nucleocapsids are collected from the cleared supernatant by sedimentation through a 30% sucrose cushion for 1 hour at 105,000×g. The nucleocapsid pellet is resuspended in 400 μl 0.01M Na-citrate pH 6.5, layered on a 20–40% sucrose (in 0.01M Na-citrate pH 6.5) and spun for 2 hours at 280,000×g. The three different opalescent bands, respectively L, M and S nucleocapsid, are collected separately. INSV RNA is recovered preferentially from purified nucleocapsid preparations by SDS-phenol extractions followed by ethanol precipitation. Generally, 100 μg of RNA are obtained from 100 grams of infected leaves. The 3'-ends of the separate INSV RNAs are labeled using RNA ligase and 5'-[$^{32}P$]pCp. The end-labeled RNA molecules are separated on a low gelling temperature agarose gel [Wieslander, (1979) Anal Biochem 98:305–309]. The enzymatic approach described by Clerx-Van Haaster and Bishop [(1980) Virology 105:564–574] and Clerx-Van Haaster et al. [(1982) J Gen Virol 61:289–292] is used to determine the 30 terminal nucleotides of the 3'- and 5'-ends of both S and M RNA.

Synthetic oligonucleotides complementary to the 3'-termini are synthesized using a commercially available system (Applied Biosystems) and used for dideoxy-sequencing with reverse transcriptase.

Example 3 cDNA cloning of INSV genetic material

Oligonucleotides complementary to the 3'-end of the S RNA are used for priming first strand cDNA synthesis. With these primers, double stranded DNA to INSV RNA is synthesized according to Gubler and Hoffman [(1983) Gene 25:263–269].

Two different approaches are used to generate cDNA clones to the INSV viral RNAs. A first series of clones is obtained by random priming of the INSV RNA using fragmented single stranded calf thymus DNA, followed by first and second strand cDNA synthesis. cDNA is made blunt-ended using T4-DNA polymerase and ligated with T4 ligase into the SmaI site of pUC19.

A second series of INSV cDNA clones is obtained by priming first strand DNA synthesis with the oligonucleotides complementary to the 20 terminal nucleotides at the 3'-ends of the INSV RNAs. Blunt ended cDNA fragments are cloned into the Sma I site of pUC19.

cDNA clones from both series containing viral inserts are selected via colony hybridization, essentially according to the method of Grunstein and Hogness [(1975) Proc. Natl. Acad. Sci. USA 72:3961–3965] using [$^{32}$P]-labeled, randomly primed first strand cDNA as a probe. Sets of overlapping cDNA clones are selected by Southern analysis followed by plasmid walking, in order to construct a restriction map, based on cDNA derived sequences of the S RNA (FIG. 2).

Example 4
Sequence determination of the INSV S RNA

Figure 2:
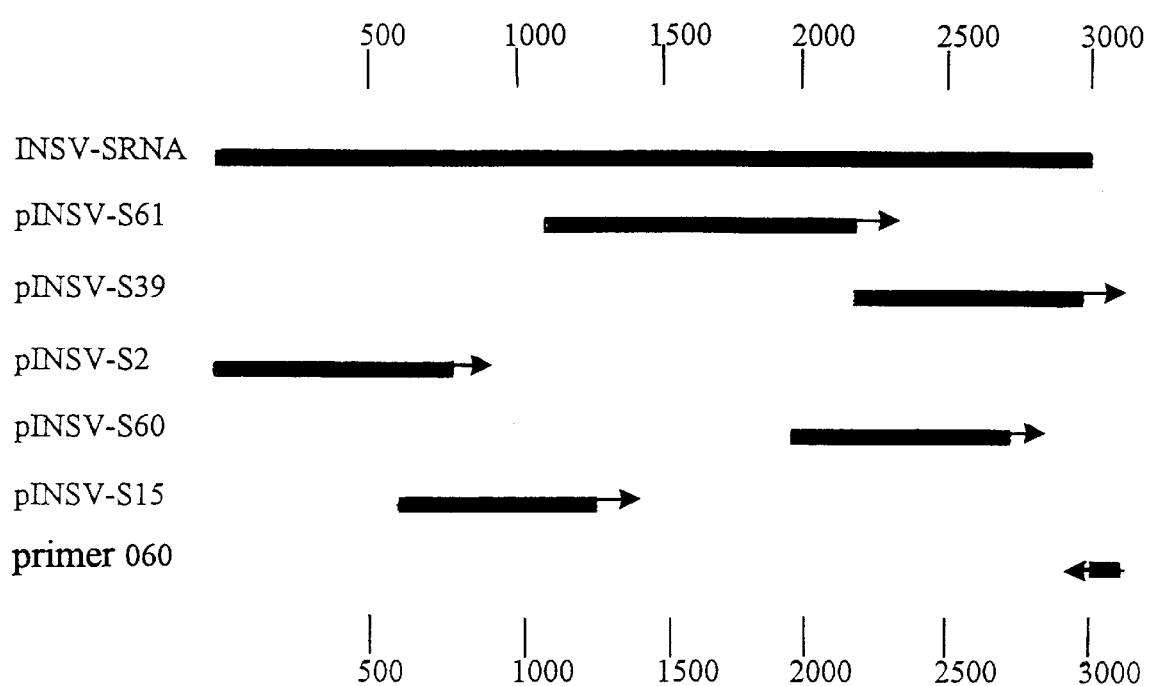
FIG. 2: Sequence strategy for INSV viral S RNA.

In order to determine the sequence of the S RNA 5 selected cDNA clones are subcloned into pBluescript, resulting in the plasmids pINSV-S2, pINSV-S15, pINSV-S61, pINSV-S60 and pINSV-S39, (FIG. 2). The clones are sequenced in both directions using the protocol of zhang et al. [(1988) Nucl. Acids. Res. 16:1220]. The nucleotide sequence of the 3'-end of the S RNA is determined by primer extension of the synthetic oligonucleotide INSV-S60 (5' d(AGAGCAATTGTGTCA) which is complementary to the 15 nucleotides of the 3'-terminus. Sequence data from the INSV S RNA (3017 nt) is summarized in the sequence listing (SEQ ID No.1 to SEQ ID No.12).

Figure 3:
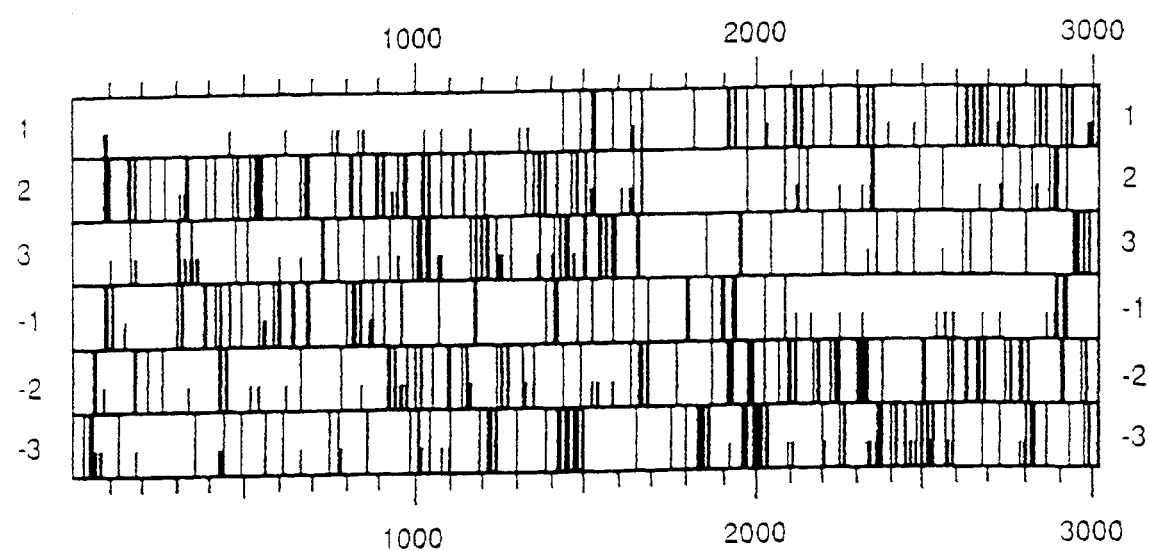
FIG. 3: Open reading frame analysis of the INSV S RNA, full bars represent translational stop codons (TAA, TAG, TGA), half size bars indicate start codons (ATG).

Computer simulated translation of the 6 different reading frames on the viral strand and viral complementary strand reveals the presence of two putative open reading frames (FIG. 3). On the viral strand an open reading frame is found starting at position 87 and terminating at a UAA stopcodon at position 1436 encoding a protein of 449 amino acids with a predicted molecular mass of about 51.2 kd. This protein is a non-structural protein, tentatively designated NSs (FIG. 3/SEQ ID No.26). The other open reading frame is located on the viral complementary strand from position 2080 to 2868 (SEQ ID No. 11), encoding a 262 amino acid long polypeptide with a predicted molecular mass of about 28.7 kd. This open reading frame encodes the viral nucleocapsid protein N (FIG. 3/SEQ ID No 25). Thus FIG. 3 shows the coding capacities of the viral and the viral complementary strand of INSV S RNA, indicating the NSs and N protein genes are expressed from subgenomic mRNAs (SEQ ID No.3, SEQ ID No.11 respectively). Thus, the situation occurs that a plant virus RNA has an ambisense gene arrangement. Other important features of this S RNA sequence is the existence of complementary terminal repeats capable of forming so-called "pan-handle" structures. These structures play an important role in replication and transcription of viral RNA. Another putative regulatory element is the secondary structure in the intergenic region of the S RNA, which most likely contains the transcription termination signals for both subgenomic mRNAs, encoding respectively the N and NSs-protein.

The nucleotide sequence of the INSV M and L RNA is elucidated employing similar strategies and methods as used to determine the nucleotide sequence of the S RNA.

Example 5
Construction of an expression vector pZU-B

The recombinant plasmid pZO347 is a derivative of pBluescript carrying a 496 bp BamHI-SmaI fragment containing a 426 bp 35S promoter fragment (HincII fragment) of CaMV strain Cabb-S, linked to a 67 bp fragment of the non-translated leader region, the so-called Ω-region, of the tobacco mosaic virus. This results in a chimeric promoter with a complete transcriptional fusion between the promoter of CaMV to the untranslated leader of TMV. By using in vitro mutagenesis the original position of the TMV ATG startcodon is mutated to a SmaI site.

Figure 4:
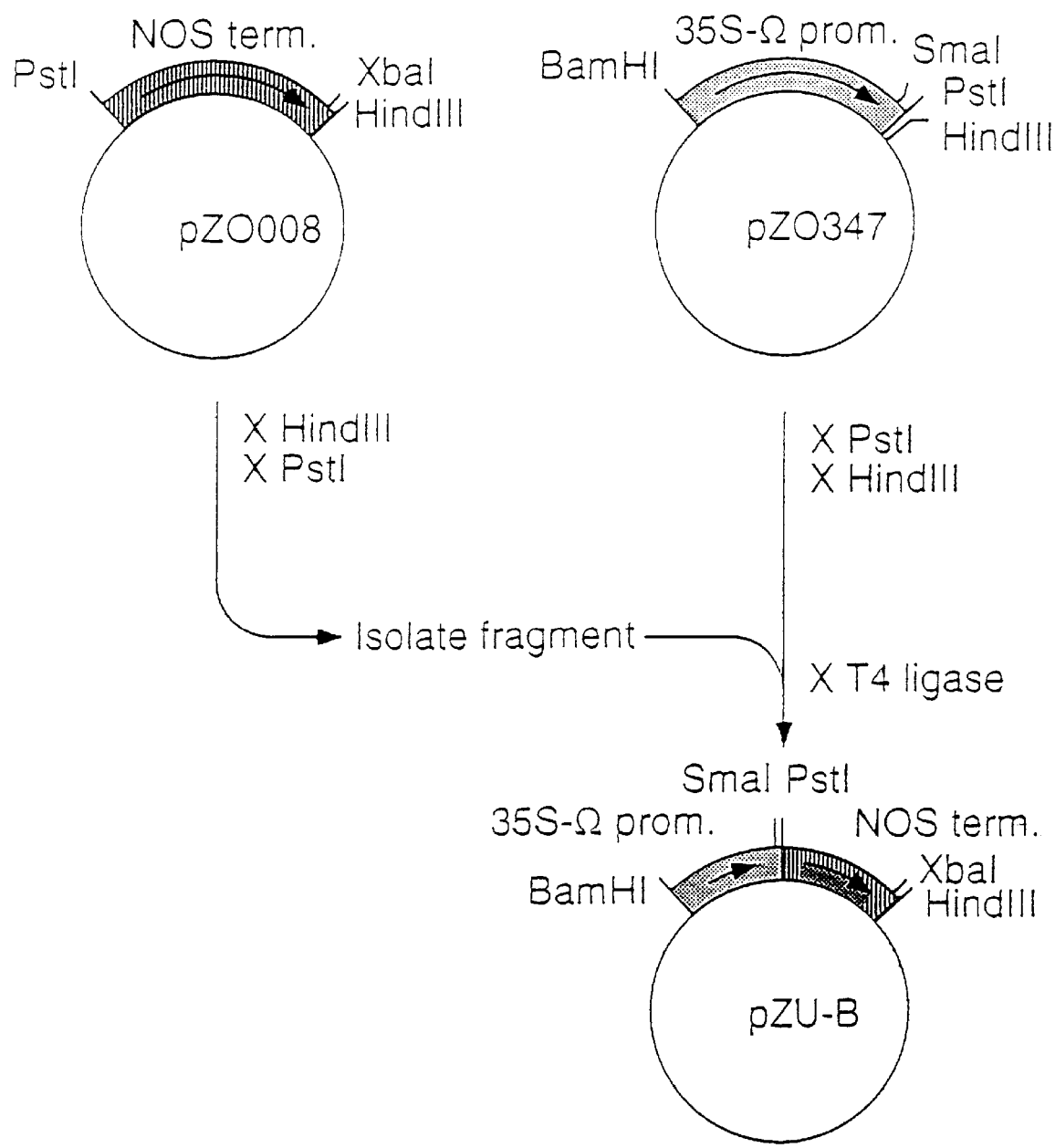
FIG. 4: Schematic review of the construction of a suitable expression vector (pZU-B).

The plasmid pZO008 carries the nopaline synthase (NOS) terminator as a 260 bp PstI-HindIII fragment. This PstI-HindIII fragment is excised from pZO008 and ligated using T4 ligase into PstI-HindIII linearized pZO347. The resulting recombinant plasmid pZU-B is another plant expression vector. The sequence of this 35S-Ω promoter as used in the plant expression vector pZU-B is shown as SEQ ID No.23. The resulting recombinant plasmid pZU-B contains the 35S HincII-TMV Ω fusion (35S-Ω), unique SmaI and PstI sites and the NOS terminator (FIG. 4). This expression vector is preferentially used in constructing translational fusions of the gene for expression downstream of the chimaeric promoter 35S-Ω.

Example 6
Subcloning of the INSV N protein gene

Figure 5A:
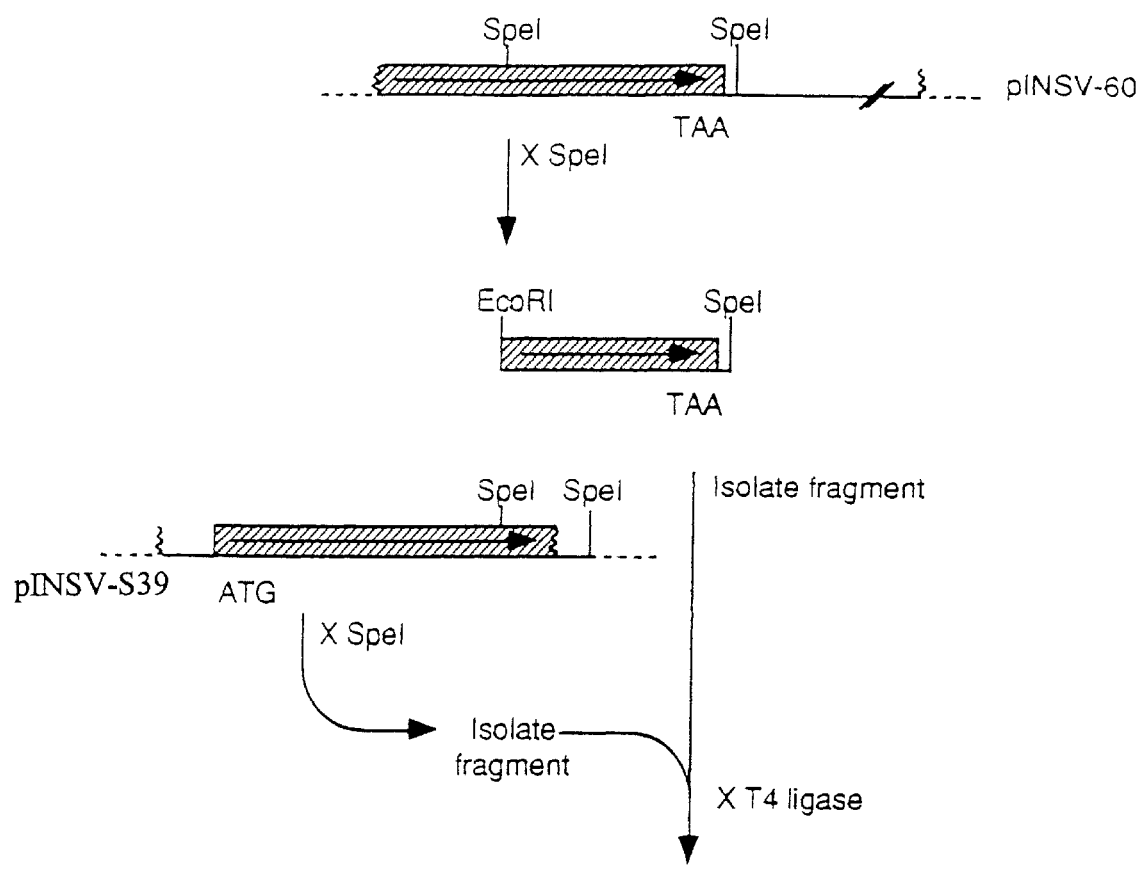
FIG. 5: Schematic review of the construction of a suitable plasmid comprising the INSV N protein-coding sequence.
Figure 5B:
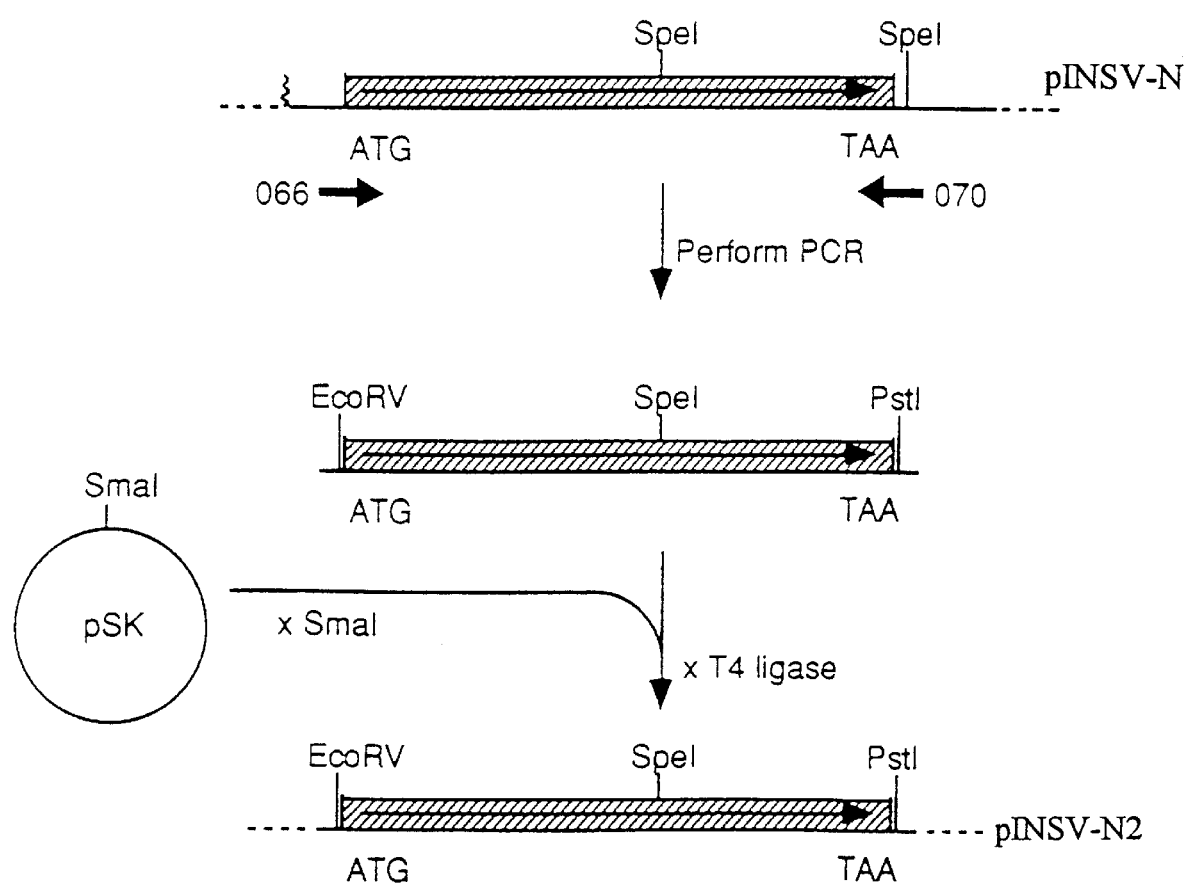

The INSV N protein coding sequence is obtained by fusion of the cDNA clones pINSV-S60 and pINSV-S39 (FIG. 5). The cDNA clone pINSV-S60 is subjected to SpeI digestion and the fragment containing the 3'-end of the INSV N protein gene is separated electrophoretically and purified from the gel using a DEAE membrane (NA-45, Schleicher and Schüll) and cloned in the largest SpeI fragment of pINSV-S39 linearized resulting in the recombinant plasmid pINSV-N. Primers are designed homologous to the translational start and stop codon. Primer INSV-066 d(GCAGATATCATGAACAAAGC) creates an EcoRV site just proximal to the start codon.

Primer INSV-070 d(GCAACCTGCAGCTCAAATCTCTT) creates a PstI site just distal to the stop codon. These primers are used in standard PCR experiments in which pINSV-N is used as the template. The resulting PCR fragment is isolated from the gel using a DEAE membrane (NA-45, Schleicher and Schüll) and cloned in the SmaI linearized pBluescript to generate plasmid pINSV-N2. The added restriction sites, EcoRV and PstI, facilitate the construction of further plasmids. (Alternatively, one may choose to add the sites in different ways such as but not limited to site-directed mutagenesis or by ligation of other synthetic oligonucleotide linkers. Such methods are all known to a person skilled in the art.)

Figure 6:
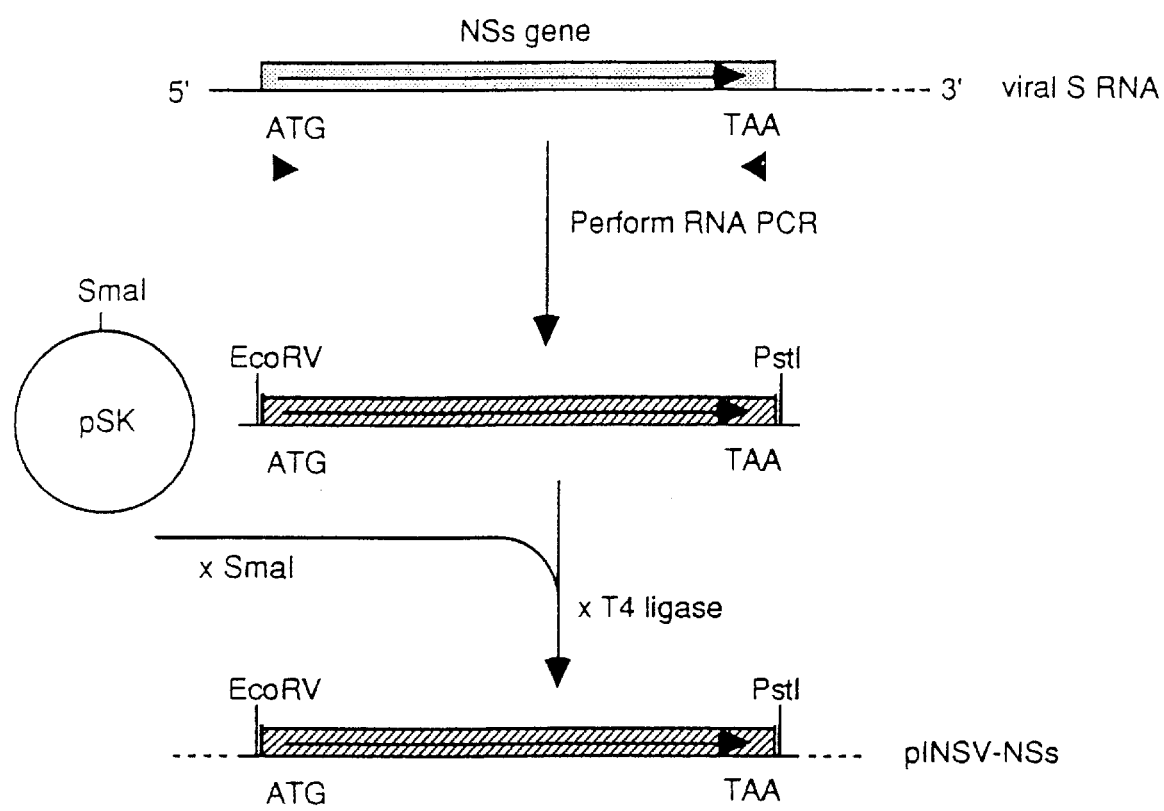
FIG. 6: Schematic review of the construction of a suitable plasmid comprising the INSV NSs protein-coding sequence.

Example 7
Subcloning of the INSV non-structural protein genes (NSs gene) of INSV S RNA The sequence of the gene corresponding to the non-structural protein NSs is isolated using RNA based PCR on isolated INSV S RNA. Two primers are designed which are homologous to regions spanning either the translational start codon or stop codon. The start codon primer contains an EcoRV site proximal to the ATG codon, the stop codon primer has a PstI site just distal thereto. Purified INSV S RNA is subjected to the Gene AMP RNA PCR. The resulting PCR fragment is isolated from the gel and cloned into SmaI linearized pBluescript yielding the recombinant plasmid pINSV-NSs (FIG. 6).

Figure 7:
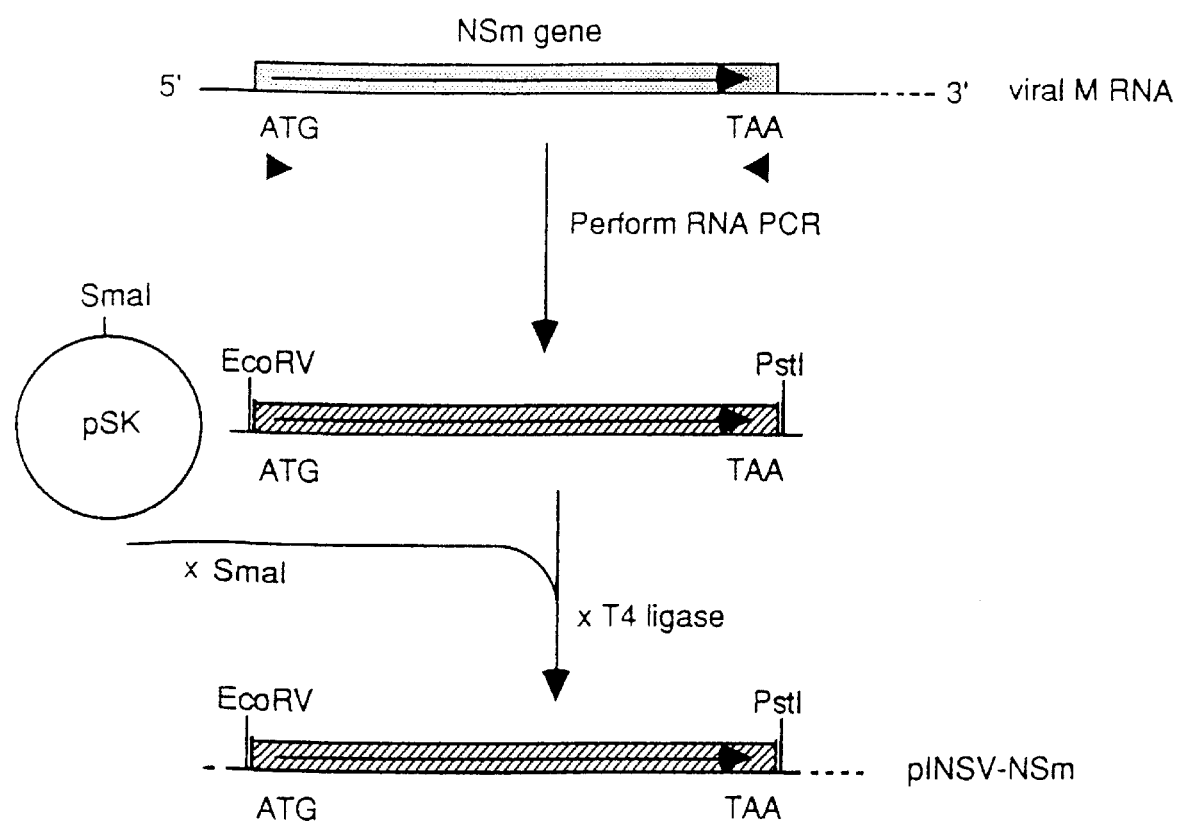

Example 8
Subcloning of the INSV non-structural protein gene (NSm gene) of the INSV M RNA The sequence of the gene corresponding to the non-structural protein NSm is isolated using RNA based PCR on isolated INSV M RNA. Two primers are designed which are homologous to regions spanning either the translational start codon or stop codon. The start codon primer contains an EcoRV site proximal to the ATG codon, the stop codon primer has a PstI site just distal thereto. Purified INSV S RNA is subjected to the Gene AMP RNA PCR. The resulting PCR fragment is isolated from the gel and cloned into SmaI linearized pBluescript yielding the recombinant plasmid pINSV-NSm (FIG. 7).

Figure 8:
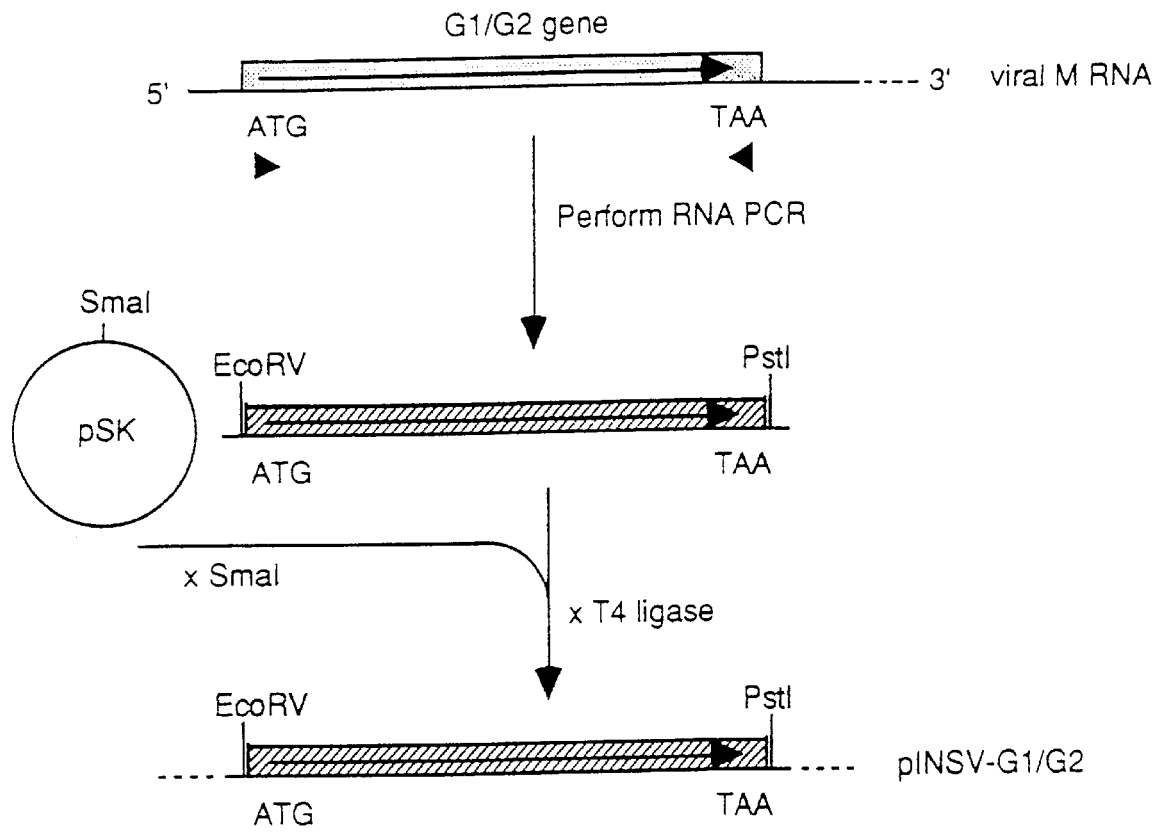

Example 9
Subcloning of the INSV G1/G2 glycoprotein gene (G1/G2 gene) of the INSV M RNA The sequence of the gene corresponding to the G1/G2 glycoprotein precursor is isolated using RNA based PCR on isolated INSV M RNA. Two primers are designed homologous to regions spanning either the translational start codon or stop codon. The start codon primer contains an EcoRV site proximal to the ATG codon, the stop codon primer has a PstI site just distal thereto. Purified INSV M RNA is subjected to the Gene AMP RNA PCR. The resulting PCR fragment is isolated from the gel and cloned into SmaI linearized pBluescript yielding the recombinant plasmid pINSV-G1/G2 (FIG. 8).

Figure 9:
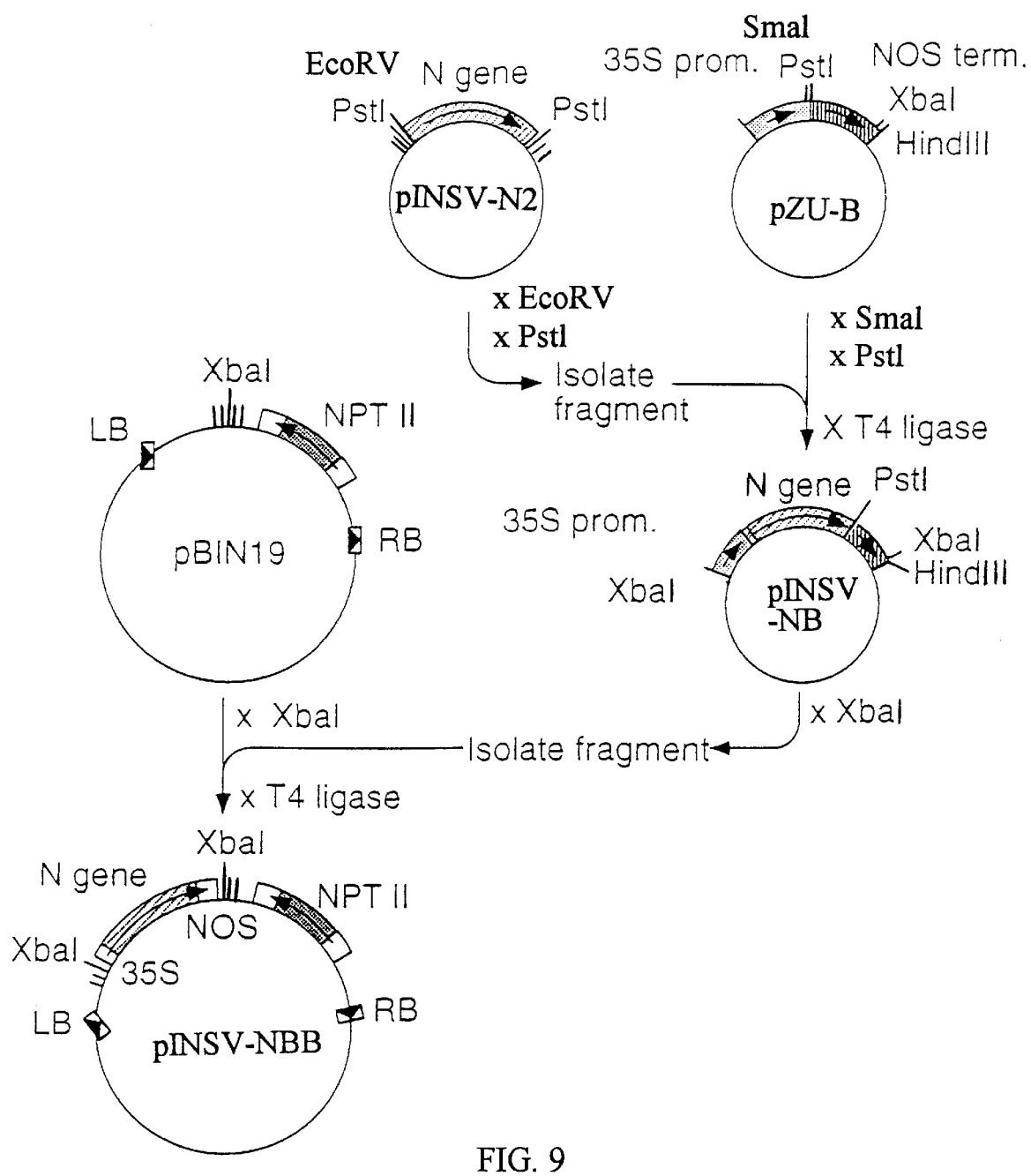
FIG. 9: Schematic review of the construction of a INSV N gene-containing plant transformation vector.

Example 10
Construction of plant transformation vectors containing INSV sequences Example 10A
N protein constructions in pZU-B In order to make a fusion in which the ATG start codon from the N protein gene is fused directly to the 3'-end of the TMV untranslated leader of the 35S-Ω promoter the start codon of the N gene has to be mutated using the PCR approach as hereinbefore described. The N protein gene is excised from the plasmid pINSV-N2 via an EcoRV-PstI digestion. The fragment is isolated and inserted into the SmaI-PstI linearised pZU-B, resulting in recombinant plasmid pINSV-NB. The chimeric cassette containing the 35S-Ω promoter, the N gene and the NOS terminator is excised from the plasmid pINSV-NB via a BamHI/XbaI digestion. The isolated chimaeric gene cassette is then inserted into the BamHI/XbaI linearized pBIN19 to create the binary transformation vector pINSV-NBB. The resulting plasmid pINSV-NBB (FIG. 9) is used in plant transformation experiments using methods well known to a person skilled in the art.

Example 10B
NSs protein gene constructions in pZU-B

Figure 10:
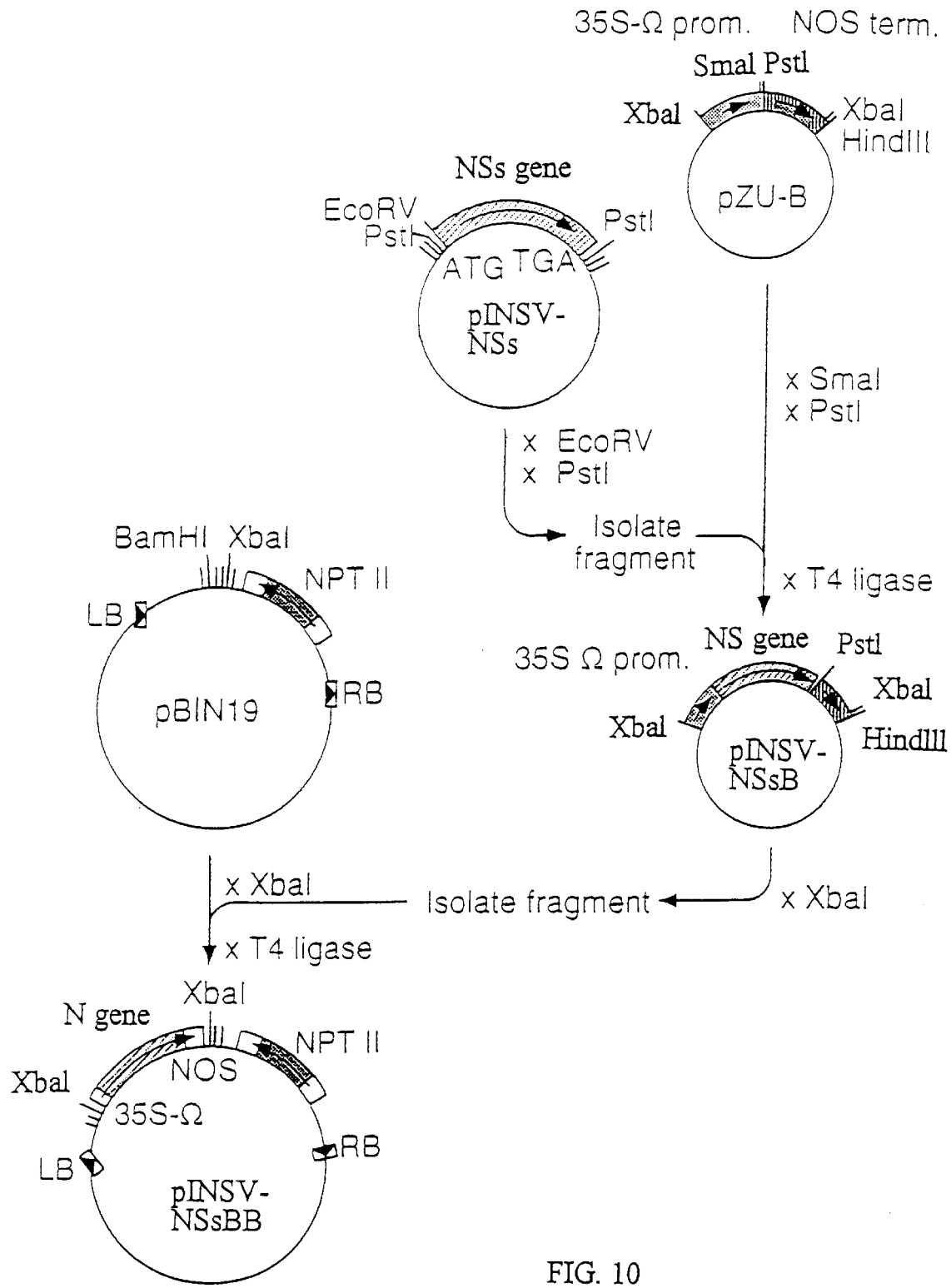
FIG. 10: Schematic review of the construction of a INSV NSs gene-containing plant transformation vector.

In order to create a fusion in which the ATG start codon from the NSs protein is fused directly to the 3'-end of the TMV leader of the 35S-Ω promoter the start codon of the NSs gene is mutated, using the PCR approach. The plasmid PINSV-Ns is digested with EcoRV and PstI and the NSs containing fragment is isolated from the gel and inserted into SmaI/PstI linearized pZU-B resulting in the recombinant plasmid pINSV-NSsB. The chimaeric cassette containing the 35S-Ω promoter, the mutated NSs protein gene and the NOS terminator is excised from the plasmid pINSV-NSsB via a BamHI/XbaI digestion. The isolated chimeric gene cassette is then inserted into the BamHI/XbaI linearized pBIN19 to create the binary transformation vector pINSV-NSsBB. The resulting plasmid pINSV-NSsBB (FIG. 10) is used in plant transformation experiments using methods well known to a person skilled in the art.

Example 10C
G1/G2 glycoprotein gene constructions in pZU-B

Figure 11:
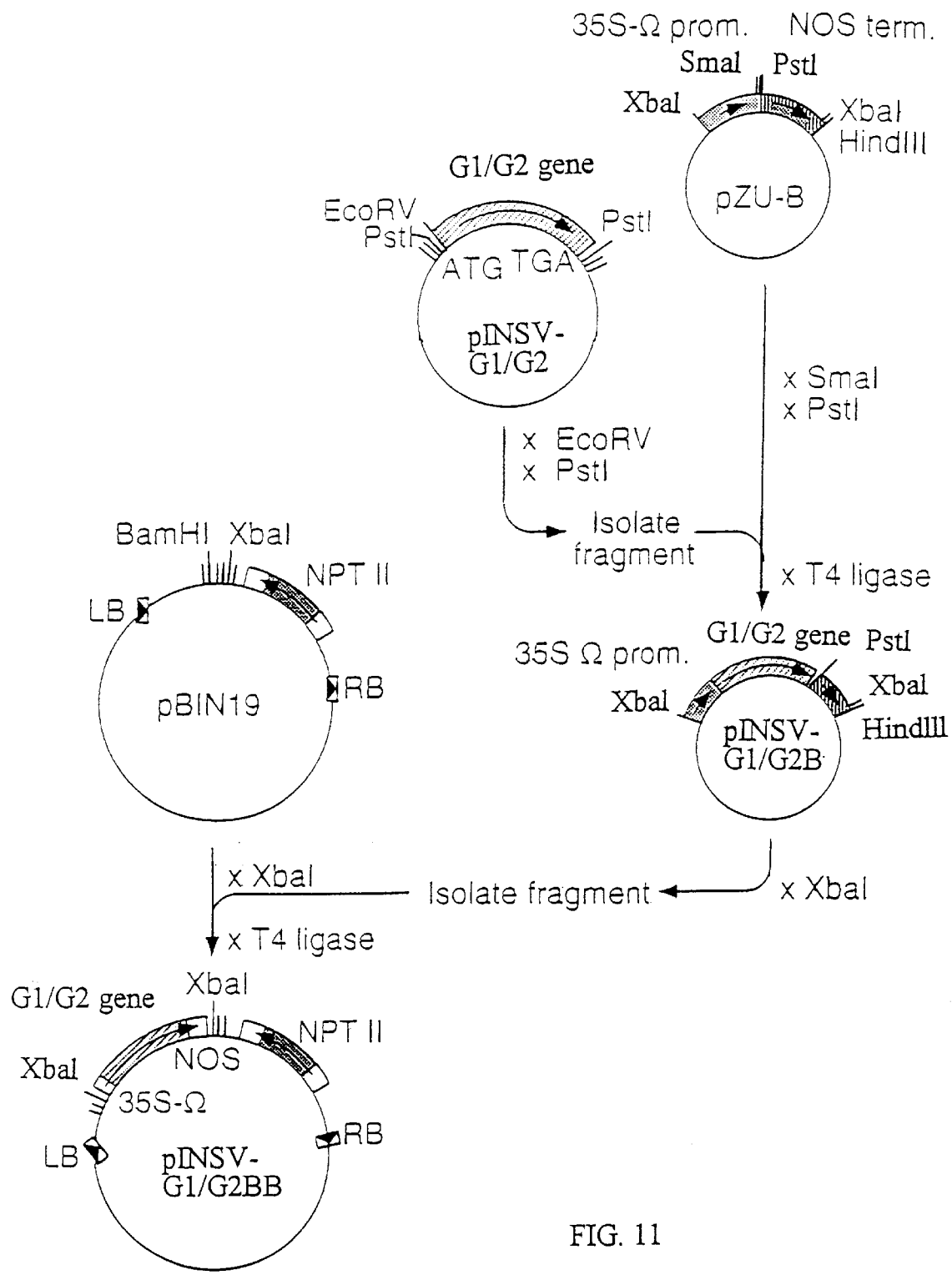
FIG. 11: Schematic review of the construction of a INSV G1/G2 glycoprotein precursor gene-containing plant transformation vector.

In order to create a fusion in which the ATG start codon from the G1/G2 glycoproteinprecursor is fused directly to the 3'-end of the TMV leader of the 35S-Ω promoter the start codon of the G1/G2 gene is mutated, using the PCR approach. The plasmid pINSV-G1/G2 is digested with EcoRV and PstI and the G1/G2 containing fragment is isolated from the gel and inserted into SmaI/PstI linearized pZU-B resulting in the recombinant plasmid pINSV-G1/G2B. The chimeric cassette containing the 35S-Ω promoter, the mutated G1/G2 glycoprotein gene and the NOS terminator is excised from the plasmid pINSV-G1/G2B via a BamHI/XbaI digestion. The isolated chimeric gene cassette is then inserted into the BamHI/XbaI linearized pBIN19 to create the binary transformation vector pINSV-G1/G2BB. The resulting plasmid pINSV-G1/G2BB (FIG. 11) is used in plant transformation experiments using methods well known to a person skilled in the art.

Example 10D
NSm protein gene constructions in pZU-B

Figure 12:
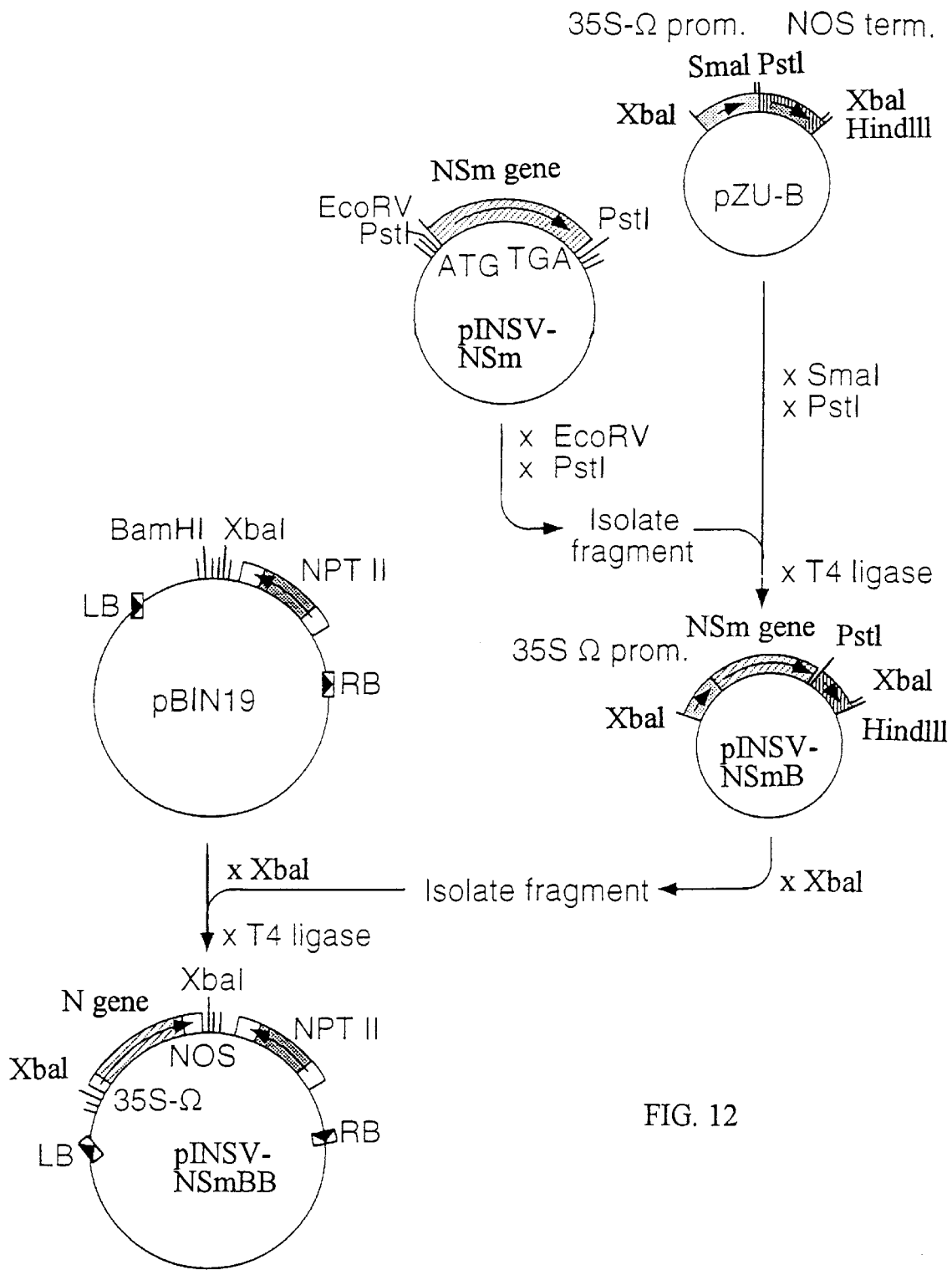
FIG. 12: Schematic review of the construction of a INSV NSm gene-containing plant transformation vector.
Figure 13:
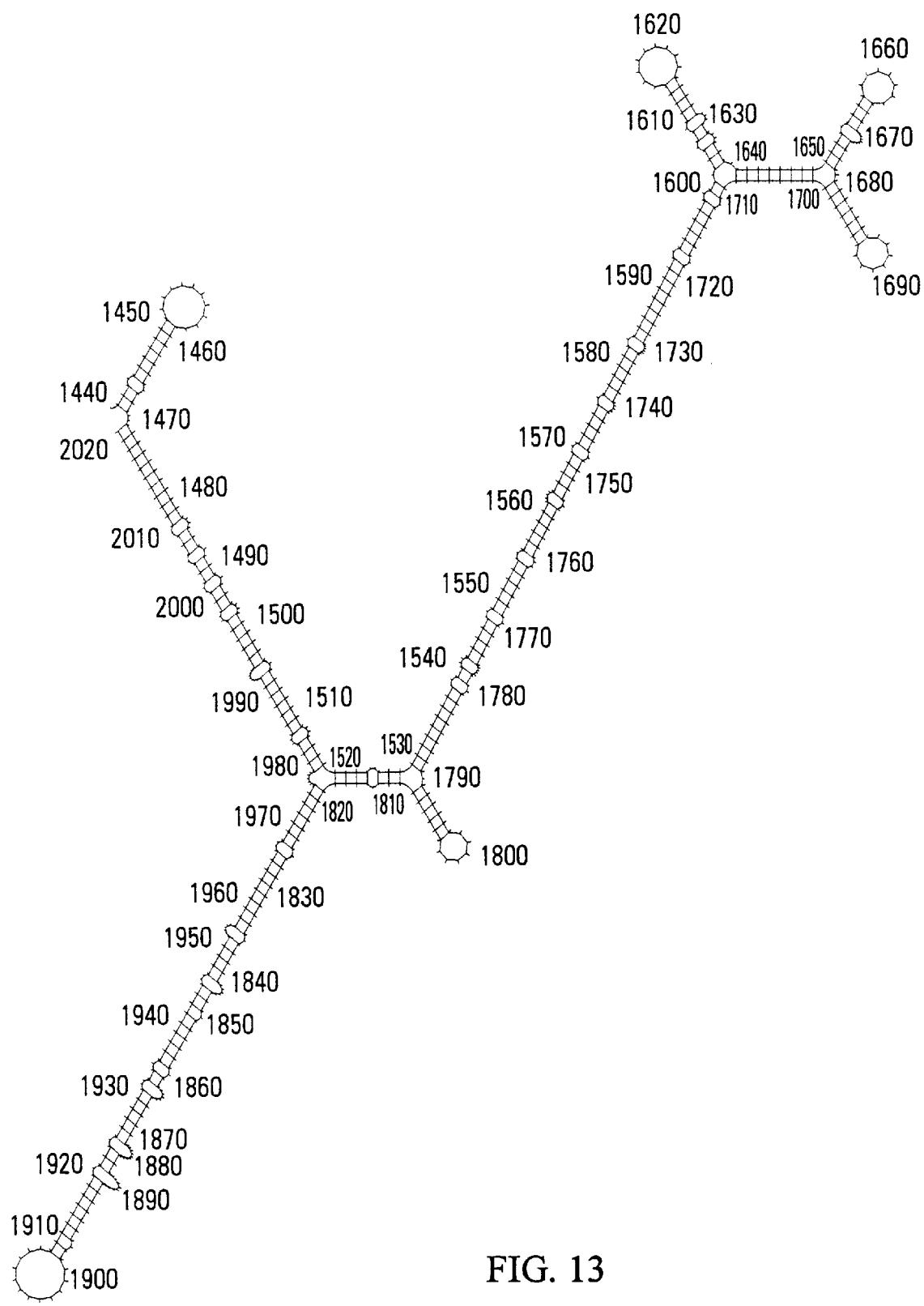
FIG. 13: The secondary structure located at the intergenic region of INSV S RNA.

In order to create a fusion in which the ATG start codon from the NSm protein is fused directly to the 3'-end of the TMV leader of the 35S-Ω promoter the startcodon of the NSm gene is mutated, using the PCR approach. The plasmid pINSV-NSm is digested with EcoRV and PstI and the NSm-containing fragment is isolated from the gel and inserted into SmaI/PstI linearized pZU-B resulting in the recombinant plasmid pINSV-NSmB. The chimeric cassette containing the 35S-Ω promoter, the mutated NSm protein gene and the NOS terminator is excised from the plasmid pINSV-NSmB via a BamHI/XbaI digestion. The isolated chimeric gene cassette is then inserted into the BamHI/XbaI linearized pBIN19 to create the binary transformation vector pINSV-NSmBB. The resulting plasmid pINSV-NSmBB (FIG. 12) is used in plant transformation experiments using methods well known to a person skilled in the art.

Example 10E
5'- and 3'-termini "pan-handle" constructions in pZU-B

A DNA analysis programme is used to locate the "pan-handle" element of the loop in the viral INSV S RNA. The strongest "pan-handle" structure that is detected includes about the first 24–25 nucleotides at the 5'-end (1 to 24 or 25) of the viral S RNA and about the last 36 nucleotides at the 3'-end of the viral S RNA (SEQ ID Nos 5 and 6 respectively). The length of the pan-handle element of the loop is about 36 nucleotides long.

These regions are synthesized on a commercial DNA synthesizer and appropriate linker sequences are added. Construction of the "pan-handle" vectors of S and M RNA results in respectively: pINSV-termS and pINSV-termM. Using appropriate restriction enzyme combination these fragments are inserted between the 35S-Ω promoter and the NOS terminator of pZU-B yielding the chimeric cassettes: pINSV-termSA, pINSV-termMA, pINSV-termSB and pINSV-termMB. These cassettes are then transferred into the binary transformation vector pBIN19 using appropriate enzyme combinations yielding the following plasmids: pINSV-termSAB, pINSV-termMAB, pINSV-termSBB and pINSV-termMBB. Alternatively, it is possible to design "pan-handle" constructs including the 3'- and 5'-end termini that are larger than indicated above, or separated by any other DNA sequence in order to enhance the stability of the transcripts produced from these recombinant genes in plants. All "pan-handle" constructs resemble shortened tospovirus RNA molecules, specifically INSV RNA molecules and therefore can be regarded as defective interfering RNAs.

Example 10F
Construction containing INSV S RNA secondary structure region in pZU-B A DNA analysis programme is used to locate a secondary structure in the viral INSV S RNA. The strongest secondary structure detectable starts at nucleotide 1440 and ends at nucleotide 2041 of SEQ ID No.1, (SEQ ID No 8).

The DNA fragment carrying the secondary structure region is isolated from pINSV-S61 using a PCR approach similar to that described earlier. The two primers used contain the sequences 1440–1460 and 2021–2041 of SEQ ID No.1. The PCR fragment is excised from an agarose gel and subsequently treated with T4 polymerase to create blunt ends and is subsequently cloned into the SmaI site of the expression vector pZU-B, resulting in the recombinant plasmid PINSV-HpSB. The plasmid pINSV-HpSB is digested with HindIII and the fragment containing the chimeric gene is excised from an agarose gel and ligated into XbaI linearized pBIN19, resulting in the transformation vector pINSV-HpSBB.

(It is clear to a person skilled in the art that other fragments can be isolated from the cDNA clones of the INSV S RNA containing the hairpin region as described above without interference to function. Also, a fragment containing the hairpin region may be synthesized using a DNA-synthesizer.)

Example 11
Transformation of binary vectors to tobacco plant material

Methods to transfer binary vectors to plant material are well established and known to a person skilled in the art. Variations in procedures exist due to for instance differences in used Agrobacterium strains, different sources of explant material, differences in regeneration systems depending on as well the cultivar as the plant species used.

The binary plant transformation vectors as described above are used in plant transformation experiments according to the following procedures. The constructed binary vector is transferred by tri-parental mating to an acceptor *Agrobacterium tumefaciens* strain, followed by southern analysis of the ex-conjugants for verification of proper transfer of the construct to the acceptor strain, inoculation and cocultivation of axenic explant material with the *Agrobacterium tumefaciens* strain of choice, selective killing of the *Agrobacterium tumefaciens* strain used with appropriate antibiotics, selection of transformed cells by growing on selective media containing kanamycine, transfer of tissue to shoot-inducing media, transfer of selected shoots to root inducing media, transfer of plantlets to soil, assaying for intactness of the construct by southern analyses of isolated total DNA from the transgenic plant, assaying for proper function of the inserted chimeric gene by northern analysis and/or enzyme assays and western blot analysis of proteins.

Example 12
Expression of INSV S RNA sequences in tobacco plant cells

RNA is extracted from leaves of regenerated plants using the following protocol. Grind 200 mg leaf material to a fine powder in liquid nitrogen. Add 800 μl RNA extraction buffer (100 mM Tris-HCl (pH 8,0), 500 mM NaCl, 2 mM EDTA, 200 mM β-Mercapto-ethanol, 0,4% SDS) and extract the homogenate with phenol, collect the nucleic acids by alcohol precipitation. Resuspend the nucleic acids in 0,5 ml 10 mM Tris-HCl (pH 8,0), 1 mM EDTA, add LiCl to a final concentration of 2M, leave on ice for maximal 4 hours and collect the RNA by centrifugation. Resuspend in 400 μl 10 mM Tris-HCl (pH 8,0), 1 mM EDTA and precipitate with alcohol, finally resuspend in 50 μl 10 mM Tris-HCl (pH 8,0), 1 mM EDTA. RNAs are separated on glyoxal/agarose gels and blotted to Genescreen as described by van Grinsven et al. [(1986) Theor Appl Gen 73:94–101]. INSV S RNA sequences are detected using DNA or RNA probes labeled with [$^{32}$P], [$^{35}$S] or by using non-radioactive labeling techniques. Based on northern analysis, it is determined to what extent the regenerated plants express chimaeric INSV S RNA sequences.

Plants transformed with chimaeric constructs containing an INSV N protein-encoding sequence are also subjected to western blot analysis. Proteins are extracted from leaves of transformed plants by grinding in sample buffer according to the method of Laemmli [(1970) Nature 244:29–30]. A 50 μg portion of protein is subjected to electrophoresis in a 12,5% SDS-polyacrylamide gel essentially as described by Laemmli (1970) supra. Separated proteins are transferred to nitrocellulose electrophoretically as described by Towbin et al. [(1979) Proc. Natl. Acad. Sci. USA 76:4350–4354]. Transferred proteins are reacted with antiserum raised against purified INSV structural or non-structural proteins (Towbin et al. (1979) supra. Based on the results of the western analysis, it is determined that transformed plants do contain INSV N proteins encoded by the inserted chimaeric sequences.

Example 13
Resistance of plants against INSV infection

Transformed plants are grown in the greenhouse under standard quarantine conditions in order to prevent any infections by pathogens. The transformants are self-pollinated and the seeds harvested. Progeny plants are analyzed for segregation of the inserted gene and subsequently infected with INSV by mechanical inoculation. Tissue from plants systemically infected with INSV is ground in 5 volumes of ice-cold inoculation buffer (10 mM phosphate buffer supplemented with 1% $Na_2SO_3$) and rubbed in the presence of carborundum powder on the first two fully extended leafs of approximately 5 weeks old seedlings. Inoculated plants are monitored for symptom development during 3 weeks after inoculation.

Plants containing INSV Related DNA Sequences show reduced susceptibility to INSV infection as exemplified by a delay in symptom development, whereas untransformed control plants show severe systemic INSV symptoms within 7 days after inoculation.

Example 14
Use of synthetic oligonucleotides for diagnostic purposes

RNA is extracted from leaves of suspected plants using the following protocol: grind 1 gram of leaf material, preferentially showing disease symptoms, in 3 ml 100 mM Tris-HCl, 50 mM EDTA, 1.5M NaCl and 2% CTAB (pH 8.0). After grinding, 1 ml of the homogenate is subjected to chloroform extraction and incubated at 65° C. for 10 minutes. The inorganic phase is then collected and extracted with phenol/chloroform (1:1), followed by a last extraction with chloroform. The ribonucleic acids are isolated from the inorganic phase, containing the total nucleic acids, by adding LiCl to a final concentration of 2M. The preparation is incubated at 4° C. for 1 hour, after which the ribonucleic acids are collected by centrifugation. The ribonucleic acid pellet is resuspended in 25 μl 10 mM Tris-HCl, 1 mM EDTA (pH 8.0). The ribonucleic acids are recovered by standard alcohol precipitation. The ribonucleic acid pellet is resuspended in 25 μl 10 mM Tris-HCl, 1 mM EDTA (pH 8.0).

1 μl of the purified ribonucleic acids is spotted on a nylon blotting membrane (e.g. Hybond-N, Amersham UK). The presence of INSV in the plant is detected by standard hybridization, using any part or parts of the sequence isolated from virions or preferentially by designing synthetic oligomers on the basis of disclosed sequence information as a probe. (Alternatively, in vitro transcripts of regions of the INSV genome are used to detect INSV Related RNA Sequences in diseased plants.) A diseased plant is diagnosed by the occurrence of hybridization at the dot containing RNA material from the diseased plant.

We claim:

1. Recombinant Impatiens Necrotic Spot Virus DNA constructs comprising a DNA sequence under expression control of a promoter and a terminator capable of functioning in plants, said DNA sequence encodes an RNA sequence selected from the group consisting of the following sequences:
   i) the S RNA nucleotide sequence from position 1 to position 3001 of SEQ. ID No. 1;
   ii) the S RNA nucleotide sequence from position 1 to position 2993 of SEQ. ID No. 2;
   iii) the S RNA nucleotide sequence from position 1 to position 789 of SEQ. ID No.4;
   iv) the S RNA nucleotide sequence of SEQ ID No. 9 from position 1 to position 3000;
   v) the S RNA nucleotide sequence of SEQ ID No. 10 from position 1 to position 2993;
   vi) the S RNA nucleotide sequence of SEQ ID No. 11 from position 1 to position 789;
   vii) the M RNA nucleotide sequence of SEQ ID No. 14 from position 1 to position 4970;
   viii) the M RNA nucleotide sequence of SEQ ID No. 15 from position 1 to position 912;
   ix) the M RNA nucleotide sequence of SEQ ID No. 20 from position 1 to position 4970;
   x) the M RNA nucleotide sequence of SEQ ID No. 22 from position 1 to position 912; and
   xi) an RNA sequence wherein the codons of said RNA sequence have been replaced by one or more codons which encode the same amino acid as an RNA sequence of i) thru x)
   xii) an RNA sequence complementary to an RNA sequence.

2. The construct according to claim 1, wherein the promoter is a viral, fungal, bacterial, animal or plant derived promoter capable of functioning in plant cells.

3. The construct according to claim 2 wherein the terminator is a viral, fungal, bacterial, animal or plant derived terminator capable of functioning in plant cells.

4. A plant comprising in its genome a DNA construct according to claim 1.

5. A process of preparing a plant comprising in its genome a DNA construct according to claim 1 which comprises:

a) inserting into the genome of a plant cell a DNA construct according to claim 1;
   b) obtaining transformed plant cells; and
   c) regenerating transformed plants from the transformed plant cells wherein said plant has incorporated said DNA construct into its genome.

6. The construct of claim 1, capable of providing plants with resistance to infections by tospoviruses, wherein the DNA sequence encodes an RNA sequence which is complementary to one which when incubated for 16 hours at 42° C. in a buffer system comprising 5 times standard saline citrate, 0.5% sodium dodecyl sulphate, 5 times Denhardts solution, 50% formamide and 100 µg/ml carrier DNA followed by washing 3 times with a buffer system comprising 1 times standard saline citrate and 0.1% sodium dodecylsulphate at 65° C. for one hour each time, still hybridizes with the sequence of i)-xi.

7. The construct of claim 1 wherein the RNA sequence is selected from the group consisting the S RNA nucleotide sequence from position 1 to position 3001 of SEQ. ID No. 1; the S RNA nucleotide sequence from position 1 to position 2993 of SEQ. ID No. 2; and the S RNA nucleotide sequence from position 1 to position 789 of SEQ. ID No.4.

8. The construct of claim 1 wherein the RNA sequence is selected from the group consisting of the S RNA nucleotide sequence of SEQ ID No. 9 from position 1 to position 3000, the S RNA nucleotide sequence of SEQ ID No. 10 from position 1 to position 2993; and the S RNA nucleotide sequence of SEQ ID No. 11 from position 1 to position 789.

9. The construct of claim 1 wherein the RNA sequence is selected from the group consisting of the M RNA nucleotide sequence of SEQ ID No. 14 from position 1 to position 4970 and the M RNA nucleotide sequence of SEQ ID No. 15 from position 1 to position 912.

10. The construct of claim 1 wherein the RNA sequence is selected from the group consisting of the M RNA nucleotide sequence of SEQ ID No. 20 from position 1 to position 4970 and the M RNA nucleotide sequence of SEQ ID No. 22 from position 1 to position 912.

11. The construct according to claim 6 wherein the promoter is a viral, fungal, bacterial, animal or plant derived promoter capable of functioning in plant cells.

12. The construct according to claim 11 wherein the promoter is a plant derived promoter.

13. The construct according to claim 6 wherein the terminator is a viral, fungal, bacterial, animal, or plant derived terminator capable of functioning in plant cells.

14. A plant comprising in its genome a DNA construct according to claim 6.

15. A process of preparing a plant comprising in its genome a DNA construct according to claim 6 which comprises:
   a) inserting into the genome of a plant cell a DNA construct according to claim 6;
   b) obtaining transformed plant cells; and
   c) regenerating transformed plants from the transformed plant cells wherein said transformed plants have incorporated said DNA construct into its genome.

16. The construct of claim 8 wherein the RNA sequence is the S RNA sequence from position 1 to position 789 of SEQ ID No. 11.

17. The construct of claim 10 wherein the RNA sequence is the M RNA sequence from position 1 to position 912 of SEQ ID NO. 22.

* * * * *

UNITED STATES PATENT AND TRADEMARK OFFICE
CERTIFICATE OF CORRECTION

PATENT NO. : 5,773,700
DATED : June 30, 1998
INVENTOR(S) : Martinus Quirinius Joseph Marie Van Grinsven et al It is certified that error appears in the above-identified patent and that said Letters Patent is hereby corrected as shown below:

On the title page: Item [73] Assignee: should read --
Sandoz et al, Switzerland --.

Signed and Sealed this

Second Day of March, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 3001 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
AGAGCAATGA  ACAACCAAGC  TACAACAAAT  CTTACAATAT  TGTCAATTAC  ATTACTACTT      60
CCATTTTAAC  ATGTCTAGTG  CAATGTATGA  AACAATTATC  AAATCGAAGT  CCTCAATCTG     120
GGGAACAACA  TCTTCGGGTA  AAGCAGTAGT  AGATAGTTAT  TGGATTCATG  ATCAATCTTC     180
CGGAAAGAAG  TTGGTCGAAG  CTCAACTCTA  TTCTGACTCC  AGGAGCAAGA  CCAGTTTCTG     240
TTACACTGGT  AAAGTTGGCT  TTCTCCCAAC  AGAAGAAAAA  GAAATTATAG  TGAGATGTTT     300
TGTGCCTATT  TTTGATGACA  TTGATCTGAA  TTTCTCCTTT  TCAGGGAATG  TTGTCGAAAT     360
TCTGGTCAGA  TCTAACACAA  CAAACACAAA  CGGTGTTAAA  CATCAAGGTC  ATCTCAAAGT     420
GTTATCCTCT  CAGTTGCTCA  GAATGCTTGA  AGAGCAAATA  GCAGTGCCTG  AAATTACTTC     480
AAGATTCGGT  CTGAAAGAAT  CTGACATCTT  CCCTCCAAAT  AATTTCATTG  AAGCTGCAAA     540
TAAAGGATCA  TTGTCTTGTG  TCAAAGAAGT  CCTTTTTGAT  GTCAAGTATT  CAAACAACCA     600
ATCCATGGGC  AAAGTCAGTG  TTCTTTCTCC  TACCAGAAGT  GTTCATGAAT  GGCTGTACAC     660
ACTTAAGCCT  GTTTTTAACC  AATCCCAGAC  CAACAACAGG  ACAGTAAACA  CTTTGGCTGT     720
AAAATCACTG  GCAATGTCTG  CAACTTCTGA  TTTAATGTCA  GATACTCATT  CGTTTGTCAG     780
GCTCAATAAT  AACAAGCCTT  TTAAAATCAG  CCTTTGGATG  CGCATCCCTA  AAATAATGAA     840
ATCAAACACA  TACAGCCGGT  TCTTCACCCT  GTCTGATGAA  TCTTCTCCTA  AAGAGTATTA     900
TATAAGCATT  CAATGTCTTC  CGAATCACAA  CAATGTTGAA  ACAGTCATTG  AATATAACTT     960
TGATCAGTCA  AACCTCTTCT  TGAATCAACT  CCTTCTAGCA  GTGATTCATA  AAATTGAGAT    1020
GAATTTTTCT  GATCTAAAAG  AACCTTACAA  TGTTATCCAT  GATATGTCGT  ATCCTCAAAG    1080
AATTGTTCAT  TCACTTCTTG  AAATCCACAC  AGAACTTGCT  CAAACTGTCT  GTGACAGTGT    1140
TCAGCAAGAC  ATGATTGTCT  TCACTATAAA  TGAGCCAGAT  CTAAAGCCAA  AAAAGTTTGA    1200
GCTAGGGAAA  AAGACTTTAA  ATTATTCAGA  AGATGGTTAT  GGGAGAAAAT  ATTTCCTTTC    1260
TCAGACCTTG  AAAAGTCTTC  CGAGAAACTC  ACAAACAATG  TCTTATTTGG  ATAGCATCCA    1320
GATGCCCGAT  TGGAAATTTG  ACTATGCTGC  AGGTGAAATA  AAAATTTCTC  CTAGATCAGA    1380
GGATGTTTTG  AAAGCTATTT  CTAAATTAGA  TTTAAATTAA  CCTTGGTTAA  ACTTGTCCCT    1440
AAGTAAAGTT  TGTTTACATG  CATTTAGATC  AGATTAAACA  AATCTAATAA  CAGATAAACC    1500
AAAAACAATC  ATATGAAATA  AATAAATAAA  CATAAAATAT  ATAAAAAATA  CAAAAAAAAT    1560
CATAAAATAA  ATAAAAACCA  AAAAAGGATG  GCCTTCGGGC  ACAATTTGGT  TGCTTTAATA    1620
ATGCTTTAAA  ATGAATGTAT  TAGTAAATTA  TAAACTTTAA  ATCCAATCTA  CTCACAAATT    1680
```

| | | | | | | |
|---|---|---|---|---|---|---|
| GGCCAAAAAT | TTGTATTTGT | TTTTGTTTTT | GTTTTTTGTT | TTTTGTTTTT | GTTTTGTTTT | 1740 |
| ATTTGTTTTT | TATTTGTTT | TTTGTTTTTT | GTTTTTATT | TTATTTATAT | ATATATATAT | 1800 |
| ATATATTTTG | TAGTGGTTTT | TATTGTTTTT | ATTATTTTTT | GTAGCTTTTT | TACTTGTTTA | 1860 |
| TTTCACACGC | AAACACACTT | TCAAGTTTAT | ATATTAAAAC | ACACATTAAA | CTTATTTCAA | 1920 |
| ATAATTTATA | AAAGCACACT | TAATACACTC | AAACAATAAT | TAATTATTTT | ATTTTTTATT | 1980 |
| TTATTTTTTA | TTTTTATTAT | TTTTATTTTT | ATTTATTTAA | ATGCATTTAA | CACAACACAA | 2040 |
| AGCAAACCAA | GCTCAAATCT | CTTTTAAATA | GAATCATTTT | TCCCAAAATC | AATAGTAGCA | 2100 |
| TTAAACATGC | TGTAAATGGA | TGTAAGCCCT | TCTTTGTAGT | GGTCCATTGC | AGCAAGTCCT | 2160 |
| TTAGCTTTCG | GACTACAAGC | CTTTAGTATA | TCTGCATATT | GTTTAGCCTT | GCCAATTTCA | 2220 |
| ACAGAGTTCA | TGCTATATCC | TTTGCTTTTT | AGAACTGTGC | ACACTTTCCC | AACTGCCTCT | 2280 |
| TTAGTGCTAA | ACTTAGACAT | GTCAATTCCA | AGCTCAACAT | GTTTAGCATC | TTGATAAATA | 2340 |
| GCCGGAACTA | GTGCAGCTAT | TTCAAAATTC | AGTACAGATG | CTATCAGAGG | AAGACTTCCT | 2400 |
| CCTAAGAGAA | CACCCAAGAC | ACAGGATTTC | AAATCTGTGG | TTGCAAGACC | ATATGAGGCA | 2460 |
| ATCAGAGGGT | GACTTGGAAG | GCTATTTATA | GCTTCAGTCA | GAGCAGATCC | ATTGTCCTTT | 2520 |
| ATCATTCCAA | CAAGATGAAC | TCTCACCATT | GCATCAAGTC | TTCGGAAAGT | CATATCATTG | 2580 |
| ACCCCAACTC | TTTCTGAATT | GTTTCTAGTT | TTCTTAATTG | TGACTGATCC | AAAAGTGAAG | 2640 |
| TCAGCACTCT | TAATGACTCT | CATTATAGAT | TGCCTATTCT | TGAGGAAGGA | TAGGCAGGAT | 2700 |
| GCAGTAGTCA | TGTTCTGAAT | CTTTTCACGG | TTGTTGGTAA | AGAAGTCAGT | GAAATTGAAA | 2760 |
| GACCCTTCAT | TTTGAGTTTC | CTCAAATTCT | AAGGAATCAG | ATTGAGTCAA | AAGCTTGACT | 2820 |
| ATGTTCTCCT | TGGTAATCTT | TGCTTTGTTC | ATCTTGATCT | GCTGACTTTA | CTAACTTTAA | 2880 |
| AGCTTAAAGT | GTTCAAATTA | CTAAATAGTA | CTTGCGGTTA | AAGTAGTATT | TGGTAAAATT | 2940 |
| TGTAATTTTT | CAGTTTCTAG | CTTTGGATTA | TATGATGTTA | TATTCGTGAC | ACAATTGCTC | 3000 |
| T | | | | | | 3001 |

(2) INFORMATION FOR SEQ ID NO:2:

(i) SEQUENCE CHARACTERISTICS:
        (A) LENGTH: 2993 base pairs
        (B) TYPE: nucleic acid
        (C) STRANDEDNESS: single
        (D) TOPOLOGY: linear (xi) SEQUENCE DESCRIPTION: SEQ ID NO:2:

| | | | | | | |
|---|---|---|---|---|---|---|
| GAACAACCAA | GCTACAACAA | ATCTTACAAT | ATTGTCAATT | ACATTACTAC | TTCCATTTTA | 60 |
| ACATGTCTAG | TGCAATGTAT | GAAACAATTA | TCAAATCGAA | GTCCTCAATC | TGGGGAACAA | 120 |
| CATCTTCGGG | TAAAGCAGTA | GTAGATAGTT | ATTGGATTCA | TGATCAATCT | TCCGGAAAGA | 180 |
| AGTTGGTCGA | AGCTCAACTC | TATTCTGACT | CCAGGAGCAA | GACCAGTTTC | TGTTACACTG | 240 |
| GTAAAGTTGG | CTTTCTCCCA | ACAGAAGAAA | AAGAAATTAT | AGTGAGATGT | TTTGTGCCTA | 300 |
| TTTTTGATGA | CATTGATCTG | AATTTCTCCT | TTTCAGGGAA | TGTTGTCGAA | ATTCTGGTCA | 360 |
| GATCTAACAC | AACAAACACA | AACGGTGTTA | AACATCAAGG | TCATCTCAAA | GTGTTATCCT | 420 |
| CTCAGTTGCT | CAGAATGCTT | GAAGAGCAAA | TAGCAGTGCC | TGAAATTACT | TCAAGATTCG | 480 |
| GTCTGAAAGA | ATCTGACATC | TTCCCTCCAA | ATAATTTCAT | TGAAGCTGCA | AATAAAGGAT | 540 |
| CATTGTCTTG | TGTCAAAGAA | GTCCTTTTTG | ATGTCAAGTA | TTCAAACAAC | CAATCCATGG | 600 |
| GCAAAGTCAG | TGTTCTTTCT | CCTACCAGAA | GTGTTCATGA | ATGGCTGTAC | ACACTTAAGC | 660 |
| CTGTTTTTAA | CCAATCCCAG | ACCAACAACA | GGACAGTAAA | CACTTTGGCT | GTAAAATCAC | 720 |

| | | | | | |
|---|---|---|---|---|---|
| TGGCAATGTC | TGCAACTTCT | GATTTAATGT | CAGATACTCA | TTCGTTTGTC | AGGCTCAATA | 780
| ATAACAAGCC | TTTTAAAATC | AGCCTTTGGA | TGCGCATCCC | TAAAATAATG | AAATCAAACA | 840
| CATACAGCCG | GTTCTTCACC | CTGTCTGATG | AATCTTCTCC | TAAAGAGTAT | TATATAAGCA | 900
| TTCAATGTCT | TCCGAATCAC | AACAATGTTG | AAACAGTCAT | TGAATATAAC | TTTGATCAGT | 960
| CAAACCTCTT | CTTGAATCAA | CTCCTTCTAG | CAGTGATTCA | TAAAATTGAG | ATGAATTTTT | 1020
| CTGATCTAAA | AGAACCTTAC | AATGTTATCC | ATGATATGTC | GTATCCTCAA | AGAATTGTTC | 1080
| ATTCACTTCT | TGAAATCCAC | ACAGAACTTG | CTCAAACTGT | CTGTGACAGT | GTTCAGCAAG | 1140
| ACATGATTGT | CTTCACTATA | AATGAGCCAG | ATCTAAAGCC | AAAAAGTTT | GAGCTAGGGA | 1200
| AAAAGACTTT | AAATTATTCA | GAAGATGGTT | ATGGGAGAAA | ATATTCCTT | TCTCAGACCT | 1260
| TGAAAGTCT | TCCGAGAAAC | TCACAAACAA | TGTCTTATTT | GGATAGCATC | CAGATGCCCG | 1320
| ATTGGAAATT | TGACTATGCT | GCAGGTGAAA | TAAAATTTC | TCCTAGATCA | GAGGATGTTT | 1380
| TGAAAGCTAT | TTCTAAATTA | GATTTAAATT | AACCTTGGTT | AAACTTGTCC | CTAAGTAAAG | 1440
| TTTGTTTACA | TGCATTTAGA | TCAGATTAAA | CAAATCTAAT | AACAGATAAA | CCAAAAACAA | 1500
| TCATATGAAA | TAAATAAATA | AACATAAAAT | ATATAAAAAA | TACAAAAAAA | ATCATAAAAT | 1560
| AAATAAAAAC | CAAAAAGGA | TGGCCTTCGG | GCACAATTTG | GTTGCTTTAA | TAATGCTTTA | 1620
| AAATGAATGT | ATTAGTAAAT | TATAAACTTT | AAATCCAATC | TACTCACAAA | TTGGCCAAAA | 1680
| ATTTGTATTT | GTTTTTGTTT | TTGTTTTTTG | TTTTTGTTT | TTGTTTGTT | TTATTTGTTT | 1740
| TTTATTTTGT | TTTTTGTTTT | TTGTTTTTA | TTTTATTTAT | ATATATATAT | ATATATATTT | 1800
| TGTAGTGGTT | TTTATTGTTT | TTATTATTTT | TTGTAGCTTT | TTTACTTGTT | TATTTCACAC | 1860
| GCAAACACAC | TTTCAAGTTT | ATATATTAAA | ACACACATTA | AACTTATTTC | AAATAATTTA | 1920
| TAAAAGCACA | CTTAATACAC | TCAAACAATA | ATTAATTATT | TTATTTTTA | TTTTATTTTT | 1980
| TATTTTTATT | ATTTTTATTT | TTATTTATTT | AAATGCATTT | AACACAACAC | AAAGCAAACC | 2040
| AAGCTCAAAT | CTCTTTTAAA | TAGAATCATT | TTTCCCAAAA | TCAATAGTAG | CATTAAACAT | 2100
| GCTGTAAATG | GATGTAAGCC | CTTCTTTGTA | GTGGTCCATT | GCAGCAAGTC | CTTTAGCTTT | 2160
| CGGACTACAA | GCCTTTAGTA | TATCTGCATA | TTGTTTAGCC | TTGCCAATTT | CAACAGAGTT | 2220
| CATGCTATAT | CCTTTGCTTT | TTAGAACTGT | GCACACTTTC | CCAACTGCCT | CTTTAGTGCT | 2280
| AAACTTAGAC | ATGTCAATTC | CAAGCTCAAC | ATGTTTAGCA | TCTTGATAAA | TAGCCGGAAC | 2340
| TAGTGCAGCT | ATTTCAAAAT | TCAGTACAGA | TGCTATCAGA | GGAAGACTTC | CTCCTAAGAG | 2400
| AACACCCAAG | ACACAGGATT | TCAAATCTGT | GGTTGCAAGA | CCATATGAGG | CAATCAGAGG | 2460
| GTGACTTGGA | AGGCTATTTA | TAGCTTCAGT | CAGAGCAGAT | CCATTGTCCT | TTATCATTCC | 2520
| AACAAGATGA | ACTCTCACCA | TTGCATCAAG | TCTTCGGAAA | GTCATATCAT | TGACCCCAAC | 2580
| TCTTTCTGAA | TTGTTTCTAG | TTTTCTTAAT | TGTGACTGAT | CCAAAAGTGA | AGTCAGCACT | 2640
| CTTAATGACT | CTCATTATAG | ATTGCCTATT | CTTGAGGAAG | GATAGGCAGG | ATGCAGTAGT | 2700
| CATGTTCTGA | ATCTTTTCAC | GGTTGTTGGT | AAAGAAGTCA | GTGAAATTGA | AAGACCCTTC | 2760
| ATTTGAGTT | TCCTCAAATT | CTAAGGAATC | AGATTGAGTC | AAAAGCTTGA | CTATGTTCTC | 2820
| CTTGGTAATC | TTTGCTTTGT | TCATCTTGAT | CTGCTGACTT | TACTAACTTT | AAAGCTTAAA | 2880
| GTGTTCAAAT | TACTAAATAG | TACTTGCGGT | TAAAGTAGTA | TTTGGTAAAA | TTTGTAATTT | 2940
| TTCAGTTTCT | AGCTTTGGAT | TATATGATGT | TATATTCGTG | ACACAATTGC | TCT | 2993

( 2 ) INFORMATION FOR SEQ ID NO:3:

( i ) SEQUENCE CHARACTERISTICS:
  ( A ) LENGTH: 1350 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:3:

| | | | | | |
|---|---|---|---|---|---|
| ATGTCTAGTG | CAATGTATGA | AACAATTATC | AAATCGAAGT | CCTCAATCTG | GGGAACAACA | 60 |
| TCTTCGGGTA | AAGCAGTAGT | AGATAGTTAT | TGGATTCATG | ATCAATCTTC | CGGAAAGAAG | 120 |
| TTGGTCGAAG | CTCAACTCTA | TTCTGACTCC | AGGAGCAAGA | CCAGTTTCTG | TTACACTGGT | 180 |
| AAAGTTGGCT | TTCTCCCAAC | AGAAGAAAAA | GAAATTATAG | TGAGATGTTT | TGTGCCTATT | 240 |
| TTTGATGACA | TTGATCTGAA | TTTCTCCTTT | TCAGGGAATG | TTGTCGAAAT | TCTGGTCAGA | 300 |
| TCTAACACAA | CAAACACAAA | CGGTGTTAAA | CATCAAGGTC | ATCTCAAAGT | GTTATCCTCT | 360 |
| CAGTTGCTCA | GAATGCTTGA | AGAGCAAATA | GCAGTGCCTG | AAATTACTTC | AAGATTCGGT | 420 |
| CTGAAAGAAT | CTGACATCTT | CCCTCCAAAT | AATTTCATTG | AAGCTGCAAA | TAAAGGATCA | 480 |
| TTGTCTTGTG | TCAAAGAAGT | CCTTTTTGAT | GTCAAGTATT | CAAACAACCA | ATCCATGGGC | 540 |
| AAAGTCAGTG | TTCTTTCTCC | TACCAGAAGT | GTTCATGAAT | GGCTGTACAC | ACTTAAGCCT | 600 |
| GTTTTTAACC | AATCCCAGAC | CAACAACAGG | ACAGTAAACA | CTTTGGCTGT | AAAATCACTG | 660 |
| GCAATGTCTG | CAACTTCTGA | TTTAATGTCA | GATACTCATT | CGTTTGTCAG | GCTCAATAAT | 720 |
| AACAAGCCTT | TTAAAATCAG | CCTTTGGATG | CGCATCCCTA | AATAATGAA | ATCAAACACA | 780 |
| TACAGCCGGT | TCTTCACCCT | GTCTGATGAA | TCTTCTCCTA | AGAGTATTA | TATAAGCATT | 840 |
| CAATGTCTTC | CGAATCACAA | CAATGTTGAA | ACAGTCATTG | AATATAACTT | TGATCAGTCA | 900 |
| AACCTCTTCT | TGAATCAACT | CCTTCTAGCA | GTGATTCATA | AAATTGAGAT | GAATTTTTCT | 960 |
| GATCTAAAAG | AACCTTACAA | TGTTATCCAT | GATATGTCGT | ATCCTCAAAG | AATTGTTCAT | 1020 |
| TCACTTCTTG | AAATCCACAC | AGAACTTGCT | CAAACTGTCT | GTGACAGTGT | TCAGCAAGAC | 1080 |
| ATGATTGTCT | TCACTATAAA | TGAGCCAGAT | CTAAAGCCAA | AAAAGTTTGA | GCTAGGGAAA | 1140 |
| AAGACTTTAA | ATTATTCAGA | AGATGGTTAT | GGGAGAAAAT | ATTTCCTTTC | TCAGACCTTG | 1200 |
| AAAAGTCTTC | CGAGAAACTC | ACAAACAATG | TCTTATTTGG | ATAGCATCCA | GATGCCCGAT | 1260 |
| TGGAAATTTG | ACTATGCTGC | AGGTGAAATA | AAAATTTCTC | CTAGATCAGA | GGATGTTTTG | 1320 |
| AAAGCTATTT | CTAAATTAGA | TTTAAATTAA | | | | 1350 |

( 2 ) INFORMATION FOR SEQ ID NO:4:

( i ) SEQUENCE CHARACTERISTICS:
    ( A ) LENGTH: 789 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

| | | | | | |
|---|---|---|---|---|---|
| TTAAATAGAA | TCATTTTTCC | CAAAATCAAT | AGTAGCATTA | AACATGCTGT | AAATGGATGT | 60 |
| AAGCCCTTCT | TTGTAGTGGT | CCATTGCAGC | AAGTCCTTTA | GCTTCGGAC | TACAAGCCTT | 120 |
| TAGTATATCT | GCATATTGTT | TAGCCTTGCC | AATTTCAACA | GAGTTCATGC | TATATCCTTT | 180 |
| GCTTTTTAGA | ACTGTGCACA | CTTTCCCAAC | TGCCTCTTTA | GTGCTAAACT | TAGACATGTC | 240 |
| AATTCCAAGC | TCAACATGTT | TAGCATCTTG | ATAAATAGCC | GGAACTAGTG | CAGCTATTTC | 300 |
| AAAATTCAGT | ACAGATGCTA | TCAGAGGAAG | ACTTCCTCCT | AAGAGAACAC | CCAAGACACA | 360 |
| GGATTTCAAA | TCTGTGGTTG | CAAGACCATA | TGAGGCAATC | AGAGGGTGAC | TTGGAAGGCT | 420 |
| ATTTATAGCT | TCAGTCAGAG | CAGATCCATT | GTCCTTTATC | ATTCCAACAA | GATGAACTCT | 480 |

| | | | | | |
|---|---|---|---|---|---|
| CACCATTGCA | TCAAGTCTTC | GGAAAGTCAT | ATCATTGACC | CCAACTCTTT | CTGAATTGTT | 540 |
| TCTAGTTTTC | TTAATTGTGA | CTGATCCAAA | AGTGAAGTCA | GCACTCTTAA | TGACTCTCAT | 600 |
| TATAGATTGC | CTATTCTTGA | GGAAGGATAG | GCAGGATGCA | GTAGTCATGT | TCTGAATCTT | 660 |
| TTCACGGTTG | TTGGTAAAGA | AGTCAGTGAA | ATTGAAAGAC | CCTTCATTTT | GAGTTTCCTC | 720 |
| AAATTCTAAG | GAATCAGATT | GAGTCAAAAG | CTTGACTATG | TTCTCCTTGG | TAATCTTTGC | 780 |
| TTTGTTCAT | | | | | | 789 |

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

AGAGCAATGA ACAACCCAAG C                                      21

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:6:

GATTATATGA TGTTATATTC GTGACACAAT TGCTCT                      36

(2) INFORMATION FOR SEQ ID NO:7:

(i) SEQUENCE CHARACTERISTICS:
        (A) LENGTH: 643 base pairs
        (B) TYPE: nucleic acid
        (C) STRANDEDNESS: single
        (D) TOPOLOGY: linear (xi) SEQUENCE DESCRIPTION: SEQ ID NO:7:

| | | | | | |
|---|---|---|---|---|---|
| CCTTGGTTAA | ACTTGTCCCT | AAGTAAAGTT | TGTTTACATG | CATTTAGATC | AGATTAAACA | 60 |
| AATCTAATAA | CAGATAAACC | AAAAACAATC | ATATGAAATA | AATAAATAAA | CATAAAATAT | 120 |
| ATAAAAAATA | CAAAAAAAAT | CATAAAATAA | ATAAAAACCA | AAAAAGGATG | GCCTTCGGGC | 180 |
| ACAATTTGGT | TGCTTTAATA | ATGCTTTAAA | ATGAATGTAT | TAGTAAATTA | TAAACTTTAA | 240 |
| ATCCAATCTA | CTCACAAATT | GGCCAAAAAT | TTGTATTTGT | TTTTGTTTTT | GTTTTTGTT | 300 |
| TTTTGTTTTT | GTTTTGTTTT | ATTTGTTTTT | TATTTTGTTT | TTTGTTTTTT | GTTTTTATT | 360 |
| TTATTTATAT | ATATATATAT | ATATATTTTG | TAGTGGTTTT | TATTGTTTTT | ATTATTTTT | 420 |
| GTAGCTTTTT | TACTTGTTTA | TTTCACACGC | AAACACACTT | TCAAGTTTAT | ATATTAAAAC | 480 |
| ACACATTAAA | CTTATTTCAA | ATAATTTATA | AAAGCACACT | TAATACACTC | AAACAATAAT | 540 |
| TAATTATTTT | ATTTTTATT | TTATTTTTA | TTTTTATTAT | TTTTATTTTT | ATTTATTTAA | 600 |
| ATGCATTTAA | CACAACACAA | AGCAAACCAA | GCTCAAATCT | CTT | | 643 |

(2) INFORMATION FOR SEQ ID NO:8:

(i) SEQUENCE CHARACTERISTICS:
        (A) LENGTH: 602 base pairs
        (B) TYPE: nucleic acid
        (C) STRANDEDNESS: single
        (D) TOPOLOGY: linear ( x i ) SEQUENCE DESCRIPTION: SEQ ID NO:8:

| | | | | | | |
|---|---|---|---|---|---|---|
| TGGTTAAACT | TGTCCCTAAG | TAAAGTTTGT | TTACATGCAT | TTAGATCAGA | TTAAACAAAT | 60 |
| CTAATAACAG | ATAAACCAAA | AACAATCATA | TGAAATAAAT | AAATAAACAT | AAAATATATA | 120 |
| AAAATACAA | AAAAAATCAT | AAAATAAATA | AAAACCAAAA | AAGGATGGCC | TTCGGGCACA | 180 |
| ATTTGGTTGC | TTTAATAATG | CTTTAAAATG | AATGTATTAG | TAAATTATAA | ACTTTAAATC | 240 |
| CAATCTACTC | ACAAATTGGC | CAAAAATTTG | TATTTGTTTT | TGTTTTTGTT | TTTTGTTTTT | 300 |
| TGTTTTTGTT | TTGTTTTATT | TGTTTTTTAT | TTTGTTTTTT | GTTTTTTGTT | TTTTATTTTA | 360 |
| TTTATATATA | TATATATATA | TATTTTGTAG | TGGTTTTTAT | TGTTTTTATT | ATTTTTTGTA | 420 |
| GCTTTTTTAC | TTGTTTATTT | CACACGCAAA | CACACTTTCA | AGTTTATATA | TTAAAACACA | 480 |
| CATTAAACTT | ATTTCAAATA | ATTTATAAAA | GCACACTTAA | TACACTCAAA | CAATAATTAA | 540 |
| TTATTTTATT | TTTTATTTTA | TTTTTTATTT | TTATTATTTT | TATTTTTATT | TATTTAAATG | 600 |
| CA | | | | | | 602 |

( 2 ) INFORMATION FOR SEQ ID NO:9:

( i ) SEQUENCE CHARACTERISTICS:
        ( A ) LENGTH: 3000 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

| | | | | | | |
|---|---|---|---|---|---|---|
| AGAGCAATTG | TGTCACGAAT | ATAACATCAT | ATAATCCAAA | GCTAGAAACT | GAAAAATTAC | 60 |
| AAATTTTACC | AAATACTACT | TTAACCGCAA | GTACTATTTA | GTAATTTGAA | CACTTTAAGC | 120 |
| TTTAAAGTTA | GTAAAGTCAG | CAGATCAAGA | TGAACAAAGC | AAAGATTACC | AAGGAGAACA | 180 |
| TAGTCAAGCT | TTTGACTCAA | TCTGATTCCT | TAGAATTTGA | GGAAACTCAA | AATGAAGGGT | 240 |
| CTTTCAATTT | CACTGACTTC | TTTACCAACA | ACCGTGAAAA | GATTCAGAAC | ATGACTACTG | 300 |
| CATCCTGCCT | ATCCTTCCTC | AAGAATAGGC | AATCTATAAT | GAGAGTCATT | AAGAGTGCTG | 360 |
| ACTTCACTTT | TGGATCAGTC | ACAATTAAGA | AAACTAGAAA | CAATTCAGAA | AGAGTTGGGG | 420 |
| TCAATGATAT | GACTTTCCGA | AGACTTGATG | CAATGGTGAG | AGTTCATCTT | GTTGGAATGA | 480 |
| TAAAGGACAA | TGGATCTGCT | CTGACTGAAG | CTATAAATAG | CCTTCCAAGT | CACCCTCTGA | 540 |
| TTGCCTCATA | TGGTCTTGCA | ACCACAGATT | TGAAATCCTG | TGTCTTGGGT | GTTCTCTTAG | 600 |
| GAGGAAGTCT | TCCTCTGATA | GCATCTGTAC | TGAATTTTGA | AATAGCTGCA | CTAGTTCCGG | 660 |
| CTATTTATCA | AGATGCTAAA | CATGTTGAGC | TTGGAATTGA | CATGTCTAAG | TTTAGCACTA | 720 |
| AAGAGGCAGT | TGGGAAAGTG | TGCACAGTTC | TAAAAAGCAA | AGGATATAGC | ATGAACTCTG | 780 |
| TTGAAATTGG | CAAGGCTAAA | CAATATGCAG | ATATACTAAA | GGCTTGTAGT | CCGAAAGCTA | 840 |
| AAGGACTTGC | TGCAATGGAC | CACTACAAAG | AAGGGCTTAC | ATCCATTTAC | AGCATGTTTA | 900 |
| ATGCTACTAT | TGATTTTGGG | AAAAATGATT | CTATTTAAAA | GAGATTTGAG | CTTGGTTTGC | 960 |
| TTTGTGTTGT | GTTAAATGCA | TTTAAATAAA | TAAAAATAAA | AATAATAAAA | ATAAAAAATA | 1020 |
| AAATAAAAAA | TAAAATAATT | AATTATTGTT | TGAGTGTATT | AAGTGTGCTT | TTATAAATTA | 1080 |
| TTTGAAATAA | GTTAATGTG | TGTTTTAATA | TATAAACTTG | AAAGTGTGTT | TGCGTGTGAA | 1140 |
| ATAAACAAGT | AAAAAAGCTA | CAAAAAATAA | TAAAAACAAT | AAAAACCACT | ACAAAATATA | 1200 |
| TATATATATA | TATATAAATA | AAATAAAAAA | CAAAAACAA | AAAACAAAAT | AAAAAACAAA | 1260 |
| TAAAACAAAA | CAAAAACAAA | AAACAAAAAA | CAAAAACAAA | AACAAATACA | AATTTTTGGC | 1320 |

| | | | | | |
|---|---|---|---|---|---|
| CAATTTGTGA | GTAGATTGGA | TTTAAAGTTT | ATAATTTACT | AATACATTCT | TTTAAAGCAT | 1380 |
| TATTAAAGCA | ACCAAATTGT | GCCCGAAGGC | CATCCTTTTT | TGGTTTTTAT | TTATTTTATG | 1440 |
| ATTTTTTTTG | TATTTTTTAT | ATATTTTATG | TTTATTTATT | TATTTCATAT | GATTGTTTTT | 1500 |
| GGTTTATCTG | TTATTAGATT | TGTTTAATCT | GATCTAAATG | CATGTAAACA | AACTTTACTT | 1560 |
| AGGGACAAGT | TTAACCAAGG | TTAATTTAAA | TCTAATTTAG | AAATAGCTTT | CAAAACATCC | 1620 |
| TCTGATCTAG | GAGAAATTTT | TATTTCACCT | GCAGCATAGT | CAAATTTCCA | ATCGGGCATC | 1680 |
| TGGATGCTAT | CCAAATAAGA | CATTGTTTGT | GAGTTTCTCG | GAAGACTTTT | CAAGGTCTGA | 1740 |
| GAAAGGAAAT | ATTTTCTCCC | ATAACCATCT | TCTGAATAAT | TTAAAGTCTT | TTTCCCTAGC | 1800 |
| TCAAACTTTT | TTGGCTTTAG | ATCTGGCTCA | TTTATAGTGA | AGACAATCAT | GTCTTGCTGA | 1860 |
| ACACTGTCAC | AGACAGTTTG | AGCAAGTTCT | GTGTGGATTT | CAAGAAGTGA | ATGAACAATT | 1920 |
| CTTTGAGGAT | ACGACATATC | ATGGATAACA | TTGTAAGGTT | CTTTTAGATC | AGAAAAATTC | 1980 |
| ATCTCAATTT | TATGAATCAC | TGCTAGAAGG | AGTTGATTCA | AGAAGAGGTT | TGACTGATCA | 2040 |
| AAGTTATATT | CAATGACTGT | TTCAACATTG | TTGTGATTCG | GAAGACATTG | AATGCTTATA | 2100 |
| TAATACTCTT | TAGGAGAAGA | TTCATCAGAC | AGGGTGAAGA | ACCGGCTGTA | TGTGTTTGAT | 2160 |
| TTCATTATTT | TAGGGATGCG | CATCCAAAGG | CTGATTTTAA | AAGGCTTGTT | ATTATTGAGC | 2220 |
| CTGACAAACG | AATGAGTATC | TGACATTAAA | TCAGAAGTTG | CAGACATTGC | CAGTGATTTT | 2280 |
| ACAGCCAAAG | TGTTTACTGT | CCTGTTGTTG | GTCTGGGATT | GGTTAAAAAC | AGGCTTAAGT | 2340 |
| GTGTACAGCC | ATTCATGAAC | ACTTCTGGTA | GGAGAAAGAA | CACTGACTTT | GCCCATGGAT | 2400 |
| TGGTTGTTTG | AATACTTGAC | ATCAAAAGG | ACTTCTTTGA | CACAAGACAA | TGATCCTTTA | 2460 |
| TTTGCAGCTT | CAATGAAATT | ATTTGGAGGG | AAGATGTCAG | ATTCTTTCAG | ACCGAATCTT | 2520 |
| GAAGTAATTT | CAGGCACTGC | TATTTGCTCT | TCAAGCATTC | TGAGCAACTG | AGAGGATAAC | 2580 |
| ACTTTGAGAT | GACCTTGATG | TTAACACCG | TTTGTGTTTG | TTGTGTTAGA | TCTGACCAGA | 2640 |
| ATTTCGACAA | CATTCCCTGA | AAAGGAGAAA | TTCAGATCAA | TGTCATCAAA | AATAGGCACA | 2700 |
| AAACATCTCA | CTATAATTTC | TTTTTCTTCT | GTTGGGAGAA | AGCCAACTTT | ACCAGTGTAA | 2760 |
| CAGAAACTGG | TCTTGCTCCT | GGAGTCAGAA | TAGAGTTGAG | CTTCGACCAA | CTTCTTTCCG | 2820 |
| GAAGATTGAT | CATGAATCCA | ATAACTATCT | ACTACTGCTT | TACCCGAAGA | TGTTGTTCCC | 2880 |
| CAGATTGAGG | ACTTCGATTT | GATAATTGTT | TCATACATTG | CACTAGACAT | GTTAAAATGG | 2940 |
| AAGTAGTAAT | GTAATTGACA | ATATTGTAAG | ATTTGTTGTA | GCTTGGTTGT | TCATTGCTCT | 3000 |

( 2 ) INFORMATION FOR SEQ ID NO:10:

( i ) SEQUENCE CHARACTERISTICS:
        ( A ) LENGTH: 2993 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | | | | | |
|---|---|---|---|---|---|
| AGAGCAATTG | TGTCACGAAT | ATAACATCAT | ATAATCCAAA | GCTAGAAACT | GAAAAATTAC | 60 |
| AAATTTTACC | AAATACTACT | TTAACCGCAA | GTACTATTTA | GTAATTTGAA | CACTTTAAGC | 120 |
| TTTAAAGTTA | GTAAAGTCAG | CAGATCAAGA | TGAACAAAGC | AAAGATTACC | AAGGAGAACA | 180 |
| TAGTCAAGCT | TTTGACTCAA | TCTGATTCCT | TAGAATTTGA | GGAAACTCAA | AATGAAGGGT | 240 |
| CTTTCAATTT | CACTGACTTC | TTTACCAACA | ACCGTGAAAA | GATTCAGAAC | ATGACTACTG | 300 |
| CATCCTGCCT | ATCCTTCCTC | AAGAATAGGC | AATCTATAAT | GAGAGTCATT | AAGAGTGCTG | 360 |
| ACTTCACTTT | TGGATCAGTC | ACAATTAAGA | AAACTAGAAA | CAATTCAGAA | AGAGTTGGGG | 420 |

| | | | | | |
|---|---|---|---|---|---|
| TCAATGATAT | GACTTTCCGA | AGACTTGATG | CAATGGTGAG | AGTTCATCTT | GTTGGAATGA | 480 |
| TAAAGGACAA | TGGATCTGCT | CTGACTGAAG | CTATAAATAG | CCTTCCAAGT | CACCCTCTGA | 540 |
| TTGCCTCATA | TGGTCTTGCA | ACCACAGATT | TGAAATCCTG | TGTCTTGGGT | GTTCTCTTAG | 600 |
| GAGGAAGTCT | TCCTCTGATA | GCATCTGTAC | TGAATTTTGA | AATAGCTGCA | CTAGTTCCGG | 660 |
| CTATTTATCA | AGATGCTAAA | CATGTTGAGC | TTGGAATTGA | CATGTCTAAG | TTAGCACTA | 720 |
| AAGAGGCAGT | TGGGAAAGTG | TGCACAGTTC | TAAAAAGCAA | AGGATATAGC | ATGAACTCTG | 780 |
| TTGAAATTGG | CAAGGCTAAA | CAATATGCAG | ATATACTAAA | GGCTTGTAGT | CCGAAAGCTA | 840 |
| AAGGACTTGC | TGCAATGGAC | CACTACAAAG | AAGGGCTTAC | ATCCATTTAC | AGCATGTTTA | 900 |
| ATGCTACTAT | TGATTTTGGG | AAAAATGATT | CTATTTAAAA | GAGATTTGAG | CTTGGTTTGC | 960 |
| TTTGTGTTGT | GTTAAATGCA | TTTAAATAAA | TAAAATAAA | AATAATAAAA | ATAAAAAATA | 1020 |
| AAATAAAAAA | TAAAATAATT | AATTATTGTT | TGAGTGTATT | AAGTGTGCTT | TTATAAATTA | 1080 |
| TTTGAAATAA | GTTAATGTG | TGTTTTAATA | TATAAACTTG | AAAGTGTGTT | TGCGTGTGAA | 1140 |
| ATAAACAAGT | AAAAAAGCTA | CAAAAAATAA | TAAAAACAAT | AAAAACCACT | ACAAAATATA | 1200 |
| TATATATATA | TATATAAATA | AAATAAAAAA | CAAAAAACAA | AAAACAAAAT | AAAAAACAAA | 1260 |
| TAAAACAAAA | CAAAACAAAA | AAACAAAAAA | CAAAACAAA | AACAAATACA | AATTTTTGGC | 1320 |
| CAATTTGTGA | GTAGATTGGA | TTTAAAGTTT | ATAATTTACT | AATACATTCA | TTTTAAAGCA | 1380 |
| TTATTAAAGC | AACCAAATTG | TGCCCGAAGG | CCATCCTTTT | TTGGTTTTTA | TTTATTTTAT | 1440 |
| GATTTTTTTT | GTATTTTTTA | TATATTTTAT | GTTTATTTAT | TTATTTCATA | TGATTGTTTT | 1500 |
| TGGTTTATCT | GTTATTAGAT | TTGTTTAATC | TGATCTAAAT | GCATGTAAAC | AAACTTTACT | 1560 |
| TAGGGACAAG | TTTAACCAAG | GTTAATTTAA | ATCAATTTA | GAAATAGCTT | TCAAAACATC | 1620 |
| CTCTGATCTA | GGAGAAATTT | TTATTTCACC | TGCAGCATAG | TCAAATTTCC | AATCGGGCAT | 1680 |
| CTGGATGCTA | TCCAAATAAG | ACATTGTTTG | TGAGTTTCTC | GGAAGACTTT | TCAAGGTCTG | 1740 |
| AGAAAGGAAA | TATTTTCTCC | CATAACCATC | TTCTGAATAA | TTTAAAGTCT | TTTTCCCTAG | 1800 |
| CTCAAACTTT | TTTGGCTTTA | GATCTGGCTC | ATTTATAGTG | AAGACAATCA | TGTCTTGCTG | 1860 |
| AACACTGTCA | CAGACAGTTT | GAGCAAGTTC | TGTGTGGATT | TCAAGAAGTG | AATGAACAAT | 1920 |
| TCTTTGAGGA | TACGACATAT | CATGGATAAC | ATTGTAAGGT | TCTTTTAGAT | CAGAAAAATT | 1980 |
| CATCTCAATT | TTATGAATCA | CTGCTAGAAG | GAGTTGATTC | AAGAAGAGGT | TTGACTGATC | 2040 |
| AAAGTTATAT | TCAATGACTG | TTTCAACATT | GTTGTGATTC | GGAAGACATT | GAATGCTTAT | 2100 |
| ATAATACTCT | TTAGGAGAAG | ATTCATCAGA | CAGGGTGAAG | AACCGGCTGT | ATGTGTTTGA | 2160 |
| TTTCATTATT | TTAGGGATGC | GCATCCAAAG | GCTGATTTTA | AAAGGCTTGT | TATTATTGAG | 2220 |
| CCTGACAAAC | GAATGAGTAT | CTGACATTAA | ATCAGAAGTT | GCAGACATTG | CCAGTGATTT | 2280 |
| TACAGCCAAA | GTGTTTACTG | TCCTGTTGTT | GGTCTGGGAT | TGGTTAAAAA | CAGGCTTAAG | 2340 |
| TGTGTACAGC | CATTCATGAA | CACTTCTGGT | AGGAGAAAGA | ACACTGACTT | TGCCCATGGA | 2400 |
| TTGGTTGTTT | GAATACTTGA | CATCAAAAAG | GACTTCTTTG | ACACAAGACA | ATGATCCTTT | 2460 |
| ATTTGCAGCT | TCAATGAAAT | TATTTGGAGG | GAAGATGTCA | GATTCTTTCA | GACCGAATCT | 2520 |
| TGAAGTAATT | TCAGGCACTG | CTATTTGCTC | TTCAAGCATT | CTGAGCAACT | GAGAGGATAA | 2580 |
| CACTTTGAGA | TGACCTTGAT | GTTAACACC | GTTTGTGTTT | GTTGTGTTAG | ATCTGACCAG | 2640 |
| AATTTCGACA | ACATTCCCTG | AAAAGGAGAA | ATTCAGATCA | ATGTCATCAA | AAATAGGCAC | 2700 |
| AAAACATCTC | ACTATAATTT | CTTTTTCTTC | TGTTGGGAGA | AAGCCAACTT | TACCAGTGTA | 2760 |
| ACAGAAACTG | GTCTTGCTCC | TGGAGTCAGA | ATAGAGTTGA | GCTTCGACCA | ACTTCTTTCC | 2820 |

| | | | | | |
|---|---|---|---|---|---|
| GGAAGATTGA | TCATGAATCC | AATAACTATC | TACTACTGCT | TTACCCGAAG | ATGTTGTTCC | 2880 |
| CCAGATTGAG | GACTTCGATT | TGATAATTGT | TTCATACATT | GCACTAGACA | TGTTAAAATG | 2940 |
| GAAGTAGTAA | TGTAATTGAC | AATATTGTAA | GATTTGTTGT | AGCTTGGTTG | TTC | 2993 |

( 2 ) INFORMATION FOR SEQ ID NO:11:

( i ) SEQUENCE CHARACTERISTICS:
        ( A ) LENGTH: 789 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| | | | | | |
|---|---|---|---|---|---|
| ATGAACAAAG | CAAAGATTAC | CAAGGAGAAC | ATAGTCAAGC | TTTTGACTCA | ATCTGATTCC | 60 |
| TTAGAATTTG | AGGAAACTCA | AAATGAAGGG | TCTTTCAATT | TCACTGACTT | CTTTACCAAC | 120 |
| AACCGTGAAA | AGATTCAGAA | CATGACTACT | GCATCCTGCC | TATCCTTCCT | CAAGAATAGG | 180 |
| CAATCTATAA | TGAGAGTCAT | TAAGAGTGCT | GACTTCACTT | TTGGATCAGT | CACAATTAAG | 240 |
| AAAACTAGAA | ACAATTCAGA | AAGAGTTGGG | GTCAATGATA | TGACTTTCCG | AAGACTTGAT | 300 |
| GCAATGGTGA | GAGTTCATCT | TGTTGGAATG | ATAAAGGACA | ATGGATCTGC | TCTGACTGAA | 360 |
| GCTATAAATA | GCCTTCCAAG | TCACCCTCTG | ATTGCCTCAT | ATGGTCTTGC | AACCACAGAT | 420 |
| TTGAAATCCT | GTGTCTTGGG | TGTTCTCTTA | GGAGGAAGTC | TTCCTCTGAT | AGCATCTGTA | 480 |
| CTGAATTTTG | AAATAGCTGC | ACTAGTTCCG | GCTATTTATC | AAGATGCTAA | ACATGTTGAG | 540 |
| CTTGGAATTG | ACATGTCTAA | GTTTAGCACT | AAAGAGGCAG | TTGGGAAAGT | GTGCACAGTT | 600 |
| CTAAAAAGCA | AAGGATATAG | CATGAACTCT | GTTGAAATTG | GCAAGGCTAA | ACAATATGCA | 660 |
| GATATACTAA | AGGCTTGTAG | TCCGAAAGCT | AAAGGACTTG | CTGCAATGGA | CCACTACAAA | 720 |
| GAAGGGCTTA | CATCCATTTA | CAGCATGTTT | AATGCTACTA | TTGATTTTGG | GAAAAATGAT | 780 |
| TCTATTTAA | | | | | | 789 |

( 2 ) INFORMATION FOR SEQ ID NO:12:

( i ) SEQUENCE CHARACTERISTICS:
        ( A ) LENGTH: 1350 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

| | | | | | |
|---|---|---|---|---|---|
| TTAATTTAAA | TCTAATTTAG | AAATAGCTTT | CAAAACATCC | TCTGATCTAG | GAGAAATTTT | 60 |
| TATTTCACCT | GCAGCATAGT | CAAATTTCCA | ATCGGGCATC | TGGATGCTAT | CCAAATAAGA | 120 |
| CATTGTTTGT | GAGTTTCTCG | GAAGACTTTT | CAAGGTCTGA | GAAAGGAAAT | ATTTCTCCC | 180 |
| ATAACCATCT | TCTGAATAAT | TTAAAGTCTT | TTTCCCTAGC | TCAAACTTTT | TTGGCTTTAG | 240 |
| ATCTGGCTCA | TTTATAGTGA | AGACAATCAT | GTCTTGCTGA | ACACTGTCAC | AGACAGTTTG | 300 |
| AGCAAGTTCT | GTGTGGATTT | CAAGAAGTGA | ATGAACAATT | CTTTGAGGAT | ACGACATATC | 360 |
| ATGGATAACA | TTGTAAGGTT | CTTTTAGATC | AGAAAAATTC | ATCTCAATTT | TATGAATCAC | 420 |
| TGCTAGAAGG | AGTTGATTCA | AGAAGAGGTT | TGACTGATCA | AAGTTATATT | CAATGACTGT | 480 |
| TTCAACATTG | TTGTGATTCG | GAAGACATTG | AATGCTTATA | TAATACTCTT | TAGGAGAAGA | 540 |
| TTCATCAGAC | AGGGTGAAGA | ACCGGCTGTA | TGTGTTTGAT | TCATTATTT | TAGGGATGCG | 600 |
| CATCCAAAGG | CTGATTTTAA | AAGGCTTGTT | ATTATTGAGC | CTGACAAACG | AATGAGTATC | 660 |
| TGACATTAAA | TCAGAAGTTG | CAGACATTGC | CAGTGATTTT | ACAGCCAAAG | TGTTTACTGT | 720 |

| | | | | | | |
|---|---|---|---|---|---|---|
| CCTGTTGTTG | GTCTGGGATT | GGTTAAAAAC | AGGCTTAAGT | GTGTACAGCC | ATTCATGAAC | 780 |
| ACTTCTGGTA | GGAGAAAGAA | CACTGACTTT | GCCCATGGAT | TGGTTGTTTG | AATACTTGAC | 840 |
| ATCAAAAAGG | ACTTCTTTGA | CACAAGACAA | TGATCCTTTA | TTTGCAGCTT | CAATGAAATT | 900 |
| ATTTGGAGGG | AAGATGTCAG | ATTCTTTCAG | ACCGAATCTT | GAAGTAATTT | CAGGCACTGC | 960 |
| TATTTGCTCT | TCAAGCATTC | TGAGCAACTG | AGAGGATAAC | ACTTTGAGAT | GACCTTGATG | 1020 |
| TTTAACACCG | TTTGTGTTTG | TTGTGTTAGA | TCTGACCAGA | ATTTCGACAA | CATTCCCTGA | 1080 |
| AAAGGAGAAA | TTCAGATCAA | TGTCATCAAA | AATAGGCACA | AACATCTCA | CTATAATTTC | 1140 |
| TTTTTCTTCT | GTTGGGAGAA | AGCCAACTTT | ACCAGTGTAA | CAGAAACTGG | TCTTGCTCCT | 1200 |
| GGAGTCAGAA | TAGAGTTGAG | CTTCGACCAA | CTTCTTTCCG | GAAGATTGAT | CATGAATCCA | 1260 |
| ATAACTATCT | ACTACTGCTT | TACCCGAAGA | TGTTGTTCCC | CAGATTGAGG | ACTTCGATTT | 1320 |
| GATAATTGTT | TCATACATTG | CACTAGACAT | | | | 1350 |

(2) INFORMATION FOR SEQ ID NO:13:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (xi) SEQUENCE DESCRIPTION: SEQ ID NO:13:

| | | | | | | |
|---|---|---|---|---|---|---|
| AAGAGATTTG | AGCTTGGTTT | GCTTTGTGTT | GTGTTAAATG | CATTTAAATA | AATAAAAATA | 60 |
| AAAATAATAA | AATAAAAAA | TAAATAAAA | AATAAAATAA | TTAATTATTG | TTTGAGTGTA | 120 |
| TTAAGTGTGC | TTTTATAAAT | TATTTGAAAT | AAGTTTAATG | TGTGTTTTAA | TATATAAACT | 180 |
| TGAAAGTGTG | TTTGCGTGTG | AAATAAACAA | GTAAAAAGC | TACAAAAAAT | AATAAAAACA | 240 |
| ATAAAAACCA | CTACAAAATA | TATATATATA | TATATATAAA | TAAAATAAAA | AACAAAAAAC | 300 |
| AAAAAACAAA | ATAAAAAACA | AATAAAACAA | AACAAAAACA | AAAACAAAA | AACAAAAACA | 360 |
| AAAACAAATA | CAAATTTTTG | GCCAATTTGT | GAGTAGATTG | GATTAAAGT | TTATAATTTA | 420 |
| CTAATACATT | CTTTTAAAGC | ATTATTAAAG | CAACCAAATT | GTGCCCGAAG | GCCATCCTTT | 480 |
| TTTGGTTTTT | ATTTATTTTA | TGATTTTTTT | TGTATTTTTT | ATATATTTTA | TGTTTATTTA | 540 |
| TTTATTTCAT | ATGATTGTTT | TTGGTTTATC | TGTTATTAGA | TTTGTTTAAT | CTGATCTAAA | 600 |
| TGCATGTAAA | CAAACTTTAC | TTAGGGACAA | GTTAACCAA | GG | | 642 |

(2) INFORMATION FOR SEQ ID NO:14:

(i) SEQUENCE CHARACTERISTICS:
        (A) LENGTH: 4970 base pairs
        (B) TYPE: nucleic acid
        (C) STRANDEDNESS: single
        (D) TOPOLOGY: linear (xi) SEQUENCE DESCRIPTION: SEQ ID NO:14:

| | | | | | | |
|---|---|---|---|---|---|---|
| AGAGCAATCA | GTGCATCAAA | ATTATATCTA | GCCGAATTCA | ATCATTATCT | TCTCAATATT | 60 |
| TTAATTCTTA | ATCTACCGTC | CAGAGATGAA | TAGTTTTTTC | AAATCACTCA | GATCATCTAG | 120 |
| CAGCAGGGAG | CTAGATCACC | CTAGGGTTAC | AACTACCCTC | TCTAAACAAG | GAGCAGACAT | 180 |
| TGTTGTACAC | AATCCTTCTG | CTAATCACAA | CAACAAGGAA | GTTCTCCAAA | GAGCCATGGA | 240 |
| TAGCTCTAAA | GGGAAGATTT | TGATGAACAA | TACAGGCACC | TCATCACTAG | GCACATATGA | 300 |
| GTCTGACCAG | ATATCTGAAT | CAGAGTCTTA | TGATCTTTCT | GCTAGAATGA | TTGTTGATAC | 360 |
| AAATCATCAT | ATCTCCAGCT | GGAAAAATGA | TCTTTTTGTA | GGTAATGGTG | ATAAAGCTGC | 420 |

```
AACCAAGATA ATTAAGATAC ATCCAACCTG GGATAGCAGA AAACAATACA TGATGATCTC      480

AAGGATAGTT ATCTGGATAT GCCCTACTAT AGCTGATCCT GATGGGAAAT TGGCTGTAGC      540

TTTAATTGAT CCTAACAAGA GTGTTAATGC CAGAACTGTT TTGAAAGGGC AAGGAAGCAT      600

TAAAGATCCT ATATGTTTTG TTTTTTATCT AAATTGGTCC ATTCCAAAAG TTAACAACAC      660

TTCAGAGAAT TGTGTTCAGC TTCATTTATT ATGTGATCAA GTTTACAAGA AAGATGTTTC      720

TTTTGCTAGT GTCATGTATT CTTGGACAAA AGAATTCTGT GATTCACCAA GAGCAGATCT      780

GGATAAAAGC TGCATGATAA TACCCATCAA TAGGGCTATT AGAGCCAAAT CGCAAGCCTT      840

CATTGAAGCC TGCAAGTTAA TCATACCTAA AGGCAATTCT GAAAAGCAAA TTAGAAGACA      900

ACTTGCAGAG CTAAGTGCTA ATTTAGAGAA ATCTGTTGAA GAAGAGGAGA ATGTTACTGA      960

TAACAAGATA GAGATATCAT TTGATAATGA AATCTAAATA TGTTTTCATT TAATAATAAA     1020

TAATATATAT TGTTCATAAT ATTTTGAATG TTTAAGTAAA AAATAAAGCA AGATAAAAAA     1080

CTATATATAT ATATATATAT AGAAGTATAA AATATATATG TATTTGTGTT TAAAAACAAA     1140

TCAAAAACCA AAAAAGAAAA AAGAAAAAAT AAACAAAAAA CAAAACAAA AACAAAAACA      1200

AACAAAAAGC AAAAAATAGA AAAAGTTGA AAAAAACCAA AAAATTTTT TTTGTAAATA       1260

AATAAGGCTC CGGCCAGATT TGGTCTAAGA CCTTTTTATT TGTTTTTATA CATTTTATTT     1320

GTTTTGTTG ATTTTTATTT TTATTATTTT TATATTTTTT ATATAGTTTG CTTATTTAAC      1380

ACTTATTTAG ACAAATTAAA TTTATTTGAT TACAATCATT CTGCCTTATT TAATTTAAAA     1440

CACATTTGGT GTATATTCCA ATGAATTTAA TCATATACCG CTGAAGTCTA GAGGAGGTCT     1500

TCTTCTAGTG ATGGTGTCTT TACCAGAAGA CGTGGAAACC AAAGAATAAT CATTAGTGTC     1560

TTCAATATAT TTTGTCTTGT AAGACTTGTT CTAACATAG CCTCTACACA TTGTGGCAAC      1620

AATAGAGCAG AGGTAAGCAA GAGCAAATAC AAAGAGTATG AGCAATACTA CTCTGACTGT     1680

ATCAAAGAAG GATCCAAAGT GGCTTGCTAT AAAGTTAAAA GGGCTTTTAA CATAGTCCCA     1740

AAAGCTCCAA ACTGATGTGT CAGAATTATA TTGCTGTTCC TCGTGTGCAT GTTGGTCATT     1800

TTGATCAATT ATGTTTCTG GTTCCAGCAC AGCAACAGAA TCTACAAGTG CCTCAACTGA      1860

GTATGATTTG TCTCCTTCTG GTTCTATAAT CATTTTTGT TTTTCTGGGT TAGAAGTGCA      1920

GAACATTGTC AAGTTATACT TATTAGCACC TTTCTTTACT GCTATCTGGT ATGTTGACAA     1980

TGAACATTGT TTCATGGTTA ACCTTGCAGA AAAAGTTATG TCTGATATAA ATGAGGCAGC     2040

ACACCTCAGC CCTTGGCTAC ATAAGAAACA TCCCTTACAG CTTAAAGAGA CAGAACTCAA     2100

TATAGGCTTT TTTGGTACAG TTTTAAACAA TTCAGAAGGT AGATCCAAAA CAATTTTAAG     2160

CTTACCTAGA CTAAAGATCT TTTCCATATA AAAACTATTC TGGTCAGTAA ACTGAACTGG     2220

AATGTCCGAT ATTTGGTTCA AACCTGTTTT AAATCTGTAT GTGTCATAAC CACATGATTT     2280

TATCGTAATT GTTTTTTAC CAATTGCTGA ACAATCCCAG GACAGATCGT TTGTATCTAA      2340

TGTTTTCTTA GAGAAAATGG GATCACCTTG GTGTGAAAGT TGAGGATGAC CAAACATTTT     2400

TGATGGATTA TTTAATCTAG CTATGTTTCC CGCATATACG TGACTATCAG GTCCATGAGC     2460

TATCAGCTGG CCTATTGTTA AGCCATCATT ATGGAAATCC GCTAATATAT CAGCCTGGAA     2520

ATATCCTGAT TCAGATGGGA CTTCCTCAGA TACAGTGAAA CACTTTGCTC CCACAAATCC     2580

AGATATACAT ACTTCAGACT TGATTGTTGA TTTAATAACA GAATAAATCC TGAAAGATTG     2640

ATCCATATCA TACACATTTC TACAAAACCC ACAAGTGGCT CCTTCATTGA TAGCCAAACA     2700

CCAAACCTCT TCACAACCCC AGTAAGATGT TGGTGTTATG CAGAAATCTT GATACCCAGT     2760

TATCGGTTGT TCTTTTCTGC AATCTGAGCA TTTACCTGTG CATGTTGAAA AGAAATCAGT     2820
```

```
GTGGGTGCTT TGTATAGGAG CTGTAGTGTA TTGTTCAGAA ACATCATACT GTATTCTAAC    2880
TTTTTTAATA TAAACAACAA ACTTCTGAGC AGTGCTAGAA CTTTTGTCAT TAAGAGAGAA    2940
AACTGTGCCC CCACCTGATA ATAAAGATTC TTCTATCATG TATCTATATT TTCCATCTAT    3000
CACCGAGTCA AATATGAGAG ATTTTCTTGG AAAAATGCTT TCAGGTATGT CTGATTCATT    3060
AGATTTAAGT GCATCTCCAG AAATGTATCC ATATTTTCA GTTTATTGT AGAAATCAAT     3120
TATACCATTC CTAAGCCTTT TCATGAAGTG TAGATTCACA GCATTCAATC CCAATGTGTC    3180
ACCAGAATAT TCTAAGAACC CATTATCTAA AGGCTTGCTT TGGAAAATAG AGGCATACTC    3240
ACAACCAAAT CTGCATTTGA CAAAAGTTAC TAAAGCATTT TCAGTTATCC TGCCTTTGCA    3300
TTCTTGATAA GGTATACAAT CCATAGGACC TTCTGTCACA ACATTGGTTA GAAAGTTAGA    3360
TTCTACAATA GAATTTTCTT TAATAGCACA GAAGCATTGG TCTTTTTCAG GACATTTGTC    3420
ATATCTGTTT GTAACAAAGC GGTCACAACC AGGGACATAA TAACAGCTAT CCAAACACTG    3480
AGCAGTTTGA GCCATAGACA TAGGCATCTG TGACAAAATC AGAAATCCTA TCAAAGTTTC    3540
TGTGACTGCT TTTAGGAAAG AGAGGCCTAT TTTTGTATTA ACTATCAAAT GGAACCATTC    3600
AATGCTAGCC CAGTTGTATT TTTTATTCTT CTCTGCTGTT CTAGTTATTA TAGGACATTC    3660
TTCTGAGTGT TCTTCAGAGG CTTTGTTTTT GTTACAAATG CATAATTTTG AGCATTCATG    3720
GGTTACCAAA CATAAATTTC CACAGACCTT ACATTTCAAG GGAAAATAAG ACCATAAATA    3780
ATTTATCAGT AGTAGTATAG GATACGTTAT CAATCCCAGA AGATCATACC CATAGAACAG    3840
TGTTTTAGAT GTTTGTTTA CCAAGTACCT TATAGGGAAA TAGACAATCA GAGCAATCAT     3900
GATCAATCTA AACCATGAGA AGTTGATGCA AGCAGTTTGT TTGTAAATAT TTTTGGAGTA    3960
CTTTATAATA CAATCTCTAA CTCTTTTGTC CACTAAAGGA ACTTAGAAG ACTTGTCACC     4020
GCACAATAGG TTATGCTTAC CATCCATATT TTCTTCTGTG AAAGTCAAAC TAACTGAGCC    4080
AGAGAAGCTT ATTATGGAAT GGCTCATGTC ACTTCCTTCT CTTTTGACGA CGTAACCCAT    4140
GATTTTCTCA GGTGTAGTTA ATGAAACTGT ATAAGAATTA ACTATGTTTG TTTTTGATAT    4200
TTTACAATCA CCTGAGAATT TCACACTCTG GAGAGAGACT GTGCCATTAG TTGGTCTAGA    4260
ATTGTACATG ATTGGATAAT TGTAATTCTC CAAACTTTCA ATTATATAGA ATTTAGTTCC    4320
TATAGATAAT TTCCTTTTGT TATCGATTTT TGTTATTGGT ACAACTGGAA CAGTTTCAAA    4380
GCTTCTTGGC AATTCAGAAG ATCCTTCACA GTTTCCCAAT TTAGTTATAG TGTCACTGAT    4440
ACATGAATAT ATAACACCAT TGCTTTCTAC TTGGTAATAA ACATTGAATG TTGAAACTCC    4500
TTTAATGCTA CAAGTCAAAC TTGAAGCATT TAGGCATGGA TTTGGTAAAT CCATAACTGA    4560
TATAGTTGTT GGTGTAGAAG ACAATCCACT TGGAGATTGA GGTACCTCAT TATTGGCAAG    4620
AACAGTTTGA GTATCTCGTG TTGGTCTAAG GGTTTTACCT GTTGCATTCT GGAGCATTTC    4680
AGCCAAAGTA TCTAGAATTT CATTTTTATG ATCTACAGAA CGGTCATAAT AAGCTTCATC    4740
ATAAATTTCT GGATGATCGC CCCTTTCAAC ATGAATCTTT GCATCTGTCT CCTTTAATGC    4800
CATAAAGGAT AAGATAACAG AAGTAACAAC TAGTGTACAT ACACTAATTT TAACAAGTAA    4860
CTCGCACATC TTTAGAATTT TCATTCTAAA AAGTCGAATA ACACTAGTTC TAAAATTGCT    4920
TTATGAGTTT GATCTGTTGT ATGTAGAGTT TTGTTTGCAC TGATTGCTCT                4970
```

( 2 ) INFORMATION FOR SEQ ID NO:15:

( i ) SEQUENCE CHARACTERISTICS:
        ( A ) LENGTH: 912 base pairs
        ( B ) TYPE: nucleic acid
        ( C ) STRANDEDNESS: single ( D ) TOPOLOGY: linear ( x i ) SEQUENCE DESCRIPTION: SEQ ID NO:15:

| | | | | | | |
|---|---|---|---|---|---|---|
| ATGAATAGTT | TTTTCAAATC | ACTCAGATCA | TCTAGCAGCA | GGGAGCTAGA | TCACCCTAGG | 60 |
| GTTACAACTA | CCCTCTCTAA | ACAAGGAGCA | GACATTGTTG | TACACAATCC | TTCTGCTAAT | 120 |
| CACAACAACA | AGGAAGTTCT | CCAAGAGCC | ATGGATAGCT | CTAAAGGGAA | GATTTGATG | 180 |
| AACAATACAG | GCACCTCATC | ACTAGGCACA | TATGAGTCTG | ACCAGATATC | TGAATCAGAG | 240 |
| TCTTATGATC | TTTCTGCTAG | AATGATTGTT | GATACAAATC | ATCATATCTC | CAGCTGGAAA | 300 |
| AATGATCTTT | TTGTAGGTAA | TGGTGATAAA | GCTGCAACCA | AGATAATTAA | GATACATCCA | 360 |
| ACCTGGGATA | GCAGAAAACA | ATACATGATG | ATCTCAAGGA | TAGTTATCTG | GATATGCCCT | 420 |
| ACTATAGCTG | ATCCTGATGG | GAAATTGGCT | GTAGCTTTAA | TTGATCCTAA | CAAGAGTGTT | 480 |
| AATGCCAGAA | CTGTTTTGAA | AGGGCAAGGA | AGCATTAAAG | ATCCTATATG | TTTTGTTTTT | 540 |
| TATCTAAATT | GGTCCATTCC | AAAAGTTAAC | AACACTTCAG | AGAATTGTGT | TCAGCTTCAT | 600 |
| TTATTATGTG | ATCAAGTTTA | CAAGAAAGAT | GTTTCTTTTG | CTAGTGTCAT | GTATTCTTGG | 660 |
| ACAAAAGAAT | TCTGTGATTC | ACCAAGAGCA | GATCTGGATA | AAAGCTGCAT | GATAATACCC | 720 |
| ATCAATAGGG | CTATTAGAGC | CAAATCGCAA | GCCTTCATTG | AAGCCTGCAA | GTTAATCATA | 780 |
| CCTAAAGGCA | ATTCTGAAAA | GCAAATTAGA | AGACAACTTG | CAGAGCTAAG | TGCTAATTTA | 840 |
| GAGAAATCTG | TTGAAGAAGA | GGAGAATGTT | ACTGATAACA | AGATAGAGAT | ATCATTTGAT | 900 |
| AATGAAATCT | AA | | | | | 912 |

( 2 ) INFORMATION FOR SEQ ID NO:16:

( i ) SEQUENCE CHARACTERISTICS:
                ( A ) LENGTH: 473 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:16:

| | | | | | | |
|---|---|---|---|---|---|---|
| ATATGTTTTC | ATTTAATAAT | AAATAATATA | TATTGTTCAT | AATATTTTGA | ATGTTTAAGT | 60 |
| AAAAAATAAA | GCAAGATAAA | AAACTATATA | TATATATATA | TATAGAAGTA | TAAAATATAT | 120 |
| ATGTATTTGT | GTTTAAAAAC | AAATCAAAAA | CCAAAAAAGA | AAAAGAAAA | AATAAACAAA | 180 |
| AAACAAAAAC | AAAAACAAAA | ACAAACAAAA | AGCAAAAAAT | AGAAAAAAGT | TGAAAAAAAC | 240 |
| CAAAAAAATT | TTTTTTGTAA | ATAAATAAGG | CTCCGGCCAG | ATTTGGTCTA | AGACCTTTTT | 300 |
| ATTTGTTTTT | ATACATTTTA | TTTGTTTTTG | TTGATTTTTA | TTTTTATTAT | TTTTATATTT | 360 |
| TTTATATAGT | TTGCTTATTT | AACACTTATT | TAGACAAATT | AAATTTATTT | GATTACAATC | 420 |
| ATTCTGCCTT | ATTTAATTTA | AAACACATTT | GGTGTATATT | CCAATGAATT | TAA | 473 |

( 2 ) INFORMATION FOR SEQ ID NO:17:

( i ) SEQUENCE CHARACTERISTICS:
                ( A ) LENGTH: 3414 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:17:

| | | | | | | |
|---|---|---|---|---|---|---|
| TCATATACCG | CTGAAGTCTA | GAGGAGGTCT | TCTTCTAGTG | ATGGTGTCTT | TACCAGAAGA | 60 |
| CGTGGAAACC | AAAGAATAAT | CATTAGTGTC | TTCAATATAT | TTTGTCTTGT | AAGACTTGTT | 120 |
| TCTAACATAG | CCTCTACACA | TTGTGGCAAC | AATAGAGCAG | AGGTAAGCAA | GAGCAAATAC | 180 |

| | | | | | | |
|---|---|---|---|---|---|---|
| AAAGAGTATG | AGCAATACTA | CTCTGACTGT | ATCAAAGAAG | GATCCAAAGT | GGCTTGCTAT | 240 |
| AAAGTTAAAA | GGGCTTTTAA | CATAGTCCCA | AAAGCTCCAA | ACTGATGTGT | CAGAATTATA | 300 |
| TTGCTGTTCC | TCGTGTGCAT | GTTGGTCATT | TTGATCAATT | ATGTTTTCTG | GTTCCAGCAC | 360 |
| AGCAACAGAA | TCTACAAGTG | CCTCAACTGA | GTATGATTTG | TCTCCTTCTG | GTTCTATAAT | 420 |
| CATTTTTTGT | TTTTCTGGGT | TAGAAGTGCA | GAACATTGTC | AAGTTATACT | TATTAGCACC | 480 |
| TTTCTTTACT | GCTATCTGGT | ATGTTGACAA | TGAACATTGT | TTCATGGTTA | ACCTTGCAGA | 540 |
| AAAAGTTATG | TCTGATATAA | ATGAGGCAGC | ACACCTCAGC | CCTTGGCTAC | ATAAGAAACA | 600 |
| TCCCTTACAG | CTTAAAGAGA | CAGAACTCAA | TATAGGCTTT | TTTGGTACAG | TTTTAAACAA | 660 |
| TTCAGAAGGT | AGATCCAAAA | CAATTTTAAG | CTTACCTAGA | CTAAAGATCT | TTTCCATATA | 720 |
| AAAACTATTC | TGGTCAGTAA | ACTGAACTGG | AATGTCCGAT | ATTTGGTTCA | AACCTGTTTT | 780 |
| AAATCTGTAT | GTGTCATAAC | CACATGATTT | TATCGTAATT | GTTTTTTTAC | CAATTGCTGA | 840 |
| ACAATCCCAG | GACAGATCGT | TTGTATCTAA | TGTTTTCTTA | GAGAAAATGG | GATCACCTTG | 900 |
| GTGTGAAAGT | TGAGGATGAC | CAAACATTTT | TGATGGATTA | TTTAATCTAG | CTATGTTTCC | 960 |
| CGCATATACG | TGACTATCAG | GTCCATGAGC | TATCAGCTGG | CCTATTGTTA | AGCCATCATT | 1020 |
| ATGGAAATCC | GCTAATATAT | CAGCCTGGAA | ATATCCTGAT | TCAGATGGGA | CTTCCTCAGA | 1080 |
| TACAGTGAAA | CACTTTGCTC | CCACAAATCC | AGATATACAT | ACTTCAGACT | TGATTGTTGA | 1140 |
| TTTAATAACA | GAATAAATCC | TGAAAGATTG | ATCCATATCA | TACACATTTC | TACAAAACCC | 1200 |
| ACAAGTGGCT | CCTTCATTGA | TAGCCAAACA | CCAAACCTCT | TCACAACCCC | AGTAAGATGT | 1260 |
| TGGTGTTATG | CAGAAATCTT | GATACCCAGT | TATCGGTTGT | TCTTTTCTGC | AATCTGAGCA | 1320 |
| TTTACCTGTG | CATGTTGAAA | AGAAATCAGT | GTGGGTGCTT | TGTATAGGAG | CTGTAGTGTA | 1380 |
| TTGTTCAGAA | ACATCATACT | GTATTCTAAC | TTTTTAATA | TAAACAACAA | ACTTCTGAGC | 1440 |
| AGTGCTAGAA | CTTTTGTCAT | TAAGAGAGAA | AACTGTGCCC | CCACCTGATA | ATAAAGATTC | 1500 |
| TTCTATCATG | TATCTATATT | TTCCATCTAT | CACCGAGTCA | AATATGAGAG | ATTTCTTGG | 1560 |
| AAAAATGCTT | TCAGGTATGT | CTGATTCATT | AGATTTAAGT | GCATCTCCAG | AAATGTATCC | 1620 |
| ATATTTTTCA | GTTTTATTGT | AGAAATCAAT | TATACCATTC | CTAAGCCTTT | TCATGAAGTG | 1680 |
| TAGATTCACA | GCATTCAATC | CCAATGTGTC | ACCAGAATAT | TCTAAGAACC | CATTATCTAA | 1740 |
| AGGCTTGCTT | TGGAAAATAG | AGGCATACTC | ACAACCAAAT | CTGCATTTGA | CAAAAGTTAC | 1800 |
| TAAAGCATTT | TCAGTTATCC | TGCCTTTGCA | TTCTTGATAA | GGTATACAAT | CCATAGGACC | 1860 |
| TTCTGTCACA | ACATTGGTTA | GAAAGTTAGA | TTCTACAATA | GAATTTCTT | TAATAGCACA | 1920 |
| GAAGCATTGG | TCTTTTTCAG | GACATTTGTC | ATATCTGTTT | GTAACAAAGC | GGTCACAACC | 1980 |
| AGGGACATAA | TAACAGCTAT | CCAAACACTG | AGCAGTTTGA | GCCATAGACA | TAGGCATCTG | 2040 |
| TGACAAAATC | AGAAATCCTA | TCAAAGTTTC | TGTGACTGCT | TTTAGGAAAG | AGAGGCCTAT | 2100 |
| TTTTGTATTA | ACTATCAAAT | GGAACCATTC | AATGCTAGCC | CAGTTGTATT | TTTTATTCTT | 2160 |
| CTCTGCTGTT | CTAGTTATTA | TAGGACATTC | TTCTGAGTGT | TCTTCAGAGG | CTTTGTTTTT | 2220 |
| GTTACAAATG | CATAATTTTG | AGCATTCATG | GGTTACCAAA | CATAAATTTC | CACAGACCTT | 2280 |
| ACATTTCAAG | GGAAAATAAG | ACCATAAATA | ATTTATCAGT | AGTAGTATAG | GATACGTTAT | 2340 |
| CAATCCCAGA | AGATCATACC | CATAGAACAG | TGTTTTAGAT | GTTTTGTTTA | CCAAGTACCT | 2400 |
| TATAGGGAAA | TAGACAATCA | GAGCAATCAT | GATCAATCTA | AACCATGAGA | AGTTGATGCA | 2460 |
| AGCAGTTTGT | TTGTAAATAT | TTTTGGAGTA | CTTTATAATA | CAATCTCTAA | CTCTTTTGTC | 2520 |
| CACTAAAGGA | ACTTTAGAAG | ACTTGTCACC | GCACAATAGG | TTATGCTTAC | CATCCATATT | 2580 |

-continued

| | | | | | |
|---|---|---|---|---|---|
| TTCTTCTGTG | AAAGTCAAAC | TAACTGAGCC | AGAGAAGCTT | ATTATGGAAT | GGCTCATGTC | 2640 |
| ACTTCCTTCT | CTTTTGACGA | CGTAACCCAT | GATTTTCTCA | GGTGTAGTTA | ATGAAACTGT | 2700 |
| ATAAGAATTA | ACTATGTTTG | TTTTTGATAT | TTTACAATCA | CCTGAGAATT | TCACACTCTG | 2760 |
| GAGAGAGACT | GTGCCATTAG | TTGGTCTAGA | ATTGTACATG | ATTGGATAAT | TGTAATTCTC | 2820 |
| CAAACTTTCA | ATTATATAGA | ATTTAGTTCC | TATAGATAAT | TTCCTTTTGT | TATCGATTTT | 2880 |
| TGTTATTGGT | ACAACTGGAA | CAGTTTCAAA | GCTTCTTGGC | AATTCAGAAG | ATCCTTCACA | 2940 |
| GTTTCCCAAT | TTAGTTATAG | TGTCACTGAT | ACATGAATAT | ATAACACCAT | TGCTTTCTAC | 3000 |
| TTGGTAATAA | ACATTGAATG | TTGAAACTCC | TTTAATGCTA | CAAGTCAAAC | TTGAAGCATT | 3060 |
| TAGGCATGGA | TTTGGTAAAT | CCATAACTGA | TATAGTTGTT | GGTGTAGAAG | ACAATCCACT | 3120 |
| TGGAGATTGA | GGTACCTCAT | TATTGGCAAG | AACAGTTTGA | GTATCTCGTG | TTGGTCTAAG | 3180 |
| GGTTTTACCT | GTTGCATTCT | GGAGCATTTC | AGCCAAAGTA | TCTAGAATTT | CATTTTTATG | 3240 |
| ATCTACAGAA | CGGTCATAAT | AAGCTTCATC | ATAAATTTCT | GGATGATCGC | CCCTTTCAAC | 3300 |
| ATGAATCTTT | GCATCTGTCT | CCTTTAATGC | CATAAAGGAT | AAGATAACAG | AAGTAACAAC | 3360 |
| TAGTGTACAT | ACACTAATTT | TAACAAGTAA | CTCGCACATC | TTTAGAATTT | TCAT | 3414 |

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

| | | | | |
|---|---|---|---|---|
| AGAGCAATCA | GTGCATCAAA | ATTATATCTA | GCCGAA | 36 |

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

| | | | |
|---|---|---|---|
| CTGTTGTATG | TAGAGTTTTG | TTTGCACTGA | TTGCTC | 36 |

( 2 ) INFORMATION FOR SEQ ID NO:20:

( i ) SEQUENCE CHARACTERISTICS:
        ( A ) LENGTH: 4970 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

| | | | | | |
|---|---|---|---|---|---|
| AGAGCAATCA | GTGCAAACAA | AACTCTACAT | ACAACAGATC | AAACTCATAA | AGCAATTTTA | 60 |
| GAACTAGTGT | TATTCGACTT | TTTAGAATGA | AAATTCTAAA | GATGTGCGAG | TTACTTGTTA | 120 |
| AAATTAGTGT | ATGTACACTA | GTTGTTACTT | CTGTTATCTT | ATCCTTTATG | GCATTAAAGG | 180 |
| AGACAGATGC | AAAGATTCAT | GTTGAAAGGG | GCGATCATCC | AGAAATTTAT | GATGAAGCTT | 240 |
| ATTATGACCG | TTCTGTAGAT | CATAAAAATG | AAATTCTAGA | TACTTTGGCT | GAAATGCTCC | 300 |
| AGAATGCAAC | AGGTAAAACC | CTTAGACCAA | CACGAGATAC | TCAAACTGTT | CTTGCCAATA | 360 |
| ATGAGGTACC | TCAATCTCCA | AGTGGATTGT | CTTCTACACC | AACAACTATA | TCAGTTATGG | 420 |
| ATTTACCAAA | TCCATGCCTA | AATGCTTCAA | GTTTGACTTG | TAGCATTAAA | GGAGTTTCAA | 480 |

-continued

```
CATTCAATGT TTATTACCAA GTAGAAAGCA ATGGTGTTAT ATATTCATGT ATCAGTGACA    540
CTATAACTAA ATTGGGAAAC TGTGAAGGAT CTTCTGAATT GCCAAGAAGC TTTGAAACTG    600
TTCCAGTTGT ACCAATAACA AAAATCGATA ACAAAAGGAA ATTATCTATA GGAACTAAAT    660
TCTATATAAT TGAAAGTTTG GAGAATTACA ATTATCCAAT CATGTACAAT TCTAGACCAA    720
CTAATGGCAC AGTCTCTCTC CAGAGTGTGA AATTCTCAGG TGATTGTAAA ATATCAAAAA    780
CAAACATAGT TAATTCTTAT ACAGTTTCAT TAACTACACC TGAGAAAATC ATGGGTTACG    840
TCGTCAAAAG AGAAGGAAGT GACATGAGCC ATTCCATAAT AAGCTTCTCT GGCTCAGTTA    900
GTTTGACTTT CACAGAAGAA ATATGGATG GTAAGCATAA CCTATTGTGC GGTGACAAGT    960
CTTCTAAAGT TCCTTTAGTG GACAAAAGAG TTAGAGATTG TATTATAAAG TACTCCAAAA   1020
ATATTTACAA ACAAACTGCT TGCATCAACT TCTCATGGTT TAGATTGATC ATGATTGCTC   1080
TGATTGTCTA TTTCCCTATA AGGTACTTGG TAAACAAAAC ATCTAAAACA CTGTTCTATG   1140
GGTATGATCT TCTGGGATTG ATAACGTATC CTATACTACT ACTGATAAAT TATTTATGGT   1200
CTTATTTTCC CTTGAAATGT AAGGTCTGTG GAAATTTATG TTTGGTAACC CATGAATGCT   1260
CAAAATTATG CATTTGTAAC AAAAACAAAG CCTCTGAAGA ACACTCAGAA GAATGTCCTA   1320
TAATAACTAG AACAGCAGAG AAGAATAAAA AATACAACTG GCTAGCATT GAATGGTTCC    1380
ATTTGATAGT TAATACAAAA ATAGGCCTCT CTTTCCTAAA AGCAGTCACA GAAACTTTGA   1440
TAGGATTTCT GATTTGTCA CAGATGCCTA TGTCTATGGC TCAAACTGCT CAGTGTTTGG    1500
ATAGCTGTTA TTATGTCCCT GGTTGTGACC GCTTTGTTAC AAACAGATAT GACAAATGTC   1560
CTGAAAAAGA CCAATGCTTC TGTGCTATTA AGAAAATTC TATTGTAGAA TCTAACTTTC    1620
TAACCAATGT TGTGACAGAA GGTCCTATGG ATTGTATACC TTATCAAGAA TGCAAAGGCA   1680
GGATAACTGA AAATGCTTTA GTAACTTTTG TCAAATGCAG ATTTGGTTGT GAGTATGCCT   1740
CTATTTTCCA AAGCAAGCCT TTAGATAATG GGTTCTTAGA ATATTCTGGT GACACATTGG   1800
GATTGAATGC TGTGAATCTA CACTTCATGA AAAGGCTTAG GAATGGTATA ATTGATTTCT   1860
ACAATAAAAC TGAAAAATAT GGATACATTT CTGGAGATGC ACTTAAATCT AATGAATCAG   1920
ACATACCTGA AAGCATTTTT CCAAGAAAAT CTCTCATATT TGACTCGGTG ATAGATGGAA   1980
AATATAGATA CATGATAGAA GAATCTTTAT TATCAGGTGG GGGCACAGTT TTCTCTCTTA   2040
ATGACAAAAG TTCTAGCACT GCTCAGAAGT TTGTTGTTTA TATTAAAAAA GTTAGAATAC   2100
AGTATGATGT TTCTGAACAA TACACTACAG CTCCTATACA AAGCACCCAC ACTGATTTCT   2160
TTTCAACATG CACAGGTAAA TGCTCAGATT GCAGAAAAGA ACAACCGATA ACTGGGTATC   2220
AAGATTTCTG CATAACACCA ACATCTTACT GGGGTTGTGA AGAGGTTTGG TGTTTGGCTA   2280
TCAATGAAGG AGCCACTTGT GGGTTTTGTA GAAATGTGTA TGATATGGAT CAATCTTTCA   2340
GGATTTATTC TGTTATTAAA TCAACAATCA AGTCTGAAGT ATGTATATCT GGATTTGTGG   2400
GAGCAAAGTG TTTCACTGTA TCTGAGGAAG TCCCATCTGA ATCAGGATAT TTCCAGGCTG   2460
ATATATTAGC GGATTTCCAT AATGATGGCT TAACAATAGG CCAGCTGATA GCTCATGGAC   2520
CTGATAGTCA CGTATATGCG GGAAACATAG CTAGATTAAA TAATCCATCA AAAATGTTTG   2580
GTCATCCTCA ACTTTCACAC CAAGGTGATC CCATTTTCTC TAAGAAAACA TTAGATACAA   2640
ACGATCTGTC CTGGGATTGT TCAGCAATTG GTAAAAAAC AATTACGATA AAATCATGTG    2700
GTTATGACAC ATACAGATTT AAAACAGGTT TGAACCAAAT ATCGGACATT CCAGTTCAGT   2760
TTACTGACCA GAATAGTTTT TATATGGAAA AGATCTTTAG TCTAGGTAAG CTTAAAATTG   2820
TTTTGGATCT ACCTTCTGAA TTGTTTAAAA CTGTACCAAA AAAGCCTATA TTGAGTTCTG   2880
```

| | | | | | | |
|---|---|---|---|---|---|---|
| TCTCTTTAAG | CTGTAAGGGA | TGTTTCTTAT | GTAGCCAAGG | GCTGAGGTGT | GCTGCCTCAT | 2940 |
| TTATATCAGA | CATAACTTTT | TCTGCAAGGT | TAACCATGAA | ACAATGTTCA | TTGTCAACAT | 3000 |
| ACCAGATAGC | AGTAAAGAAA | GGTGCTAATA | AGTATAACTT | GACAATGTTC | TGCACTTCTA | 3060 |
| ACCCAGAAAA | ACAAAAAATG | ATTATAGAAC | CAGAAGGAGA | CAAATCATAC | TCAGTTGAGG | 3120 |
| CACTTGTAGA | TTCTGTTGCT | GTGCTGGAAC | CAGAAAACAT | AATTGATCAA | AATGACCAAC | 3180 |
| ATGCACACGA | GGAACAGCAA | TATAATTCTG | ACACATCAGT | TTGGAGCTTT | TGGGACTATG | 3240 |
| TTAAAAGCCC | TTTTAACTTT | ATAGCAAGCC | ACTTTGGATC | CTTCTTTGAT | ACAGTCAGAG | 3300 |
| TAGTATTGCT | CATACTCTTT | GTATTTGCTC | TTGCTTACCT | CTGCTCTATT | GTTGCCACAA | 3360 |
| TGTGTAGAGG | CTATGTTAGA | AACAAGTCTT | ACAAGACAAA | ATATATTGAA | GACACTAATG | 3420 |
| ATTATTCTTT | GGTTTCCACG | TCTTCTGGTA | AAGACACCAT | CACTAGAAGA | AGACCTCCTC | 3480 |
| TAGACTTCAG | CGGTATATGA | TTAAATTCAT | TGGAATATAC | ACCAAATGTG | TTTTAAATTA | 3540 |
| AATAAGGCAG | AATGATTGTA | ATCAAATAAA | TTTAATTTGT | CTAAATAAGT | GTTAAATAAG | 3600 |
| CAAACTATAT | AAAAAATATA | AAAATAATAA | AATAAAAAT | CAACAAAAAC | AAATAAAATG | 3660 |
| TATAAAAACA | AATAAAAAGG | TCTTAGACCA | AATCTGGCCG | GAGCCTTATT | TATTTACAAA | 3720 |
| AAAAATTTTT | TTGGTTTTTT | TCAACTTTTT | TCTATTTTTT | GCTTTTGTT | TGTTTTGTT | 3780 |
| TTTGTTTTTG | TTTTTTGTTT | ATTTTTTCTT | TTTTCTTTTT | TGGTTTTTGA | TTTGTTTTTA | 3840 |
| AACACAAATA | CATATATATT | TTATACTTCT | ATATATATAT | ATATATATAG | TTTTTTATCT | 3900 |
| TGCTTTATTT | TTTACTTAAA | CATTCAAAAT | ATTATGAACA | ATATATATTA | TTTATTATTA | 3960 |
| AATGAAAACA | TATTTAGATT | TCATTATCAA | ATGATATCTC | TATCTTGTTA | TCAGTAACAT | 4020 |
| TCTCCTCTTC | TTCAACAGAT | TTCTCTAAAT | TAGCACTTAG | CTCTGCAAGT | TGTCTTCTAA | 4080 |
| TTTGCTTTTC | AGAATTGCCT | TTAGGTATGA | TTAACTTGCA | GGCTTCAATG | AAGGCTTGCG | 4140 |
| ATTTGGCTCT | AATAGCCCTA | TTGATGGGTA | TTATCATGCA | GCTTTATCC | AGATCTGCTC | 4200 |
| TTGGTGAATC | ACAGAATTCT | TTTGTCCAAG | AATACATGAC | ACTAGCAAAA | GAAACATCTT | 4260 |
| TCTTGTAAAC | TTGATCACAT | AATAAATGAA | GCTGAACACA | ATTCTCTGAA | GTGTTGTTAA | 4320 |
| CTTTTGGAAT | GGACCAATTT | AGATAAAAAA | CAAAACATAT | AGGATCTTTA | ATGCTTCCTT | 4380 |
| GCCCTTTCAA | AACAGTTCTG | GCATTAACAC | TCTTGTTAGG | ATCAATTAAA | GCTACAGCCA | 4440 |
| ATTTCCCATC | AGGATCAGCT | ATAGTAGGGC | ATATCCAGAT | AACTATCCTT | GAGATCATCA | 4500 |
| TGTATTGTTT | TCTGCTATCC | CAGGTTGGAT | GTATCTTAAT | TATCTTGGTT | GCAGCTTTAT | 4560 |
| CACCATTACC | TACAAAAAGA | TCATTTTTCC | AGCTGGAGAT | ATGATGATTT | GTATCAACAA | 4620 |
| TCATTCTAGC | AGAAAGATCA | TAAGACTCTG | ATTCAGATAT | CTGGTCAGAC | TCATATGTGC | 4680 |
| CTAGTGATGA | GGTGCCTGTA | TTGTTCATCA | AAATCTTCCC | TTTAGAGCTA | TCCATGGCTC | 4740 |
| TTTGGAGAAC | TTCCTTGTTG | TTGTGATTAG | CAGAAGGATT | GTGTACAACA | ATGTCTGCTC | 4800 |
| CTTGTTTAGA | GAGGGTAGTT | GTAACCCTAG | GGTGATCTAG | CTCCCTGCTG | CTAGATGATC | 4860 |
| TGAGTGATTT | GAAAAAACTA | TTCATCTCTG | GACGGTAGAT | TAAGAATTAA | AATATTGAGA | 4920 |
| AGATAATGAT | TGAATTCGGC | TAGATATAAT | TTTGATGCAC | TGATTGCTCT | | 4970 |

( 2 ) INFORMATION FOR SEQ ID NO:21:

( i ) SEQUENCE CHARACTERISTICS:
        ( A ) LENGTH: 3414 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
ATGAAAATTC    TAAAGATGTG    CGAGTTACTT    GTTAAAATTA    GTGTATGTAC    ACTAGTTGTT      60
ACTTCTGTTA    TCTTATCCTT    TATGGCATTA    AAGGAGACAG    ATGCAAAGAT    TCATGTTGAA     120
AGGGGCGATC    ATCCAGAAAT    TTATGATGAA    GCTTATTATG    ACCGTTCTGT    AGATCATAAA     180
AATGAAATTC    TAGATACTTT    GGCTGAAATG    CTCCAGAATG    CAACAGGTAA    AACCCTTAGA     240
CCAACACGAG    ATACTCAAAC    TGTTCTTGCC    AATAATGAGG    TACCTCAATC    TCCAAGTGGA     300
TTGTCTTCTA    CACCAACAAC    TATATCAGTT    ATGGATTTAC    CAAATCCATG    CCTAAATGCT     360
TCAAGTTTGA    CTTGTAGCAT    TAAAGGAGTT    TCAACATTCA    ATGTTTATTA    CCAAGTAGAA     420
AGCAATGGTG    TTATATATTC    ATGTATCAGT    GACACTATAA    CTAAATTGGG    AAACTGTGAA     480
GGATCTTCTG    AATTGCCAAG    AAGCTTTGAA    ACTGTTCCAG    TTGTACCAAT    AACAAAAATC     540
GATAACAAAA    GGAAATTATC    TATAGGAACT    AAATTCTATA    TAATTGAAAG    TTTGGAGAAT     600
TACAATTATC    CAATCATGTA    CAATTCTAGA    CCAACTAATG    GCACAGTCTC    TCTCCAGAGT     660
GTGAAATTCT    CAGGTGATTG    TAAAATATCA    AAAACAAACA    TAGTTAATTC    TTATACAGTT     720
TCATTAACTA    CACCTGAGAA    AATCATGGGT    TACGTCGTCA    AAAGAGAAGG    AAGTGACATG     780
AGCCATTCCA    TAATAAGCTT    CTCTGGCTCA    GTTAGTTTGA    CTTTCACAGA    AGAAAATATG     840
GATGGTAAGC    ATAACCTATT    GTGCGGTGAC    AAGTCTTCTA    AAGTTCCTTT    AGTGGACAAA     900
AGAGTTAGAG    ATTGTATTAT    AAAGTACTCC    AAAAATATTT    ACAAACAAAC    TGCTTGCATC     960
AACTTCTCAT    GGTTTAGATT    GATCATGATT    GCTCTGATTG    TCTATTTCCC    TATAAGGTAC    1020
TTGGTAAACA    AAACATCTAA    AACACTGTTC    TATGGGTATG    ATCTTCTGGG    ATTGATAACG    1080
TATCCTATAC    TACTACTGAT    AAATTATTTA    TGGTCTTATT    TTCCCTTGAA    ATGTAAGGTC    1140
TGTGGAAATT    TATGTTTGGT    AACCCATGAA    TGCTCAAAAT    TATGCATTTG    TAACAAAAAC    1200
AAAGCCTCTG    AAGAACACTC    AGAAGAATGT    CCTATAATAA    CTAGAACAGC    AGAGAAGAAT    1260
AAAAAATACA    ACTGGGCTAG    CATTGAATGG    TTCCATTTGA    TAGTTAATAC    AAAAATAGGC    1320
CTCTCTTTCC    TAAAAGCAGT    CACAGAAACT    TGATAGGAT    TTCTGATTTT    GTCACAGATG    1380
CCTATGTCTA    TGGCTCAAAC    TGCTCAGTGT    TTGGATAGCT    GTTATTATGT    CCCTGGTTGT    1440
GACCGCTTTG    TTACAAACAG    ATATGACAAA    TGTCCTGAAA    AAGACCAATG    CTTCTGTGCT    1500
ATTAAAGAAA    ATTCTATTGT    AGAATCTAAC    TTTCTAACCA    ATGTTGTGAC    AGAAGGTCCT    1560
ATGGATTGTA    TACCTTATCA    AGAATGCAAA    GGCAGGATAA    CTGAAAATGC    TTTAGTAACT    1620
TTTGTCAAAT    GCAGATTTGG    TTGTGAGTAT    GCCTCTATTT    TCCAAAGCAA    GCCTTTAGAT    1680
AATGGGTTCT    TAGAATATTC    TGGTGACACA    TTGGGATTGA    ATGCTGTGAA    TCTACACTTC    1740
ATGAAAAGGC    TTAGGAATGG    TATAATTGAT    TTCTACAATA    AAACTGAAAA    ATATGGATAC    1800
ATTTCTGGAG    ATGCACTTAA    ATCTAATGAA    TCAGACATAC    CTGAAAGCAT    TTTTCCAAGA    1860
AAATCTCTCA    TATTTGACTC    GGTGATAGAT    GGAAATATA    GATACATGAT    AGAAGAATCT    1920
TTATTATCAG    GTGGGGGCAC    AGTTTTCTCT    CTTAATGACA    AAAGTTCTAG    CACTGCTCAG    1980
AAGTTTGTTG    TTTATATTAA    AAAAGTTAGA    ATACAGTATG    ATGTTTCTGA    ACAATACACT    2040
ACAGCTCCTA    TACAAAGCAC    CCACACTGAT    TTCTTTTCAA    CATGCACAGG    TAAATGCTCA    2100
GATTGCAGAA    AAGAACAACC    GATAACTGGG    TATCAAGATT    TCTGCATAAC    ACCAACATCT    2160
TACTGGGGTT    GTGAAGAGGT    TTGGTGTTTG    GCTATCAATG    AAGGAGCCAC    TTGTGGGTTT    2220
TGTAGAAATG    TGTATGATAT    GGATCAATCT    TTCAGGATTT    ATTCTGTTAT    TAAATCAACA    2280
ATCAAGTCTG    AAGTATGTAT    ATCTGGATTT    GTGGGAGCAA    AGTGTTTCAC    TGTATCTGAG    2340
```

| | | | | | |
|---|---|---|---|---|---|
| GAAGTCCCAT | CTGAATCAGG | ATATTTCCAG | GCTGATATAT | TAGCGGATTT | CCATAATGAT | 2400 |
| GGCTTAACAA | TAGGCCAGCT | GATAGCTCAT | GGACCTGATA | GTCACGTATA | TGCGGGAAAC | 2460 |
| ATAGCTAGAT | TAAATAATCC | ATCAAAATG | TTTGGTCATC | CTCAACTTTC | ACACCAAGGT | 2520 |
| GATCCCATTT | TCTCTAAGAA | AACATTAGAT | ACAAACGATC | TGTCCTGGGA | TTGTTCAGCA | 2580 |
| ATTGGTAAAA | AAACAATTAC | GATAAAATCA | TGTGGTTATG | ACACATACAG | ATTTAAAACA | 2640 |
| GGTTTGAACC | AAATATCGGA | CATTCCAGTT | CAGTTACTG | ACCAGAATAG | TTTTATATG | 2700 |
| GAAAAGATCT | TTAGTCTAGG | TAAGCTTAAA | ATTGTTTTGG | ATCTACCTTC | TGAATTGTTT | 2760 |
| AAAACTGTAC | CAAAAAAGCC | TATATTGAGT | TCTGTCTCTT | TAAGCTGTAA | GGGATGTTTC | 2820 |
| TTATGTAGCC | AAGGGCTGAG | GTGTGCTGCC | TCATTTATAT | CAGACATAAC | TTTTCTGCA | 2880 |
| AGGTTAACCA | TGAAACAATG | TTCATTGTCA | ACATACCAGA | TAGCAGTAAA | GAAGGTGCT | 2940 |
| AATAAGTATA | ACTTGACAAT | GTTCTGCACT | TCTAACCCAG | AAAAACAAAA | AATGATTATA | 3000 |
| GAACCAGAAG | GAGACAAATC | ATACTCAGTT | GAGGCACTTG | TAGATTCTGT | TGCTGTGCTG | 3060 |
| GAACCAGAAA | ACATAATTGA | TCAAAATGAC | CAACATGCAC | ACGAGGAACA | GCAATATAAT | 3120 |
| TCTGACACAT | CAGTTTGGAG | CTTTTGGGAC | TATGTTAAAA | GCCCTTTAA | CTTTATAGCA | 3180 |
| AGCCACTTTG | GATCCTTCTT | TGATACAGTC | AGAGTAGTAT | TGCTCATACT | CTTTGTATTT | 3240 |
| GCTCTTGCTT | ACCTCTGCTC | TATTGTTGCC | ACAATGTGTA | GAGGCTATGT | TAGAAACAAG | 3300 |
| TCTTACAAGA | CAAAATATAT | TGAAGACACT | AATGATTATT | CTTTGGTTTC | CACGTCTTCT | 3360 |
| GGTAAAGACA | CCATCACTAG | AAGAAGACCT | CCTCTAGACT | TCAGCGGTAT | ATGA | 3414 |

( 2 ) INFORMATION FOR SEQ ID NO:22:

( i ) SEQUENCE CHARACTERISTICS:
        ( A ) LENGTH: 912 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

| | | | | | |
|---|---|---|---|---|---|
| TTAGATTTCA | TTATCAAATG | ATATCTCTAT | CTTGTTATCA | GTAACATTCT | CCTCTTCTTC | 60 |
| AACAGATTTC | TCTAAATTAG | CACTTAGCTC | TGCAAGTTGT | CTTCTAATTT | GCTTTTCAGA | 120 |
| ATTGCCTTTA | GGTATGATTA | ACTTGCAGGC | TTCAATGAAG | GCTTGCGATT | TGGCTCTAAT | 180 |
| AGCCCTATTG | ATGGGTATTA | TCATGCAGCT | TTTATCCAGA | TCTGCTCTTG | GTGAATCACA | 240 |
| GAATTCTTTT | GTCCAAGAAT | ACATGACACT | AGCAAAAGAA | ACATCTTTCT | TGTAAACTTG | 300 |
| ATCACATAAT | AAATGAAGCT | GAACACAATT | CTCTGAAGTG | TTGTTAACTT | TTGGAATGGA | 360 |
| CCAATTTAGA | TAAAAAACAA | AACATATAGG | ATCTTAATG | CTTCCTTGCC | CTTTCAAAAC | 420 |
| AGTTCTGGCA | TTAACACTCT | TGTTAGGATC | AATTAAAGCT | ACAGCCAATT | TCCCATCAGG | 480 |
| ATCAGCTATA | GTAGGGCATA | TCCAGATAAC | TATCCTTGAG | ATCATCATGT | ATTGTTTTCT | 540 |
| GCTATCCCAG | GTTGGATGTA | TCTTAATTAT | CTTGGTTGCA | GCTTATCAC | CATTACCTAC | 600 |
| AAAAGATCA | TTTTTCCAGC | TGGAGATATG | ATGATTTGTA | TCAACAATCA | TTCTAGCAGA | 660 |
| AAGATCATAA | GACTCTGATT | CAGATATCTG | GTCAGACTCA | TATGTGCCTA | GTGATGAGGT | 720 |
| GCCTGTATTG | TTCATCAAAA | TCTTCCCTTT | AGAGCTATCC | ATGGCTCTTT | GGAGAACTTC | 780 |
| CTTGTTGTTG | TGATTAGCAG | AAGGATTGTG | TACAACAATG | TCTGCTCCTT | GTTTAGAGAG | 840 |
| GGTAGTTGTA | ACCCTAGGGT | GATCTAGCTC | CCTGCTGCTA | GATGATCTGA | GTGATTTGAA | 900 |
| AAAACTATTC | AT | | | | | 912 |

( 2 ) INFORMATION FOR SEQ ID NO:23:

( i ) SEQUENCE CHARACTERISTICS:
        ( A ) LENGTH: 446 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GGATCCGGAA  CATGGTGGAG  CACGACACGC  TTGTCTACTC  CAAAAATATC  AAAGATACAG      60
TCTCAGAAGA  CCAAAGGGCA  ATTGAGACTT  TTCAACAAAG  TTATTGTGAA  GATAGTGGAA     120
AAGGAAGGTG  GCTCCTACAA  ATGCCATCAT  TGCGATAAAG  GAAAGGCCAT  CGTTGAAGAT     180
GCCTCTGCCG  ACAGTGGTCC  CAAAGATGGA  CCCCCACCCA  CGAGGAGCAT  CGTGGAAAAA     240
GAAGACGTTC  CAACCACGTC  TTCAAAGCAA  GTGGATTGAT  GTGATATCTC  CACTGACGTA     300
AGGGATGACG  CACAATCCCA  CTATCCTTCG  CAAGACCCTT  CCTCTATATA  AGGAAGTTCA     360
TTTCATTTGG  AGAGGACTTT  TTACAACAAT  TACCAACAAC  AACAAACAAC  AAACAACATT     420
ACAATTACTA  TTTACAATTA  CCCGGG                                             446
```

( 2 ) INFORMATION FOR SEQ ID NO:24:

( i ) SEQUENCE CHARACTERISTICS:
        ( A ) LENGTH: 861 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:24:

```
Met  Glu  Thr  Ala  Ser  Asn  Ser  Glu  Arg  Pro  His  Glu  Pro  His  Glu  Leu
 1                   5                        10                       15

Tyr  Ser  Ser  Glu  Arg  Leu  Glu  Ala  Arg  Gly  Ser  Glu  Arg  Ser  Glu  Arg
                20                       25                       30

Ser  Glu  Arg  Ser  Glu  Arg  Ala  Arg  Gly  Gly  Leu  Leu  Glu  Ala  Ser  Pro
               35                        40                       45

His  Ile  Ser  Pro  Arg  Ala  Arg  Gly  Val  Ala  Leu  Thr  His  Arg  Thr  His
          50                        55                      60

Arg  Thr  His  Arg  Leu  Glu  Ser  Glu  Arg  Leu  Tyr  Ser  Gly  Leu  Asn  Gly
65                       70                       75                        80

Leu  Tyr  Ala  Leu  Ala  Ala  Ser  Pro  Ile  Leu  Glu  Val  Ala  Leu  Val  Ala
                    85                        90                       95

Leu  His  Ile  Ser  Ala  Ser  Asn  Pro  Arg  Ser  Glu  Arg  Ala  Leu  Ala  Ala
               100                       105                      110

Ser  Asn  His  Ile  Ser  Ala  Ser  Asn  Ala  Ser  Asn  Leu  Tyr  Ser  Gly  Leu
          115                       120                      125

Val  Ala  Leu  Leu  Glu  Gly  Leu  Asn  Ala  Arg  Gly  Ala  Leu  Ala  Met  Glu
     130                      135                      140

Thr  Ala  Ser  Pro  Ser  Glu  Arg  Ser  Glu  Arg  Leu  Tyr  Ser  Gly  Leu  Tyr
145                      150                      155                      160

Leu  Tyr  Ser  Ile  Leu  Glu  Leu  Glu  Met  Glu  Thr  Ala  Ser  Asn  Ala  Ser
                    165                      170                      175

Asn  Thr  His  Arg  Gly  Leu  Tyr  Thr  His  Arg  Ser  Glu  Arg  Ser  Glu  Arg
               180                      185                      190

Leu  Glu  Gly  Leu  Tyr  Thr  His  Arg  Thr  Tyr  Arg  Gly  Leu  Ser  Glu  Arg
          195                      200                      205

Ala  Ser  Pro  Gly  Leu  Asn  Ile  Leu  Glu  Ser  Glu  Arg  Gly  Leu  Ser  Glu
     210                      215                      220
```

```
Arg  Gly  Leu  Ser  Glu  Arg  Thr  Tyr  Arg  Ala  Ser  Pro  Leu  Glu  Ser  Glu
225                 230                      235                      240

Arg  Ala  Leu  Ala  Ala  Arg  Gly  Met  Glu  Thr  Ile  Leu  Glu  Val  Ala  Leu
               245                      250                      255

Ala  Ser  Pro  Thr  His  Arg  Ala  Ser  Asn  His  Ile  Ser  His  Ile  Ser  Ile
               260                      265                      270

Leu  Glu  Ser  Glu  Arg  Ser  Glu  Arg  Thr  Arg  Pro  Leu  Tyr  Ser  Ala  Ser
               275                      280                      285

Asn  Ala  Ser  Pro  Leu  Glu  Pro  His  Glu  Val  Ala  Leu  Gly  Leu  Tyr  Ala
          290                      295                      300

Ser  Asn  Gly  Leu  Tyr  Ala  Ser  Pro  Leu  Tyr  Ser  Ala  Leu  Ala  Ala  Leu
305                      310                      315                      320

Ala  Thr  His  Arg  Leu  Tyr  Ser  Ile  Leu  Glu  Ile  Leu  Glu  Leu  Tyr  Ser
               325                      330                      335

Ile  Leu  Glu  His  Ile  Ser  Pro  Arg  Thr  His  Arg  Thr  Arg  Pro  Ala  Ser
               340                      345                      350

Pro  Ser  Glu  Arg  Ala  Arg  Gly  Leu  Tyr  Ser  Gly  Leu  Asn  Thr  Tyr  Arg
               355                      360                      365

Met  Glu  Thr  Met  Glu  Thr  Ile  Leu  Glu  Ser  Glu  Arg  Ala  Arg  Gly  Ile
     370                      375                      380

Leu  Glu  Val  Ala  Leu  Ile  Leu  Glu  Thr  Arg  Pro  Ile  Leu  Glu  Cys  Tyr
385                      390                      395                      400

Ser  Pro  Arg  Thr  His  Arg  Ile  Leu  Glu  Ala  Leu  Ala  Ala  Ser  Pro  Pro
                    405                      410                      415

Arg  Ala  Ser  Pro  Gly  Leu  Tyr  Leu  Tyr  Ser  Leu  Glu  Ala  Leu  Ala  Val
               420                      425                      430

Ala  Leu  Ala  Leu  Ala  Leu  Glu  Ile  Leu  Glu  Ala  Ser  Pro  Pro  Arg  Ala
          435                      440                      445

Ser  Asn  Leu  Tyr  Ser  Ser  Glu  Arg  Val  Ala  Leu  Ala  Ser  Asn  Ala  Leu
     450                      455                      460

Ala  Ala  Arg  Gly  Thr  His  Arg  Val  Ala  Leu  Leu  Glu  Leu  Tyr  Ser  Gly
465                      470                      475                      480

Leu  Tyr  Gly  Leu  Asn  Gly  Leu  Tyr  Ser  Glu  Arg  Ile  Leu  Glu  Leu  Tyr
                    485                      490                      495

Ser  Ala  Ser  Pro  Pro  Arg  Ile  Leu  Glu  Cys  Tyr  Ser  Pro  His  Glu  Val
               500                      505                      510

Ala  Leu  Pro  His  Glu  Thr  Tyr  Arg  Leu  Glu  Ala  Ser  Asn  Thr  Arg  Pro
          515                      520                      525

Ser  Glu  Arg  Ile  Leu  Glu  Pro  Arg  Leu  Tyr  Ser  Val  Ala  Leu  Ala  Ser
     530                      535                      540

Asn  Ala  Ser  Asn  Thr  His  Arg  Ser  Glu  Arg  Gly  Leu  Ala  Ser  Asn  Cys
545                      550                      555                      560

Tyr  Ser  Val  Ala  Leu  Gly  Leu  Asn  Leu  Glu  His  Ile  Ser  Leu  Glu  Leu
               565                      570                      575

Glu  Cys  Tyr  Ser  Ala  Ser  Pro  Gly  Leu  Asn  Val  Ala  Leu  Thr  Tyr  Arg
               580                      585                      590

Leu  Tyr  Ser  Leu  Tyr  Ser  Ala  Ser  Pro  Val  Ala  Leu  Ser  Glu  Arg  Pro
               595                      600                      605

His  Glu  Ala  Leu  Ala  Ser  Glu  Arg  Val  Ala  Leu  Met  Glu  Thr  Thr  Tyr
          610                      615                      620

Arg  Ser  Glu  Arg  Thr  Arg  Pro  Thr  His  Arg  Leu  Tyr  Ser  Gly  Leu  Pro
625                      630                      635                      640

His  Glu  Cys  Tyr  Ser  Ala  Ser  Pro  Ser  Glu  Arg  Pro  Arg  Ala  Arg  Gly
```

|     |     |     |     | 645 |     |     |     |     | 650 |     |     |     |     | 655 |     |
| --- | --- | --- | --- | --- | --- | --- | --- | --- | --- | --- | --- | --- | --- | --- | --- |
| Ala | Leu | Ala | Ala | Ser | Pro | Leu | Glu | Ala | Ser | Pro | Leu | Tyr | Ser | Ser | Glu |
|     |     |     | 660 |     |     |     |     | 665 |     |     |     |     | 670 |     |     |
| Arg | Cys | Tyr | Ser | Met | Glu | Thr | Ile | Leu | Glu | Ile | Leu | Glu | Pro | Arg | Ile |
|     |     | 675 |     |     |     | 680 |     |     |     |     | 685 |     |     |     |     |
| Leu | Glu | Ala | Ser | Asn | Ala | Arg | Gly | Ala | Leu | Ala | Ile | Leu | Glu | Ala | Arg |
|     | 690 |     |     |     |     | 695 |     |     |     |     | 700 |     |     |     |     |
| Gly | Ala | Leu | Ala | Leu | Tyr | Ser | Ser | Glu | Arg | Gly | Leu | Asn | Ala | Leu | Ala |
| 705 |     |     |     |     | 710 |     |     |     |     | 715 |     |     |     |     | 720 |
| Pro | His | Glu | Ile | Leu | Glu | Gly | Leu | Ala | Leu | Ala | Cys | Tyr | Ser | Leu | Tyr |
|     |     |     |     | 725 |     |     |     |     | 730 |     |     |     |     | 735 |     |
| Ser | Leu | Glu | Ile | Leu | Glu | Ile | Leu | Glu | Pro | Arg | Leu | Tyr | Ser | Gly | Leu |
|     |     |     | 740 |     |     |     |     | 745 |     |     |     |     | 750 |     |     |
| Tyr | Ala | Ser | Asn | Ser | Glu | Arg | Gly | Leu | Leu | Tyr | Ser | Gly | Leu | Asn | Ile |
|     |     | 755 |     |     |     | 760 |     |     |     |     | 765 |     |     |     |     |
| Leu | Glu | Ala | Arg | Gly | Ala | Arg | Gly | Gly | Leu | Asn | Leu | Glu | Ala | Leu | Ala |
|     | 770 |     |     |     |     | 775 |     |     |     |     | 780 |     |     |     |     |
| Gly | Leu | Leu | Glu | Ser | Glu | Arg | Ala | Leu | Ala | Ala | Ser | Asn | Leu | Glu | Gly |
| 785 |     |     |     |     | 790 |     |     |     |     | 795 |     |     |     |     | 800 |
| Leu | Leu | Tyr | Ser | Ser | Glu | Arg | Val | Ala | Leu | Gly | Leu | Gly | Leu | Gly | Leu |
|     |     |     |     | 805 |     |     |     |     | 810 |     |     |     |     | 815 |     |
| Gly | Leu | Ala | Ser | Asn | Val | Ala | Leu | Thr | His | Arg | Ala | Ser | Pro | Ala | Ser |
|     |     |     | 820 |     |     |     |     | 825 |     |     |     |     | 830 |     |     |
| Asn | Leu | Tyr | Ser | Ile | Leu | Glu | Gly | Leu | Ile | Leu | Glu | Ser | Glu | Arg | Pro |
|     |     | 835 |     |     |     | 840 |     |     |     |     | 845 |     |     |     |     |
| His | Glu | Ala | Ser | Pro | Ala | Ser | Asn | Gly | Leu | Ile | Leu | Glu |     |     |     |
|     | 850 |     |     |     |     | 855 |     |     |     |     | 860 |     |     |     |     |

( 2 ) INFORMATION FOR SEQ ID NO:25:

( i ) SEQUENCE CHARACTERISTICS:
        ( A ) LENGTH: 744 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:25:

| Met | Glu | Thr | Ala | Ser | Asn | Leu | Tyr | Ser | Ala | Leu | Ala | Leu | Tyr | Ser | Ile |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Leu | Glu | Thr | His | Arg | Leu | Tyr | Ser | Gly | Leu | Ala | Ser | Asn | Ile | Leu | Glu |
|     |     |     | 20 |     |     |     |     | 25 |     |     |     |     | 30 |     |     |
| Val | Ala | Leu | Leu | Tyr | Ser | Leu | Glu | Leu | Glu | Thr | His | Arg | Gly | Leu | Asn |
|     |     | 35 |     |     |     | 40 |     |     |     |     | 45 |     |     |     |     |
| Ser | Glu | Arg | Ala | Ser | Pro | Ser | Glu | Arg | Leu | Glu | Gly | Leu | Pro | His | Glu |
|     | 50 |    |     |     |     | 55 |     |     |     |     | 60 |     |     |     |     |
| Gly | Leu | Gly | Leu | Thr | His | Arg | Gly | Leu | Asn | Ala | Ser | Asn | Gly | Leu | Gly |
| 65 |     |     |     |     | 70 |     |     |     |     | 75 |     |     |     |     | 80 |
| Leu | Tyr | Ser | Glu | Arg | Pro | His | Glu | Ala | Ser | Asn | Pro | His | Glu | Thr | His |
|     |     |     |     | 85 |     |     |     |     | 90 |     |     |     |     | 95 |     |
| Arg | Ala | Ser | Pro | Pro | His | Glu | Pro | His | Glu | Thr | His | Arg | Ala | Ser | Asn |
|     |     |     | 100 |     |     |     |     | 105 |     |     |     |     | 110 |     |     |
| Ala | Ser | Asn | Ala | Arg | Gly | Gly | Leu | Leu | Tyr | Ser | Ile | Leu | Glu | Gly | Leu |
|     |     | 115 |     |     |     | 120 |     |     |     |     | 125 |     |     |     |     |
| Asn | Ala | Ser | Asn | Met | Glu | Thr | Thr | His | Arg | Thr | His | Arg | Ala | Leu | Ala |
|     |     | 130 |     |     |     | 135 |     |     |     |     | 140 |     |     |     |     |

```
Ser Glu Arg Cys Tyr Ser Leu Glu Ser Glu Arg Pro His Glu Leu Glu
145                 150                 155                 160

Leu Tyr Ser Ala Ser Asn Ala Arg Gly Gly Leu Asn Ser Glu Arg Ile
                165                 170                 175

Leu Glu Met Glu Thr Ala Arg Gly Val Ala Leu Ile Leu Glu Leu Tyr
            180                 185                 190

Ser Ser Glu Arg Ala Leu Ala Ala Ser Pro His Glu Thr His Arg
        195                 200             205

Pro His Glu Gly Leu Tyr Ser Glu Arg Val Ala Leu Thr His Arg Ile
    210                 215                 220

Leu Glu Leu Tyr Ser Leu Tyr Ser Thr His Arg Ala Arg Gly Ala Ser
225                 230                 235                 240

Asn Ala Ser Asn Ser Glu Arg Gly Leu Ala Arg Gly Val Ala Leu Gly
                245                 250                 255

Leu Tyr Val Ala Leu Ala Ser Asn Ala Ser Pro Met Glu Thr Thr His
            260                 265                 270

Arg Pro His Glu Ala Arg Gly Ala Arg Gly Leu Glu Ala Ser Pro Ala
        275                 280                 285

Leu Ala Met Glu Thr Val Ala Leu Ala Arg Gly Val Ala Leu His Ile
    290                 295                 300

Ser Leu Glu Val Ala Leu Gly Leu Tyr Met Glu Thr Ile Leu Glu Leu
305                 310                 315                 320

Tyr Ser Ala Ser Pro Ala Ser Asn Gly Leu Tyr Ser Glu Arg Ala Leu
                325                 330                 335

Ala Leu Glu Thr His Arg Gly Leu Ala Leu Ala Ile Leu Glu Ala Ser
            340                 345                 350

Asn Ser Glu Arg Leu Glu Pro Arg Ser Glu Arg His Ile Ser Pro Arg
        355                 360                 365

Leu Glu Ile Leu Glu Ala Leu Ala Ser Glu Arg Thr Tyr Arg Gly Leu
    370                 375                 380

Tyr Leu Glu Ala Leu Ala Thr His Arg Thr His Arg Ala Ser Pro Leu
385                 390                 395                 400

Glu Leu Tyr Ser Ser Glu Arg Cys Tyr Ser Val Ala Leu Leu Glu Gly
                405                 410                 415

Leu Tyr Val Ala Leu Leu Glu Leu Glu Gly Leu Tyr Gly Leu Tyr Ser
            420                 425                 430

Glu Arg Leu Glu Pro Arg Leu Glu Ile Leu Glu Ala Leu Ala Ser Glu
        435                 440                 445

Arg Val Ala Leu Leu Glu Ala Ser Asn Pro His Glu Gly Leu Ile Leu
    450                 455                 460

Glu Ala Leu Ala Ala Leu Ala Leu Glu Val Ala Leu Pro Arg Ala Leu
465                 470                 475                 480

Ala Ile Leu Glu Thr Tyr Arg Gly Leu Asn Ala Ser Pro Ala Leu Ala
            485                 490                 495

Leu Tyr Ser His Ile Ser Val Ala Leu Gly Leu Leu Glu Gly Leu Tyr
            500                 505                 510

Ile Leu Glu Ala Ser Pro Met Glu Thr Ser Glu Arg Leu Tyr Ser Pro
        515                 520                 525

His Glu Ser Glu Arg Thr His Arg Leu Tyr Ser Gly Leu Ala Leu Ala
        530                 535                 540

Val Ala Leu Gly Leu Tyr Leu Tyr Ser Val Ala Leu Cys Tyr Ser Thr
545                 550                 555                 560

His Arg Val Ala Leu Leu Glu Leu Tyr Ser Ser Glu Arg Leu Tyr Ser
```

|     |     |     |     | 565 |     |     |     |     | 570 |     |     |     |     | 575 |     |
| --- | --- | --- | --- | --- | --- | --- | --- | --- | --- | --- | --- | --- | --- | --- | --- |
| Gly | Leu | Tyr | Thr | Tyr | Arg | Ser | Glu | Arg | Met | Glu | Thr | Ala | Ser | Asn | Ser |
|     |     |     | 580 |     |     |     |     | 585 |     |     |     |     | 590 |     |     |
| Glu | Arg | Val | Ala | Leu | Gly | Leu | Ile | Leu | Glu | Gly | Leu | Tyr | Leu | Tyr | Ser |
|     |     | 595 |     |     |     | 600 |     |     |     |     |     | 605 |     |     |     |
| Ala | Leu | Ala | Leu | Tyr | Ser | Gly | Leu | Asn | Thr | Tyr | Arg | Ala | Leu | Ala | Ala |
|     | 610 |     |     |     |     | 615 |     |     |     |     | 620 |     |     |     |     |
| Ser | Pro | Ile | Leu | Glu | Leu | Glu | Leu | Tyr | Ser | Ala | Leu | Ala | Cys | Tyr | Ser |
| 625 |     |     |     |     | 630 |     |     |     |     | 635 |     |     |     |     | 640 |
| Ser | Glu | Arg | Pro | Arg | Leu | Tyr | Ser | Ala | Leu | Ala | Leu | Tyr | Ser | Gly | Leu |
|     |     |     |     | 645 |     |     |     |     | 650 |     |     |     |     | 655 |     |
| Tyr | Leu | Glu | Ala | Leu | Ala | Ala | Leu | Ala | Met | Glu | Thr | Ala | Ser | Pro | His |
|     |     |     |     | 660 |     |     |     |     | 665 |     |     |     |     | 670 |     |
| Ile | Ser | Thr | Tyr | Arg | Leu | Tyr | Ser | Gly | Leu | Gly | Leu | Tyr | Leu | Glu | Thr |
|     |     | 675 |     |     |     |     |     | 680 |     |     |     |     | 685 |     |     |
| His | Arg | Ser | Glu | Arg | Ile | Leu | Glu | Thr | Tyr | Arg | Ser | Glu | Arg | Met | Glu |
|     |     |     | 690 |     |     |     | 695 |     |     |     |     | 700 |     |     |     |
| Thr | Pro | His | Glu | Ala | Ser | Asn | Ala | Leu | Ala | Thr | His | Arg | Ile | Leu | Glu |
| 705 |     |     |     |     | 710 |     |     |     |     | 715 |     |     |     |     | 720 |
| Ala | Ser | Pro | Pro | His | Glu | Gly | Leu | Tyr | Leu | Tyr | Ser | Ala | Ser | Asn | Ala |
|     |     |     |     | 725 |     |     |     |     | 730 |     |     |     |     | 735 |     |
| Ser | Pro | Ser | Glu | Arg | Ile | Leu | Glu |     |     |     |     |     |     |     |     |
|     |     |     | 740 |     |     |     |     |     |     |     |     |     |     |     |     |

( 2 ) INFORMATION FOR SEQ ID NO:26:

( i ) SEQUENCE CHARACTERISTICS:
        ( A ) LENGTH: 1261 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:26:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Glu | Thr | Ser | Glu | Arg | Ser | Glu | Arg | Ala | Leu | Ala | Met | Glu | Thr | Thr |
| 1   |     |     |     | 5   |     |     |     |     | 10  |     |     |     |     | 15  |     |
| Tyr | Arg | Gly | Leu | Thr | His | Arg | Ile | Leu | Glu | Ile | Leu | Glu | Leu | Tyr | Ser |
|     |     |     | 20  |     |     |     |     | 25  |     |     |     |     | 30  |     |     |
| Ser | Glu | Arg | Leu | Tyr | Ser | Ser | Glu | Arg | Ser | Glu | Arg | Ile | Leu | Glu | Thr |
|     |     | 35  |     |     |     |     | 40  |     |     |     |     | 45  |     |     |     |
| Arg | Pro | Gly | Leu | Tyr | Thr | His | Arg | Thr | His | Arg | Ser | Glu | Arg | Ser | Glu |
|     | 50  |     |     |     |     | 55  |     |     |     |     | 60  |     |     |     |     |
| Arg | Gly | Leu | Tyr | Leu | Tyr | Ser | Ala | Leu | Ala | Val | Ala | Leu | Val | Ala | Leu |
| 65  |     |     |     |     | 70  |     |     |     |     | 75  |     |     |     |     | 80  |
| Ala | Ser | Pro | Ser | Glu | Arg | Thr | Tyr | Arg | Thr | Arg | Pro | Ile | Leu | Glu | His |
|     |     |     |     | 85  |     |     |     |     | 90  |     |     |     |     | 95  |     |
| Ile | Ser | Ala | Ser | Pro | Gly | Leu | Asn | Ser | Glu | Arg | Ser | Glu | Arg | Gly | Leu |
|     |     |     |     | 100 |     |     |     |     | 105 |     |     |     |     | 110 |     |
| Tyr | Leu | Tyr | Ser | Leu | Tyr | Ser | Leu | Glu | Val | Ala | Leu | Gly | Leu | Ala | Leu |
|     |     |     | 115 |     |     |     |     | 120 |     |     |     |     | 125 |     |     |
| Ala | Gly | Leu | Asn | Leu | Glu | Thr | Tyr | Arg | Ser | Glu | Arg | Ala | Ser | Pro | Ser |
|     |     | 130 |     |     |     |     | 135 |     |     |     |     | 140 |     |     |     |
| Glu | Arg | Ala | Arg | Gly | Ser | Glu | Arg | Leu | Tyr | Ser | Thr | His | Arg | Ser | Glu |
| 145 |     |     |     |     | 150 |     |     |     |     | 155 |     |     |     |     | 160 |
| Arg | Pro | His | Glu | Cys | Tyr | Ser | Thr | Tyr | Arg | Thr | His | Arg | Gly | Leu | Tyr |
|     |     |     |     | 165 |     |     |     |     | 170 |     |     |     |     | 175 |     |

```
Leu Tyr Ser Val Ala Leu Gly Leu Tyr Pro His Glu Leu Glu Pro Arg
            180                 185                 190

Thr His Arg Gly Leu Gly Leu Leu Tyr Ser Gly Leu Ile Leu Glu Ile
        195                 200                 205

Leu Glu Val Ala Leu Ala Arg Gly Cys Tyr Ser Pro His Glu Val Ala
    210                 215                 220

Leu Pro Arg Ile Leu Glu Pro His Glu Ala Ser Pro Ala Ser Pro Ile
225                 230                 235                 240

Leu Glu Ala Ser Pro Leu Glu Ala Ser Asn Pro His Glu Ser Glu Arg
                245                 250                 255

Pro His Glu Ser Glu Arg Gly Leu Tyr Ala Ser Asn Val Ala Leu Val
            260                 265                 270

Ala Leu Gly Leu Ile Leu Glu Leu Glu Val Ala Leu Ala Arg Gly Ser
        275                 280                 285

Glu Arg Ala Ser Asn Thr His Arg Thr His Arg Ala Ser Asn Thr His
    290                 295                 300

Arg Ala Ser Asn Gly Leu Tyr Val Ala Leu Leu Tyr Ser His Ile Ser
305                 310                 315                 320

Gly Leu Asn Gly Leu Tyr His Ile Ser Leu Glu Leu Tyr Ser Val Ala
                325                 330                 335

Leu Leu Glu Ser Glu Arg Ser Glu Arg Gly Leu Asn Leu Glu Leu Glu
            340                 345                 350

Ala Arg Gly Met Glu Thr Leu Glu Gly Leu Gly Leu Gly Leu Asn Ile
            355                 360                 365

Leu Glu Ala Leu Ala Val Ala Leu Pro Arg Gly Leu Ile Leu Glu Thr
    370                 375                 380

His Arg Ser Glu Arg Ala Arg Gly Pro His Glu Gly Leu Tyr Leu Glu
385                 390                 395                 400

Leu Tyr Ser Gly Leu Ser Glu Arg Ala Ser Pro Ile Leu Glu Pro His
                405                 410                 415

Glu Pro Arg Pro Arg Ala Ser Asn Ala Ser Asn Pro His Glu Ile Leu
            420                 425                 430

Glu Gly Leu Ala Leu Ala Ala Leu Ala Ala Ser Asn Leu Tyr Ser Gly
            435                 440                 445

Leu Tyr Ser Glu Arg Leu Glu Ser Glu Arg Cys Tyr Ser Val Ala Leu
        450                 455                 460

Leu Tyr Ser Gly Leu Val Ala Leu Leu Glu Pro His Glu Ala Ser Pro
465                 470                 475                 480

Val Ala Leu Leu Tyr Ser Thr Tyr Arg Ser Glu Arg Ala Ser Asn Ala
                485                 490                 495

Ser Asn Gly Leu Asn Ser Glu Arg Met Glu Thr Gly Leu Tyr Leu Tyr
            500                 505                 510

Ser Val Ala Leu Ser Glu Arg Val Ala Leu Leu Glu Ser Glu Arg Pro
        515                 520                 525

Arg Thr His Arg Ala Arg Gly Ser Glu Arg Val Ala Leu His Ile Ser
        530                 535                 540

Gly Leu Thr Arg Pro Leu Glu Thr Tyr Arg Thr His Arg Leu Glu Leu
545                 550                 555                 560

Tyr Ser Pro Arg Val Ala Leu Pro His Glu Ala Ser Asn Gly Leu Asn
                565                 570                 575

Ser Glu Arg Gly Leu Asn Thr His Arg Ala Ser Asn Ala Ser Asn Ala
            580                 585                 590

Arg Gly Thr His Arg Val Ala Leu Ala Ser Asn Thr His Arg Leu Glu
```

```
                    595                         600                         605
Ala Leu Ala Val Ala Leu Leu Tyr Ser Ser Glu Arg Leu Glu Ala Leu
            610                         615                         620
Ala Met Glu Thr Ser Glu Arg Ala Leu Ala Thr His Arg Ser Glu Arg
625                         630                         635                         640
Ala Ser Pro Leu Glu Met Glu Thr Ser Glu Arg Ala Ser Pro Thr His
                        645                         650                         655
Arg His Ile Ser Ser Glu Arg Pro His Glu Val Ala Leu Ala Arg Gly
                660                         665                         670
Leu Glu Ala Ser Asn Ala Ser Asn Ala Ser Asn Leu Tyr Ser Pro Arg
            675                         680                         685
Pro His Glu Leu Tyr Ser Ile Leu Glu Ser Glu Arg Leu Glu Thr Arg
        690                         695                         700
Pro Met Glu Thr Ala Arg Gly Ile Leu Glu Pro Arg Leu Tyr Ser Ile
705                         710                         715                         720
Leu Glu Met Glu Thr Leu Tyr Ser Ser Glu Arg Ala Ser Asn Thr His
                        725                         730                         735
Arg Thr Tyr Arg Ser Glu Arg Ala Arg Gly Pro His Glu Pro His Glu
                740                         745                         750
Thr His Arg Leu Glu Ser Glu Arg Ala Ser Pro Gly Leu Ser Glu Arg
            755                         760                         765
Ser Glu Arg Pro Arg Leu Tyr Ser Gly Leu Thr Tyr Arg Thr Tyr Arg
        770                         775                         780
Ile Leu Glu Ser Glu Arg Ile Leu Glu Gly Leu Asn Cys Tyr Ser Leu
785                         790                         795                         800
Glu Pro Arg Ala Ser Asn His Ile Ser Ala Ser Asn Ala Ser Asn Val
                        805                         810                         815
Ala Leu Gly Leu Thr His Arg Val Ala Leu Ile Leu Glu Gly Leu Thr
                820                         825                         830
Tyr Arg Ala Ser Asn Pro His Glu Ala Ser Pro Gly Leu Asn Ser Glu
            835                         840                         845
Arg Ala Ser Asn Leu Glu Pro His Glu Leu Glu Ala Ser Asn Gly Leu
        850                         855                         860
Asn Leu Glu Leu Glu Leu Glu Ala Leu Ala Val Ala Leu Ile Leu Glu
865                         870                         875                         880
His Ile Ser Leu Tyr Ser Ile Leu Glu Gly Leu Met Glu Thr Ala Ser
                        885                         890                         895
Asn Pro His Glu Ser Glu Arg Ala Ser Pro Leu Glu Leu Tyr Ser Gly
                900                         905                         910
Leu Pro Arg Thr Tyr Arg Ala Ser Asn Val Ala Leu Ile Leu Glu His
            915                         920                         925
Ile Ser Ala Ser Pro Met Glu Thr Ser Glu Arg Thr Tyr Arg Pro Arg
        930                         935                         940
Gly Leu Asn Ala Arg Gly Ile Leu Glu Val Ala Leu His Ile Ser Ser
945                         950                         955                         960
Glu Arg Leu Glu Leu Glu Gly Leu Ile Leu Glu His Ile Ser Thr His
                        965                         970                         975
Arg Gly Leu Leu Glu Ala Leu Ala Gly Leu Asn Thr His Arg Val Ala
                980                         985                         990
Leu Cys Tyr Ser Ala Ser Pro Ser Glu Arg Val Ala Leu Gly Leu Asn
            995                         1000                        1005
Gly Leu Asn Ala Ser Pro Met Glu Thr Ile Leu Glu Val Ala Leu Pro
        1010                        1015                        1020
```

|   |   |   |   |   |   |   |   |   |   |   |   |   |   |   |
|---|---|---|---|---|---|---|---|---|---|---|---|---|---|---|
| His | Glu | Thr | His | Arg | Ile | Leu | Glu | Ala | Ser | Asn | Gly | Leu | Pro | Arg | Ala |
| 1025 |   |   |   |   | 1030 |   |   |   |   | 1035 |   |   |   |   | 1040 |

```
His Glu Thr His Arg Ile Leu Glu Ala Ser Asn Gly Leu Pro Arg Ala
1025                1030                1035                1040

Ser Pro Leu Glu Leu Tyr Ser Pro Arg Leu Tyr Ser Leu Tyr Ser Pro
                1045                1050                1055

His Glu Gly Leu Leu Glu Gly Leu Tyr Leu Tyr Ser Leu Tyr Ser Thr
                1060                1065                1070

His Arg Leu Glu Ala Ser Asn Thr Tyr Arg Ser Glu Arg Gly Leu Ala
                1075                1080                1085

Ser Pro Gly Leu Tyr Thr Tyr Arg Gly Leu Tyr Ala Arg Gly Leu Tyr
                1090                1095                1100

Ser Thr Tyr Arg Pro His Glu Leu Glu Ser Glu Arg Gly Leu Asn Thr
1105                1110                1115                1120

His Arg Leu Glu Leu Tyr Ser Ser Glu Arg Leu Glu Pro Arg Ala Arg
                1125                1130                1135

Gly Ala Ser Asn Ser Glu Arg Gly Leu Asn Thr His Arg Met Glu Thr
                1140                1145                1150

Ser Glu Arg Thr Tyr Arg Leu Glu Ala Ser Pro Ser Glu Arg Ile Leu
                1155                1160                1165

Glu Gly Leu Asn Met Glu Thr Pro Arg Ala Ser Pro Thr Arg Pro Leu
                1170                1175                1180

Tyr Ser Pro His Glu Ala Ser Pro Thr Tyr Arg Ala Leu Ala Ala Leu
1185                1190                1195                1200

Ala Gly Leu Tyr Gly Leu Ile Leu Glu Leu Tyr Ser Ile Leu Glu Ser
                1205                1210                1215

Glu Arg Pro Arg Ala Arg Gly Ser Glu Arg Gly Leu Ala Ser Pro Val
                1220                1225                1230

Ala Leu Leu Glu Leu Tyr Ser Ala Leu Ala Ile Leu Glu Ser Glu Arg
                1235                1240                1245

Leu Tyr Ser Leu Glu Ala Ser Pro Leu Glu Ala Ser Asn
                1250                1255                1260
```

( 2 ) INFORMATION FOR SEQ ID NO:27:

( i ) SEQUENCE CHARACTERISTICS:
        ( A ) LENGTH: 3218 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:27:

```
Met Glu Thr Leu Tyr Ser Ile Leu Glu Leu Glu Leu Tyr Ser Met Glu
1               5                   10                  15

Thr Cys Tyr Ser Gly Leu Leu Glu Leu Glu Val Ala Leu Leu Tyr Ser
                20                  25                  30

Ile Leu Glu Ser Glu Arg Val Ala Leu Cys Tyr Ser Thr His Arg Leu
                35                  40                  45

Glu Val Ala Leu Val Ala Leu Thr His Arg Ser Glu Arg Val Ala Leu
                50                  55                  60

Ile Leu Glu Leu Glu Ser Glu Arg Pro His Glu Met Glu Thr Ala Leu
65                  70                  75                  80

Ala Leu Glu Leu Tyr Ser Gly Leu Thr His Arg Ala Ser Pro Ala Leu
                85                  90                  95

Ala Leu Tyr Ser Ile Leu Glu His Ile Ser Val Ala Leu Gly Leu Ala
                100                 105                 110

Arg Gly Gly Leu Tyr Ala Ser Pro His Ile Ser Pro Arg Gly Leu Ile
```

-continued

```
                    115                           120                           125
   Leu Glu Thr Tyr Arg Ala Ser Pro Gly Leu Ala Leu Ala Thr Tyr Arg
       130                           135                       140
   Thr Tyr Arg Ala Ser Pro Ala Arg Gly Ser Glu Arg Val Ala Leu Ala
   145                       150                       155                       160
   Ser Pro His Ile Ser Leu Tyr Ser Ala Ser Asn Gly Leu Ile Leu Glu
                       165                       170                           175
   Leu Glu Ala Ser Pro Thr His Arg Leu Glu Ala Leu Ala Gly Leu Met
                   180                           185                   190
   Glu Thr Leu Glu Gly Leu Asn Ala Ser Asn Ala Leu Ala Thr His Arg
               195                       200                       205
   Gly Leu Tyr Leu Tyr Ser Thr His Arg Leu Glu Ala Arg Gly Pro Arg
           210                           215                   220
   Thr His Arg Ala Arg Gly Ala Ser Pro Thr His Arg Gly Leu Asn Thr
   225                           230                       235                   240
   His Arg Val Ala Leu Leu Glu Ala Leu Ala Ala Ser Asn Ala Ser Asn
                       245                       250                       255
   Gly Leu Val Ala Leu Pro Arg Gly Leu Asn Ser Glu Arg Pro Arg Ser
                   260                       265                   270
   Glu Arg Gly Leu Tyr Leu Glu Ser Glu Arg Ser Glu Arg Thr His Arg
               275                       280                       285
   Pro Arg Thr His Arg Thr His Arg Ile Leu Glu Ser Glu Arg Val Ala
           290                       295                   300
   Leu Met Glu Thr Ala Ser Pro Leu Glu Pro Arg Ala Ser Asn Pro Arg
   305                           310                       315                   320
   Cys Tyr Ser Leu Glu Ala Ser Asn Ala Leu Ala Ser Glu Arg Ser Glu
                       325                       330                       335
   Arg Leu Glu Thr His Arg Cys Tyr Ser Ser Glu Arg Ile Leu Glu Leu
                   340                       345                   350
   Tyr Ser Gly Leu Tyr Val Ala Leu Ser Glu Arg Thr His Arg Pro His
               355                       360                       365
   Glu Ala Ser Asn Val Ala Leu Thr Tyr Arg Thr Tyr Arg Gly Leu Asn
           370                       375                   380
   Val Ala Leu Gly Leu Ser Glu Arg Ala Ser Asn Gly Leu Tyr Val Ala
   385                           390                       395                   400
   Leu Ile Leu Glu Thr Tyr Arg Ser Glu Arg Cys Tyr Ser Ile Leu Glu
                       405                       410                       415
   Ser Glu Arg Ala Ser Pro Thr His Arg Ile Leu Glu Thr His Arg Leu
                   420                       425                   430
   Tyr Ser Leu Glu Gly Leu Tyr Ala Ser Asn Cys Tyr Ser Gly Leu Gly
               435                       440                   445
   Leu Tyr Ser Glu Arg Ser Glu Arg Gly Leu Leu Glu Pro Arg Ala Arg
           450                       455                   460
   Gly Ser Glu Arg Pro His Glu Gly Leu Thr His Arg Val Ala Leu Pro
   465                       470                       475                   480
   Arg Val Ala Leu Val Ala Leu Pro Arg Ile Leu Glu Thr His Arg Leu
                   485                       490                       495
   Tyr Ser Ile Leu Glu Ala Ser Pro Ala Ser Asn Leu Tyr Ser Ala Arg
                   500                       505                   510
   Gly Leu Tyr Ser Leu Glu Ser Glu Arg Ile Leu Glu Gly Leu Tyr Thr
               515                       520                   525
   His Arg Leu Tyr Ser Pro His Glu Thr Tyr Arg Ile Leu Glu Ile Leu
           530                       535                   540
```

```
Glu  Gly  Leu  Ser  Glu  Arg  Leu  Glu  Gly  Leu  Ala  Ser  Asn  Thr  Tyr  Arg
545                      550                 555                      560

Ala  Ser  Asn  Thr  Tyr  Arg  Pro  Arg  Ile  Leu  Glu  Met  Glu  Thr  Thr  Tyr
               565                 570                           575

Arg  Ala  Ser  Asn  Ser  Glu  Arg  Ala  Arg  Gly  Pro  Arg  Thr  His  Arg  Ala
               580                 585                      590

Ser  Asn  Gly  Leu  Tyr  Thr  His  Arg  Val  Ala  Leu  Ser  Glu  Arg  Leu  Glu
          595                 600                      605

Gly  Leu  Asn  Ser  Glu  Arg  Val  Ala  Leu  Leu  Tyr  Ser  Pro  His  Glu  Ser
610                      615                      620

Glu  Arg  Gly  Leu  Tyr  Ala  Ser  Pro  Cys  Tyr  Ser  Leu  Tyr  Ser  Ile  Leu
625                 630                      635                           640

Glu  Ser  Glu  Arg  Leu  Tyr  Ser  Thr  His  Arg  Ala  Ser  Asn  Ile  Leu  Glu
                    645                 650                           655

Val  Ala  Leu  Ala  Ser  Asn  Ser  Glu  Arg  Thr  Tyr  Arg  Thr  His  Arg  Val
               660                 665                      670

Ala  Leu  Ser  Glu  Arg  Leu  Glu  Thr  His  Arg  Thr  His  Arg  Pro  Arg  Gly
          675                      680                      685

Leu  Leu  Tyr  Ser  Ile  Leu  Glu  Met  Glu  Thr  Gly  Leu  Tyr  Thr  Tyr  Arg
690                           695                      700

Val  Ala  Leu  Val  Ala  Leu  Leu  Tyr  Ser  Ala  Arg  Gly  Gly  Leu  Gly  Leu
705                 710                      715                           720

Tyr  Ser  Glu  Arg  Ala  Ser  Pro  Met  Glu  Thr  Ser  Glu  Arg  His  Ile  Ser
                    725                 730                      735

Ser  Glu  Arg  Ile  Leu  Glu  Ile  Leu  Ser  Glu  Arg  Pro  His  Glu  Ser
               740                      745                 750

Glu  Arg  Gly  Leu  Tyr  Ser  Glu  Arg  Val  Ala  Leu  Ser  Glu  Arg  Leu  Glu
          755                      760                      765

Thr  His  Arg  Pro  His  Glu  Thr  His  Arg  Gly  Leu  Gly  Leu  Ala  Ser  Asn
     770                 775                      780

Met  Glu  Thr  Ala  Ser  Pro  Gly  Leu  Tyr  Leu  Tyr  Ser  His  Ile  Ser  Ala
785                      790                 795                           800

Ser  Asn  Leu  Glu  Leu  Glu  Cys  Tyr  Ser  Gly  Leu  Tyr  Ala  Ser  Pro  Leu
               805                      810                      815

Tyr  Ser  Ser  Glu  Arg  Ser  Glu  Arg  Leu  Tyr  Ser  Val  Ala  Leu  Pro  Arg
               820                 825                      830

Leu  Glu  Val  Ala  Leu  Ala  Ser  Pro  Leu  Tyr  Ser  Ala  Arg  Gly  Val  Ala
          835                      840                 845

Leu  Ala  Arg  Gly  Ala  Ser  Pro  Cys  Tyr  Ser  Ile  Leu  Glu  Ile  Leu  Glu
     850                      855                      860

Leu  Tyr  Ser  Thr  Tyr  Arg  Ser  Glu  Arg  Leu  Tyr  Ser  Ala  Ser  Asn  Ile
865                      870                      875                      880

Leu  Glu  Thr  Tyr  Arg  Leu  Tyr  Ser  Gly  Leu  Asn  Thr  His  Arg  Ala  Leu
                    885                      890                      895

Ala  Cys  Tyr  Ser  Ile  Leu  Glu  Ala  Ser  Asn  Pro  His  Glu  Ser  Glu  Arg
               900                 905                      910

Thr  Arg  Pro  Pro  His  Glu  Ala  Arg  Gly  Leu  Glu  Ile  Leu  Glu  Met  Glu
          915                      920                      925

Thr  Ile  Leu  Glu  Ala  Leu  Ala  Leu  Glu  Ile  Leu  Glu  Val  Ala  Leu  Thr
     930                      935                      940

Tyr  Arg  Pro  His  Glu  Pro  Arg  Ile  Leu  Glu  Ala  Arg  Gly  Thr  Tyr  Arg
945                      950                      955                      960

Leu  Glu  Val  Ala  Leu  Ala  Ser  Asn  Leu  Tyr  Ser  Thr  His  Arg  Ser  Glu
               965                      970                      975
```

```
Arg Leu Tyr Ser Thr His Arg Leu Glu Pro His Glu Thr Tyr Arg Gly
            980                 985                 990
Leu Tyr Thr Tyr Arg Ala Ser Pro Glu Leu Glu Gly Leu Tyr Leu
            995                1000                1005
Glu Ile Leu Glu Thr His Arg Thr Tyr Arg Pro Arg Ile Leu Glu Leu
    1010                1015                1020
Glu Leu Glu Leu Glu Ile Leu Glu Ala Ser Asn Thr Tyr Arg Leu Glu
1025                1030                1035                1040
Thr Arg Pro Ser Glu Arg Thr Tyr Arg Pro His Glu Pro Arg Leu Glu
                1045                1050                1055
Leu Tyr Ser Cys Tyr Ser Leu Tyr Ser Val Ala Leu Cys Tyr Ser Gly
            1060                1065                1070
Leu Tyr Ala Ser Asn Leu Glu Cys Tyr Ser Leu Glu Val Ala Leu Thr
            1075                1080                1085
His Arg His Ile Ser Gly Leu Cys Tyr Ser Ser Glu Arg Leu Tyr Ser
            1090                1095                1100
Leu Glu Cys Tyr Ser Ile Leu Glu Cys Tyr Ser Ala Ser Asn Leu Tyr
1105                1110                1115                1120
Ser Ala Ser Asn Leu Tyr Ser Ala Leu Ala Ser Glu Arg Gly Leu Gly
            1125                1130                1135
Leu His Ile Ser Ser Glu Arg Gly Leu Gly Leu Cys Tyr Ser Pro Arg
            1140                1145                1150
Ile Leu Glu Ile Leu Glu Thr His Arg Ala Arg Gly Thr His Arg Ala
    1155                1160                1165
Leu Ala Gly Leu Leu Tyr Ser Ala Ser Asn Leu Tyr Ser Leu Tyr Ser
1170                1175                1180
Thr Tyr Arg Ala Ser Asn Thr Arg Pro Ala Leu Ala Ser Glu Arg Ile
1185                1190                1195                1200
Leu Glu Gly Leu Thr Arg Pro Pro His Glu His Ile Ser Leu Glu Ile
            1205                1210                1215
Leu Glu Val Ala Leu Ala Ser Asn Thr His Arg Leu Tyr Ser Ile Leu
            1220                1225                1230
Glu Gly Leu Tyr Leu Glu Ser Glu Arg Pro His Glu Leu Glu Leu Tyr
            1235                1240                1245
Ser Ala Leu Ala Val Ala Leu Thr His Arg Gly Leu Thr His Arg Leu
            1250                1255                1260
Glu Ile Leu Glu Gly Leu Tyr Pro His Glu Leu Glu Ile Leu Glu Leu
1265                1270                1275                1280
Glu Ser Glu Arg Gly Leu Asn Met Glu Thr Pro Arg Met Glu Thr Ser
                1285                1290                1295
Glu Arg Met Glu Thr Ala Leu Ala Gly Leu Asn Thr His Arg Ala Leu
            1300                1305                1310
Ala Gly Leu Asn Cys Tyr Ser Leu Glu Ala Ser Pro Ser Glu Arg Cys
            1315                1320                1325
Tyr Ser Thr Tyr Arg Thr Tyr Arg Val Ala Leu Pro Arg Gly Leu Tyr
            1330                1335                1340
Cys Tyr Ser Ala Ser Pro Ala Arg Gly Pro His Glu Val Ala Leu Thr
1345                1350                1355                1360
His Arg Ala Ser Asn Ala Arg Gly Thr Tyr Arg Ala Ser Pro Leu Tyr
            1365                1370                1375
Ser Cys Tyr Ser Pro Arg Gly Leu Leu Tyr Ser Ala Ser Pro Gly Leu
            1380                1385                1390
Asn Cys Tyr Ser Pro His Glu Cys Tyr Ser Ala Leu Ala Ile Leu Glu
```

-continued

```
                   1395                    1400                         1405
Leu Tyr Ser Gly Leu Ala Ser Asn Ser Glu Arg Ile Leu Glu Val Ala
        1410                    1415                    1420
Leu Gly Leu Ser Glu Arg Ala Ser Asn Pro His Glu Leu Glu Thr His
1425                    1430                    1435                    1440
Arg Ala Ser Asn Val Ala Leu Val Ala Leu Thr His Arg Gly Leu Gly
                1445                    1450                    1455
Leu Tyr Pro Arg Met Glu Thr Ala Ser Pro Cys Tyr Ser Ile Leu Glu
                1460                    1465                    1470
Pro Arg Thr Tyr Arg Gly Leu Asn Gly Leu Cys Tyr Ser Leu Tyr Ser
                1475                    1480                    1485
Gly Leu Tyr Ala Arg Gly Ile Leu Glu Thr His Arg Gly Leu Ala Ser
        1490                    1495                    1500
Asn Ala Leu Ala Leu Glu Val Ala Leu Thr His Arg Pro His Glu Val
1505                    1510                    1515                    1520
Ala Leu Leu Tyr Ser Cys Tyr Ser Ala Arg Gly Pro His Glu Gly Leu
                1525                    1530                    1535
Tyr Cys Tyr Ser Gly Leu Thr Tyr Arg Ala Leu Ala Ser Glu Arg Ile
                1540                    1545                    1550
Leu Glu Pro His Glu Gly Leu Asn Ser Glu Arg Leu Tyr Ser Pro Arg
        1555                    1560                    1565
Leu Glu Ala Ser Pro Ala Ser Asn Gly Leu Tyr Pro His Glu Leu Glu
        1570                    1575                    1580
Gly Leu Thr Tyr Arg Ser Glu Arg Gly Leu Tyr Ala Ser Pro Thr His
1585                    1590                    1595                    1600
Arg Leu Glu Gly Leu Tyr Leu Glu Ala Ser Asn Ala Leu Ala Val Ala
                1605                    1610                    1615
Leu Ala Ser Asn Leu Glu His Ile Ser Pro His Glu Met Glu Thr Leu
                1620                    1625                    1630
Tyr Ser Ala Arg Gly Leu Glu Ala Arg Gly Ala Ser Asn Gly Leu Tyr
        1635                    1640                    1645
Ile Leu Glu Ile Leu Glu Ala Ser Pro Pro His Glu Thr Tyr Arg Ala
        1650                    1655                    1660
Ser Asn Leu Tyr Ser Thr His Arg Gly Leu Leu Tyr Ser Thr Tyr Arg
1665                    1670                    1675                    1680
Gly Leu Tyr Thr Tyr Arg Ile Leu Glu Ser Glu Arg Gly Leu Tyr Ala
                1685                    1690                    1695
Ser Pro Ala Leu Ala Leu Glu Leu Tyr Ser Ser Glu Arg Ala Ser Asn
        1700                    1705                    1710
Gly Leu Ser Glu Arg Ala Ser Pro Ile Leu Glu Pro Arg Gly Leu Ser
        1715                    1720                    1725
Glu Arg Ile Leu Glu Pro His Glu Pro Arg Ala Arg Gly Leu Tyr Ser
        1730                    1735                    1740
Ser Glu Arg Leu Glu Ile Leu Glu Pro His Glu Ala Ser Pro Ser Glu
1745                    1750                    1755                    1760
Arg Val Ala Leu Ile Leu Glu Ala Ser Pro Gly Leu Tyr Leu Tyr Ser
                1765                    1770                    1775
Thr Tyr Arg Ala Arg Gly Thr Tyr Arg Met Glu Thr Ile Leu Glu Gly
                1780                    1785                    1790
Leu Gly Leu Ser Glu Arg Leu Glu Leu Glu Ser Glu Arg Gly Leu Tyr
        1795                    1800                    1805
Gly Leu Tyr Gly Leu Tyr Thr His Arg Val Ala Leu Pro His Glu Ser
        1810                    1815                    1820
```

```
Glu  Arg  Leu  Glu  Ala  Ser  Asn  Ala  Ser  Pro  Leu  Tyr  Ser  Ser  Glu  Arg
1825                1830                1835                          1840

Ser  Glu  Arg  Ser  Glu  Arg  Thr  His  Arg  Ala  Leu  Ala  Gly  Leu  Asn  Leu
               1845                1850                          1855

Tyr  Ser  Pro  His  Glu  Val  Ala  Leu  Val  Ala  Leu  Thr  Tyr  Arg  Ile  Leu
               1860                1865                          1870

Glu  Leu  Tyr  Ser  Leu  Tyr  Ser  Val  Ala  Leu  Ala  Arg  Gly  Ile  Leu  Glu
          1875                1880                     1885

Gly  Leu  Asn  Thr  Tyr  Arg  Ala  Ser  Pro  Val  Ala  Leu  Ser  Glu  Arg  Gly
          1890                1895                     1900

Leu  Gly  Leu  Asn  Thr  Tyr  Arg  Thr  His  Arg  Thr  His  Arg  Ala  Leu  Ala
1905                1910                1915                          1920

Pro  Arg  Ile  Leu  Glu  Gly  Leu  Asn  Ser  Glu  Arg  Thr  His  Arg  His  Ile
                    1925                1930                          1935

Ser  Thr  His  Arg  Ala  Ser  Pro  Pro  His  Glu  Pro  His  Glu  Ser  Glu  Arg
               1940                1945                     1950

Thr  His  Arg  Cys  Tyr  Ser  Thr  His  Arg  Gly  Leu  Tyr  Leu  Tyr  Ser  Cys
               1955                1960                     1965

Tyr  Ser  Ser  Glu  Arg  Ala  Ser  Pro  Cys  Tyr  Ser  Ala  Arg  Gly  Leu  Tyr
1970                     1975                     1980

Ser  Gly  Leu  Gly  Leu  Asn  Pro  Arg  Ile  Leu  Glu  Thr  His  Arg  Gly  Leu
1985                1990                1995                          2000

Tyr  Thr  Tyr  Arg  Gly  Leu  Asn  Ala  Ser  Pro  Pro  His  Glu  Cys  Tyr  Ser
                    2005                2010                          2015

Ile  Leu  Glu  Thr  His  Arg  Pro  Arg  Thr  His  Arg  Ser  Glu  Arg  Thr  Tyr
               2020                2025                     2030

Arg  Thr  Arg  Pro  Gly  Leu  Tyr  Cys  Tyr  Ser  Gly  Leu  Gly  Leu  Val  Ala
          2035                2040                     2045

Leu  Thr  Arg  Pro  Cys  Tyr  Ser  Leu  Glu  Ala  Leu  Ala  Ile  Leu  Glu  Ala
          2050                2055                     2060

Ser  Asn  Gly  Leu  Gly  Leu  Tyr  Ala  Leu  Ala  Thr  His  Arg  Cys  Tyr  Ser
2065                     2070                     2075                     2080

Gly  Leu  Tyr  Pro  His  Glu  Cys  Tyr  Ser  Ala  Arg  Gly  Ala  Ser  Asn  Val
               2085                2090                     2095

Ala  Leu  Thr  Tyr  Arg  Ala  Ser  Pro  Met  Glu  Thr  Ala  Ser  Pro  Gly  Leu
               2100                2105                     2110

Asn  Ser  Glu  Arg  Pro  His  Glu  Ala  Arg  Gly  Ile  Leu  Glu  Thr  Tyr  Arg
               2115                2120                     2125

Ser  Glu  Arg  Val  Ala  Leu  Ile  Leu  Glu  Leu  Tyr  Ser  Ser  Glu  Arg  Thr
          2130                2135                     2140

His  Arg  Ile  Leu  Glu  Leu  Tyr  Ser  Ser  Glu  Arg  Gly  Leu  Val  Ala  Leu
2145                2150                2155                          2160

Cys  Tyr  Ser  Ile  Leu  Glu  Ser  Glu  Arg  Gly  Leu  Tyr  Pro  His  Glu  Val
               2165                2170                          2175

Ala  Leu  Gly  Leu  Tyr  Ala  Leu  Ala  Leu  Tyr  Ser  Cys  Tyr  Ser  Pro  His
               2180                2185                          2190

Glu  Thr  His  Arg  Val  Ala  Leu  Ser  Glu  Arg  Gly  Leu  Gly  Leu  Val  Ala
          2195                2200                     2205

Leu  Pro  Arg  Ser  Glu  Arg  Gly  Leu  Ser  Glu  Arg  Gly  Leu  Tyr  Thr  Tyr
          2210                2215                     2220

Arg  Pro  His  Glu  Gly  Leu  Asn  Ala  Leu  Ala  Ala  Ser  Pro  Ile  Leu  Glu
2225                2230                     2235                     2240

Leu  Glu  Ala  Leu  Ala  Ala  Ser  Pro  Pro  His  Glu  His  Ile  Ser  Ala  Ser
                    2245                2250                     2255
```

```
Asn Ala Ser Pro Gly Leu Tyr Leu Glu Thr His Arg Ile Leu Glu Gly
            2260                2265                2270
Leu Tyr Gly Leu Asn Leu Glu Ile Leu Glu Ala Leu Ala His Ile Ser
        2275                2280                2285
Gly Leu Tyr Pro Arg Ala Ser Pro Ser Glu Arg His Ile Ser Val Ala
        2290                2295                2300
Leu Thr Tyr Arg Ala Leu Ala Gly Leu Tyr Ala Ser Asn Ile Leu Glu
2305                2310                2315                2320
Ala Leu Ala Ala Arg Gly Leu Glu Ala Ser Asn Ala Ser Asn Pro Arg
                2325                2330                2335
Ser Glu Arg Leu Tyr Ser Met Glu Thr Pro His Glu Gly Leu Tyr His
            2340                2345                2350
Ile Ser Pro Arg Gly Leu Asn Leu Glu Ser Glu Arg His Ile Ser Gly
        2355                2360                2365
Leu Asn Gly Leu Tyr Ala Ser Pro Pro Arg Ile Leu Glu Pro His Glu
        2370                2375                2380
Ser Glu Arg Leu Tyr Ser Leu Tyr Ser Thr His Arg Leu Glu Ala Ser
2385                2390                2395                2400
Pro Thr His Arg Ala Ser Asn Ala Ser Pro Leu Glu Ser Glu Arg Thr
                2405                2410                2415
Arg Pro Ala Ser Pro Cys Tyr Ser Ser Glu Arg Ala Leu Ala Ile Leu
                2420                2425                2430
Glu Gly Leu Tyr Leu Tyr Ser Leu Tyr Ser Thr His Arg Ile Leu Glu
            2435                2440                2445
Thr His Arg Ile Leu Glu Leu Tyr Ser Ser Glu Arg Cys Tyr Ser Gly
    2450                2455                2460
Leu Tyr Thr Tyr Arg Ala Ser Pro Thr His Arg Thr Tyr Arg Ala Arg
2465                2470                2475                2480
Gly Pro His Glu Leu Tyr Ser Thr His Arg Gly Leu Tyr Leu Glu Ala
                2485                2490                2495
Ser Asn Gly Leu Asn Ile Leu Glu Ser Glu Arg Ala Ser Pro Ile Leu
            2500                2505                2510
Glu Pro Arg Val Ala Leu Gly Leu Asn Pro His Glu Thr His Arg Ala
            2515                2520                2525
Ser Pro Gly Leu Asn Ala Ser Asn Ser Glu Arg Pro His Glu Thr Tyr
        2530                2535                2540
Arg Met Glu Thr Gly Leu Leu Tyr Ser Ile Leu Glu Pro His Glu Ser
2545                2550                2555                2560
Glu Arg Leu Glu Gly Leu Tyr Leu Tyr Ser Leu Glu Leu Tyr Ser Ile
            2565                2570                2575
Leu Glu Val Ala Leu Leu Glu Ala Ser Pro Leu Glu Pro Arg Ser Glu
            2580                2585                2590
Arg Gly Leu Leu Glu Pro His Glu Leu Tyr Ser Thr His Arg Val Ala
        2595                2600                2605
Leu Pro Arg Leu Tyr Ser Leu Tyr Ser Pro Arg Ile Leu Glu Leu Glu
        2610                2615                2620
Ser Glu Arg Ser Glu Arg Val Ala Leu Ser Glu Arg Leu Glu Ser Glu
2625                2630                2635                2640
Arg Cys Tyr Ser Leu Tyr Ser Gly Leu Tyr Cys Tyr Ser Pro His Glu
                2645                2650                2655
Leu Glu Cys Tyr Ser Ser Glu Arg Gly Leu Asn Gly Leu Tyr Leu Glu
            2660                2665                2670
Ala Arg Gly Cys Tyr Ser Ala Leu Ala Ala Leu Ala Ser Glu Arg Pro
```

-continued

```
                     2675                        2680                             2685
        His Glu Ile Leu Glu Ser Glu Arg Ala Ser Pro Ile Leu Glu Thr His
            2690                    2695                        2700
        Arg Pro His Glu Ser Glu Arg Ala Leu Ala Ala Arg Gly Leu Glu Thr
        2705                2710                    2715                    2720
        His Arg Met Glu Thr Leu Tyr Ser Gly Leu Asn Cys Tyr Ser Ser Glu
                        2725                    2730                    2735
        Arg Leu Glu Ser Glu Arg Thr His Arg Thr Tyr Arg Gly Leu Asn Ile
                    2740                    2745                    2750
        Leu Glu Ala Leu Ala Val Ala Leu Leu Tyr Ser Leu Tyr Ser Gly Leu
                    2755                    2760                    2765
        Tyr Ala Leu Ala Ala Ser Asn Leu Tyr Ser Thr Tyr Arg Ala Ser Asn
                2770                    2775                    2780
        Leu Glu Thr His Arg Met Glu Thr Pro His Glu Cys Tyr Ser Thr His
        2785                    2790                    2795                    2800
        Arg Ser Glu Arg Ala Ser Asn Pro Arg Gly Leu Leu Tyr Ser Gly Leu
                            2805                    2810                    2815
        Asn Leu Tyr Ser Met Glu Thr Ile Leu Glu Ile Leu Glu Gly Leu Pro
                        2820                    2825                    2830
        Arg Gly Leu Gly Leu Tyr Ala Ser Pro Leu Tyr Ser Ser Glu Arg Thr
                    2835                    2840                    2845
        Tyr Arg Ser Glu Arg Val Ala Leu Gly Leu Ala Ala Leu Glu Val
                2850                    2855                    2860
        Ala Leu Ala Ser Pro Ser Glu Arg Val Ala Leu Ala Leu Ala Val Ala
        2865                    2870                    2875                    2880
        Leu Leu Glu Gly Leu Pro Arg Gly Leu Ala Ser Asn Ile Leu Glu Ile
                            2885                    2890                    2895
        Leu Glu Ala Ser Pro Gly Leu Asn Ala Ser Asn Ala Ser Pro Gly Leu
                        2900                    2905                    2910
        Asn His Ile Ser Ala Leu Ala His Ile Ser Gly Leu Gly Leu Gly Leu
                    2915                    2920                    2925
        Asn Gly Leu Asn Thr Tyr Arg Ala Ser Asn Ser Glu Arg Ala Ser Pro
                    2930                    2935                    2940
        Thr His Arg Ser Glu Arg Val Ala Leu Thr Arg Pro Ser Glu Arg Pro
        2945                    2950                    2955                    2960
        His Glu Thr Arg Pro Ala Ser Pro Thr Tyr Arg Val Ala Leu Leu Tyr
                            2965                    2970                    2975
        Ser Ser Glu Arg Pro Arg Pro His Glu Ala Ser Asn Pro His Glu Ile
                        2980                    2985                    2990
        Leu Glu Ala Leu Ala Ser Glu Arg His Ile Ser Pro His Glu Gly Leu
                    2995                    3000                    3005
        Tyr Ser Glu Arg Pro His Glu Pro His Glu Ala Ser Pro Thr His Arg
                3010                    3015                    3020
        Val Ala Leu Ala Arg Gly Val Ala Leu Val Ala Leu Leu Glu Leu Glu
        3025                    3030                    3035                    3040
        Ile Leu Glu Leu Glu Pro His Glu Val Ala Leu Pro His Glu Ala Leu
                            3045                    3050                    3055
        Ala Leu Glu Ala Leu Ala Thr Tyr Arg Leu Glu Cys Tyr Ser Ser Glu
                        3060                    3065                    3070
        Arg Ile Leu Glu Val Ala Leu Ala Leu Ala Thr His Arg Met Glu Thr
                        3075                    3080                    3085
        Cys Tyr Ser Ala Arg Gly Gly Leu Tyr Thr Tyr Arg Val Ala Leu Ala
                        3090                    3095                    3100
```

| | | | | | | | | | | | | | | |
|---|---|---|---|---|---|---|---|---|---|---|---|---|---|---|
| Arg | Gly | Ala | Ser | Asn | Leu | Tyr | Ser | Ser | Glu | Arg | Thr | Tyr | Arg | Leu | Tyr |
| 3105 | | | | | 3110 | | | | 3115 | | | | | 3120 |
| Ser | Thr | His | Arg | Leu | Tyr | Ser | Thr | Tyr | Arg | Ile | Leu | Glu | Gly | Leu | Ala |
| | | | 3125 | | | | | 3130 | | | | | | 3135 |
| Ser | Pro | Thr | His | Arg | Ala | Ser | Asn | Ala | Ser | Pro | Thr | Tyr | Arg | Ser | Glu |
| | | | 3140 | | | | | 3145 | | | | | 3150 | | |
| Arg | Leu | Glu | Val | Ala | Leu | Ser | Glu | Arg | Thr | His | Arg | Ser | Glu | Arg | Ser |
| | | 3155 | | | | | | 3160 | | | | 3165 | | | |
| Glu | Arg | Gly | Leu | Tyr | Leu | Tyr | Ser | Ala | Ser | Pro | Thr | His | Arg | Ile | Leu |
| | 3170 | | | | | 3175 | | | | | 3180 | | | | |
| Glu | Thr | His | Arg | Ala | Arg | Gly | Ala | Arg | Gly | Ala | Arg | Gly | Pro | Arg | Pro |
| 3185 | | | | | 3190 | | | | | 3195 | | | | | 3200 |
| Arg | Leu | Glu | Ala | Ser | Pro | Pro | His | Glu | Ser | Glu | Arg | Gly | Leu | Tyr | Ile |
| | | | | 3205 | | | | | 3210 | | | | | 3215 | |
| Leu | Glu | | | | | | | | | | | | | | |